US010851417B2

(12) United States Patent
Baird et al.

(10) Patent No.: US 10,851,417 B2
(45) Date of Patent: Dec. 1, 2020

(54) HIGH THROUGHPUT SEQUENCING

(71) Applicant: University College Cardiff Consultants Limited, Cardiff (GB)

(72) Inventors: Duncan Baird, South Glamorgan (GB); Kevin Norris, South Glamorgan (GB)

(73) Assignee: UNIVERSITY COLLEGE CARDIFF CONSULTANTS LIMITED, Cardiff (GB)

( * ) Notice: Subject to any disclaimer, the term of this patent is extended or adjusted under 35 U.S.C. 154(b) by 311 days.

(21) Appl. No.: 15/518,363

(22) PCT Filed: Oct. 14, 2015

(86) PCT No.: PCT/GB2015/053023
§ 371 (c)(1),
(2) Date: Apr. 11, 2017

(87) PCT Pub. No.: WO2016/059398
PCT Pub. Date: Apr. 21, 2016

(65) Prior Publication Data
US 2017/0306404 A1 Oct. 26, 2017

(30) Foreign Application Priority Data
Oct. 14, 2014 (GB) .................................. 1418144.0

(51) Int. Cl.
C12P 19/34 (2006.01)
C12Q 1/6883 (2018.01)
C12Q 1/6886 (2018.01)
C12Q 1/6874 (2018.01)
G01N 21/64 (2006.01)
C12Q 1/68 (2018.01)
G01N 35/00 (2006.01)

(52) U.S. Cl.
CPC ......... C12Q 1/6883 (2013.01); C12Q 1/6874 (2013.01); C12Q 1/6886 (2013.01); G01N 21/64 (2013.01); G01N 21/6486 (2013.01); C12Q 1/68 (2013.01); G01N 35/00 (2013.01)

(58) Field of Classification Search
CPC ...... C12Q 1/68; C12Q 1/6874; C12Q 1/6883; G01N 21/64; G01N 21/6486; G01N 35/00
See application file for complete search history.

(56) References Cited

U.S. PATENT DOCUMENTS

| 5,741,677 A | 4/1998 | Kozlowski et al. |
| 5,834,193 A | 11/1998 | Kozlowski et al. |
| 6,197,557 B1 | 3/2001 | Makarov et al. |
| 2012/0122700 A1* | 5/2012 | Medveczky ........... C12Q 1/705 506/2 |
| 2014/0024034 A1 | 1/2014 | Tanaka |
| 2016/0032360 A1* | 2/2016 | Keefe ................... C12Q 1/6851 435/6.12 |

FOREIGN PATENT DOCUMENTS

| CN | 102618633 A | 8/2012 |
| WO | 96/12821 A | 5/1996 |
| WO | 96/41016 A1 | 12/1996 |
| WO | 03/000927 A2 | 1/2003 |
| WO | 2004068110 A2 | 8/2004 |
| WO | 2009/021518 A1 | 2/2009 |
| WO | 2013024264 A1 | 2/2013 |

OTHER PUBLICATIONS

Cawthon., NAR, vol. 39m No. 10, e47, pp. 1-6, (Year: 2002).*
Search Report dated Jun. 22, 2015 of the Patent Office of Great Britain for Application No. GB1418144.0.
Written Opinion and Search Report of the International Search Authority dated Nov. 1, 2016 for International application No. PCT/GB2015/053023.
Baird, et al., Extensive allelic variation and ultrashort telomeres in senescent human cells, Nature Genetics, vol. 33, Nature Publishing 2003; pp. 203-207.
Britt-Compton, et al., Structural stability and chromosome-specific telomere length is governed by cis-acting determinants in humans, Human Molecular Genetics, 2006, vol. 15, No. 5; pp. 725-733.
Lin, et al., Telomere dysfunction accurately predicts clinical outcome in chronic lymphocytic leukaemia, even in patients with early stage disease, British Journal of Haematology, 2014, vol. 167, pp. 214-223.
English machine translation of CN 102618633.
Forstemann et al. Telomerase-dependent repeat divergence at the 3' ends of yeast telomeres. Swiss Institute for Exper.Cancer Research, 2000 vol. 28.

(Continued)

*Primary Examiner* — Cynthia B Wilder
(74) *Attorney, Agent, or Firm* — King & Schickli, PLLC

(57) ABSTRACT

The invention relates to a high throughput method for determining telomere length of mammalian chromosomal DNA; primers for use in said method; a kit comprising said primers; use of said method to diagnose or prognose or to determine the risk of developing a telomere shortening disease such as cancer, ageing, neurological disorders including Alzheimer's disease, Parkinson's disease and other dementias, brain infarction, heart disease, chronic HIV infection, chronic hepatitis, skin diseases, chronic inflammatory bowel disease including ulcerative colitis, anaemia, atherosclerosis, Barrett's oesophagus and cancers including pre-cancerous conditions, infertility, telomere syndromes including dyskeratosis congenita, aplastic anaemia, idiopathic pulmonary fibrosis, familial myelodysplastic syndrome-acute myeloid leukaemia, Hoyeraal-Hreiderasson syndrome, Revesz syndrome, Coats plus syndrome, bone marrow failure, and cryptogenic liver cirrhosis. Additionally, the invention also has application in assessing an individual's suitability to be a transplantation donor, for example a bone marrow donor.

28 Claims, 35 Drawing Sheets
Specification includes a Sequence Listing.

(56) References Cited

OTHER PUBLICATIONS

Lin et al.; "Telomere dysfunction and fusion during the progression of chronic lymphocytic leukemia: evidence for a telomere crisis"; Blood, vol. 116, No. 11, Sep. 16, 2010, pp. 1899-1907.
International Search report and Written Opinion for International application No. PCT/GB2012/051936 dated Nov. 19, 2012.
Search Report for British application No. GB1113968.0 dated Dec. 15, 2011.
Capper, R. et al.; "The nature of telomere fusion and a definition of the critical telomere length in human cells"; Genes & Development; vol. 21, 2007, pp. 2495-2508.
Letsolo, B. T. et al.; "Fusion of short telomeres in human cells is characterized by extensice deletion and microhomology, and can result in complex rearrangements", Nucleic Acids Research, vol. 38, No. 6; Dec. 21, 2009, pp. 1841-1852.

\* cited by examiner

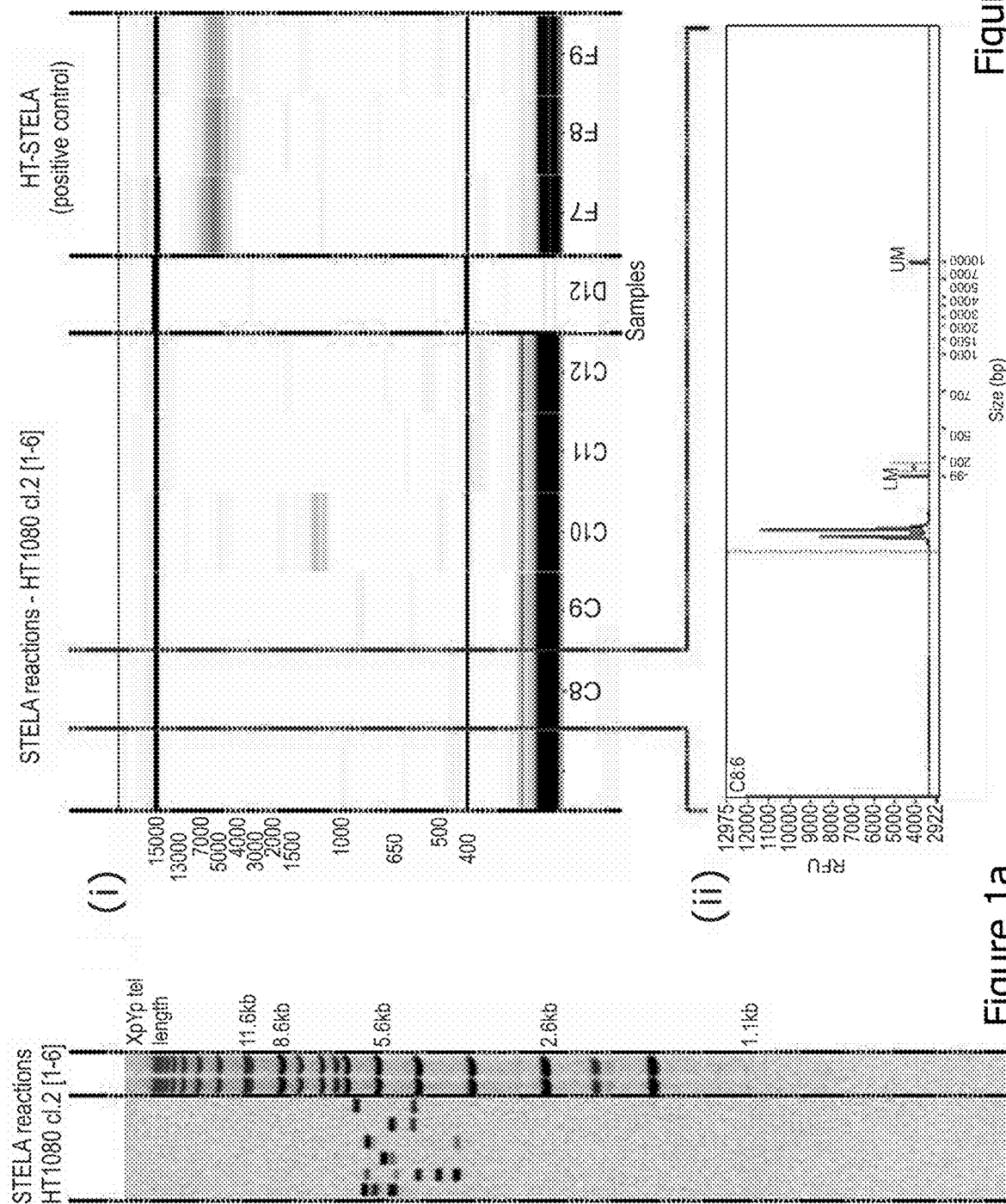

- E2 TGTCTCAGGGTCCTAGTG
- E3 TCTCAGGGTCCTAGTGTG
- E4 GTTGTCTCAGGGTCCTAG
- E5 GGGGTTGTCTCAGGGTCC
- E6 TTCTAGGGGTTGTCTCAG
- E7 TCTTCTAGGGGTTGTCTC

| Sample | Mean telomere length (kb) | |
|---|---|---|
| | STELA | HT-STELA |
| 4408 | 1.485 | 1.764 |
| 4521 | 8.598 | 4.591 |
| 4583 | 3.708 | 3.557 |
| 4065 | 1.29 | 1.317 |
| 4107 | 3.268 | 2.513 |
| 4304 | 4.268 | 3.368 |
| HT1080 cl.5 | 5.9 | 3.618 |
| MRC5 cl.5 (LA) | 3.048 | 3.702 |
| MRC5 cl.5 (UA) | 6.848 | - |

Figure 8a
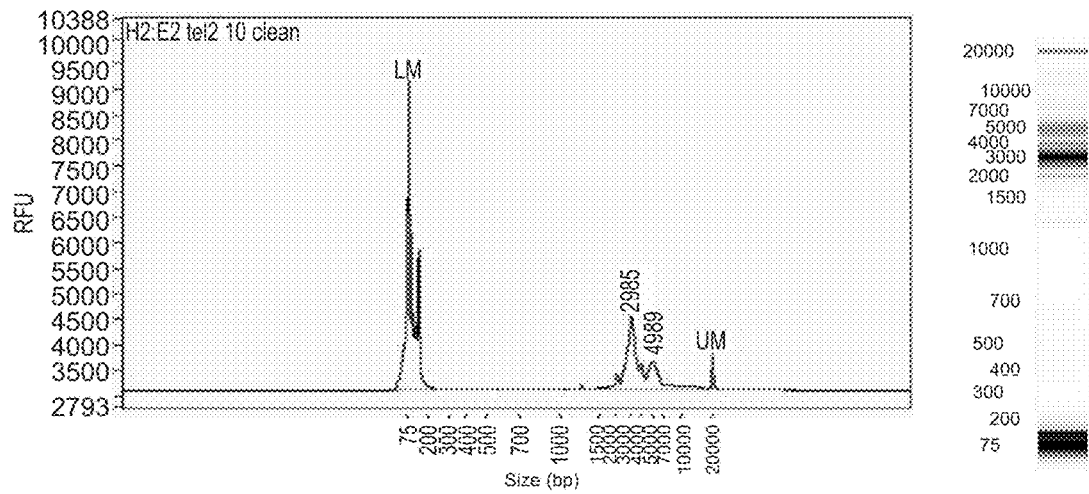
75bp and 20kb markers provided with kit
PCR reaction not purified
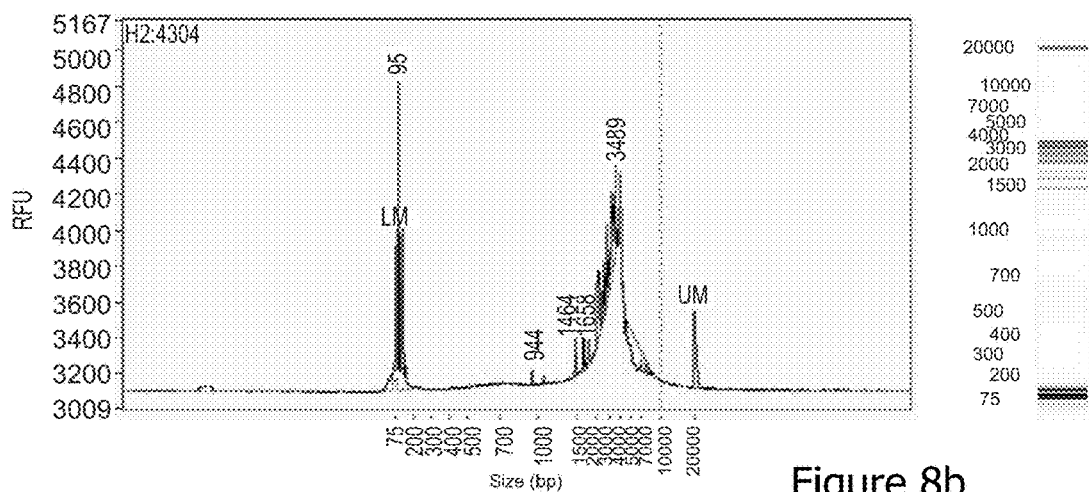
Figure 8b
75bp and 20kb markers provided with kit
PCR reaction purified
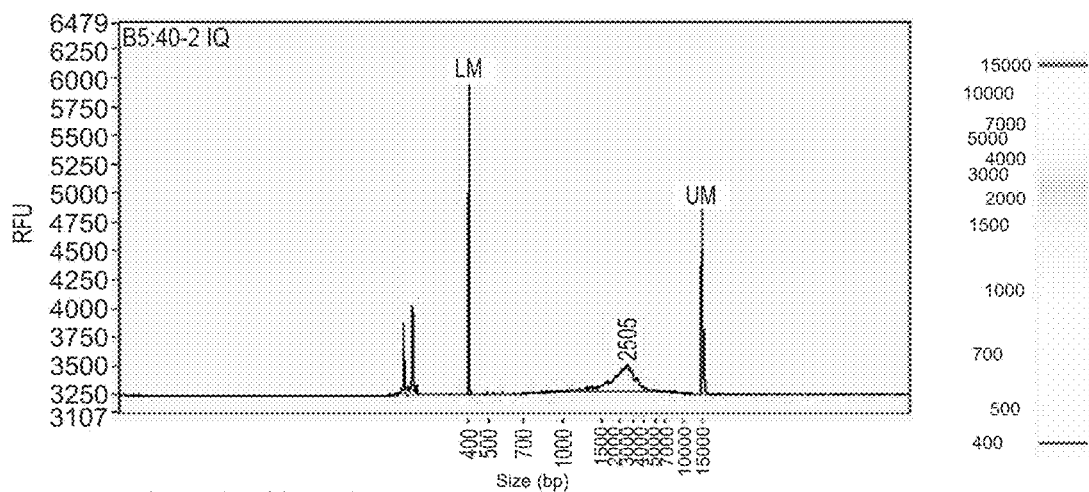
New 400bp and 15kb markers
Figure 8c

| Sample | Mean telomere length (kb) | |
|---|---|---|
| | STELA | HT-STELA |
| 4408 | 1.485 | 1.565 |
| MRC5 cl.5 (LA) | 3.048 | 3.029 |
| MRC5 cl.5 (UA) | 6.848 | 7.435 |
| 4521 | 8.598 | 8.335 |
| HT1080 cl.5 | 5.822 | 5.677 |
| 4583 | 3.708 | 3.981 |
| 4107 | 3.268 | 2.629 |
| 4304 | 4.268 | 3.812 |
| 4628 | 5.56 | 6.157 |
| 4536 | 7.351 | 7.045 |
| 4688 | 1.48 | 1.467 |

Figure 12a
Figure 12b
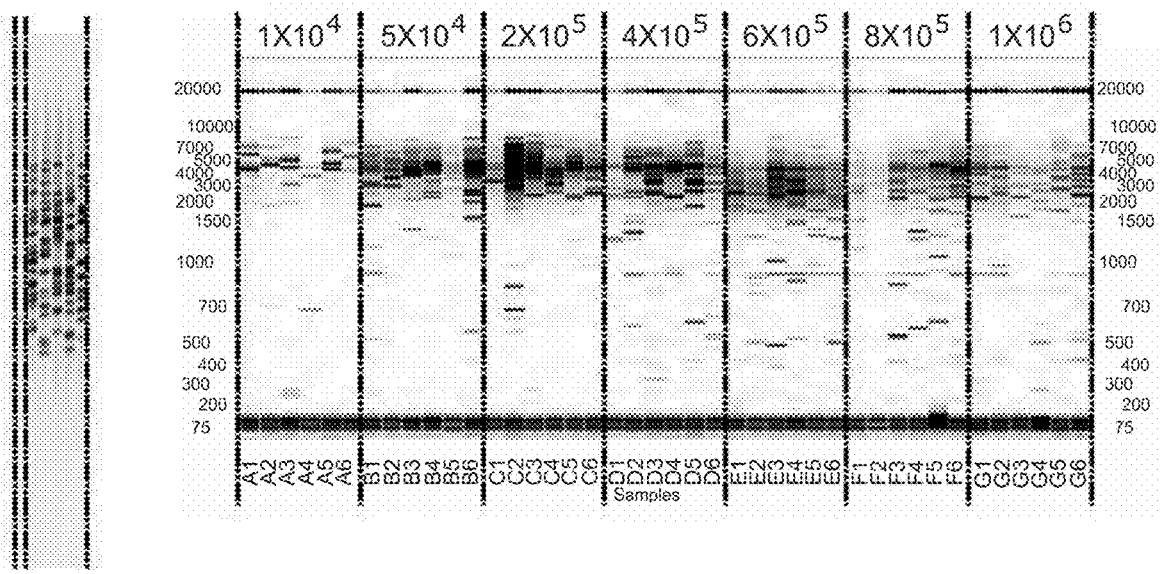
Figure 12c
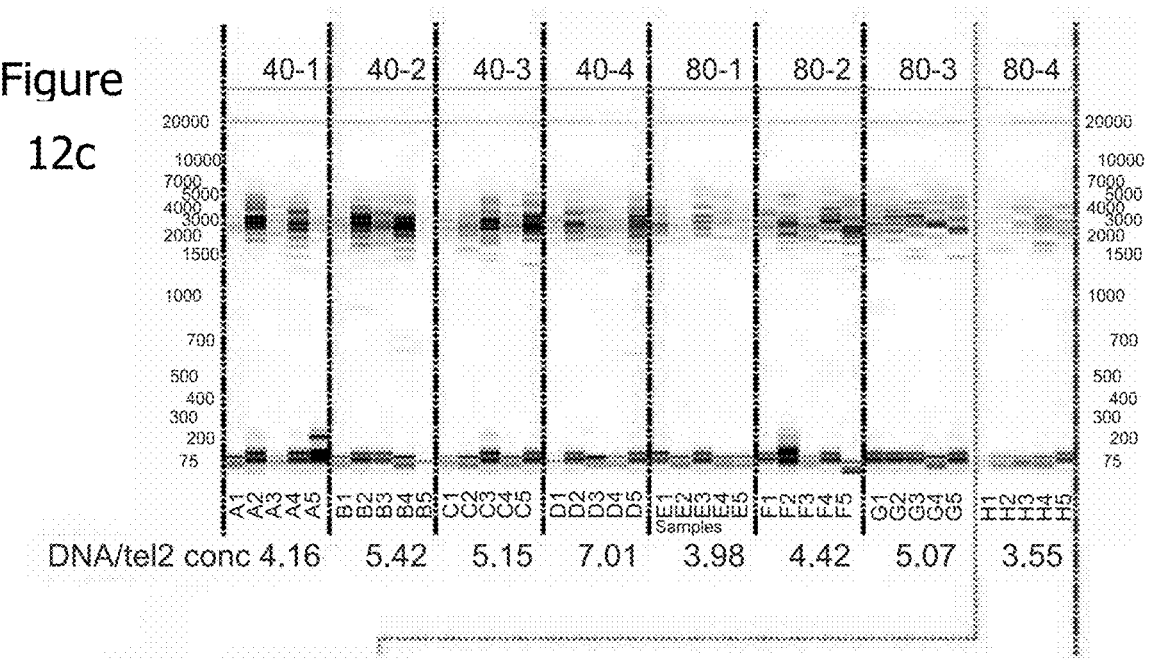
DNA/tel2 conc  4.16   5.42   5.15   7.01   3.98   4.42   5.07   3.55
DNA/tel2 added to reaction
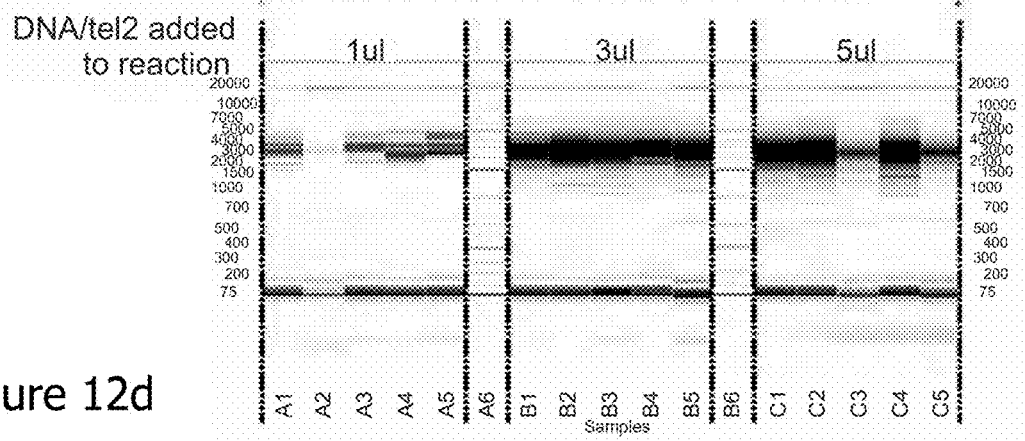
Figure 12d

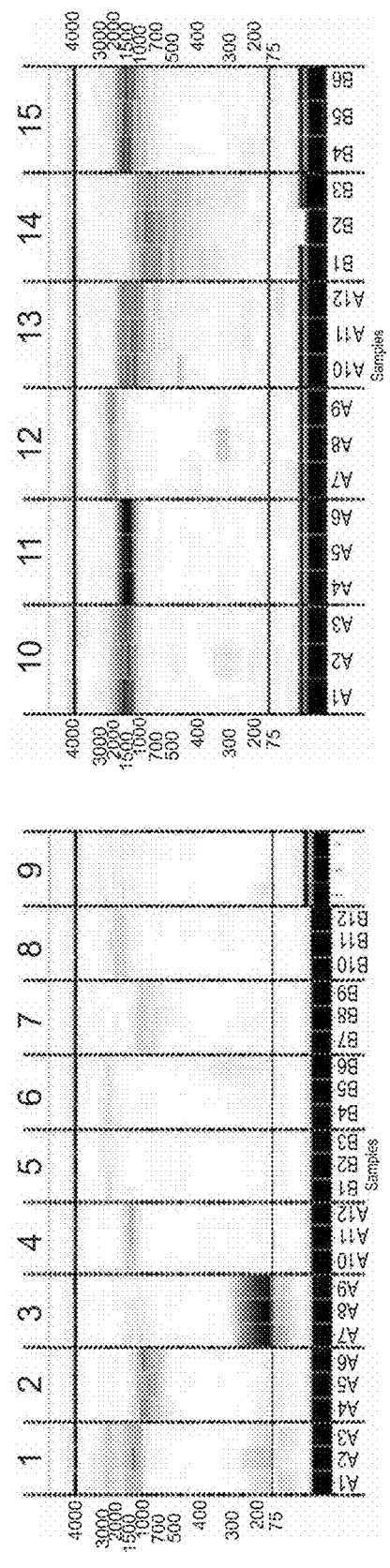
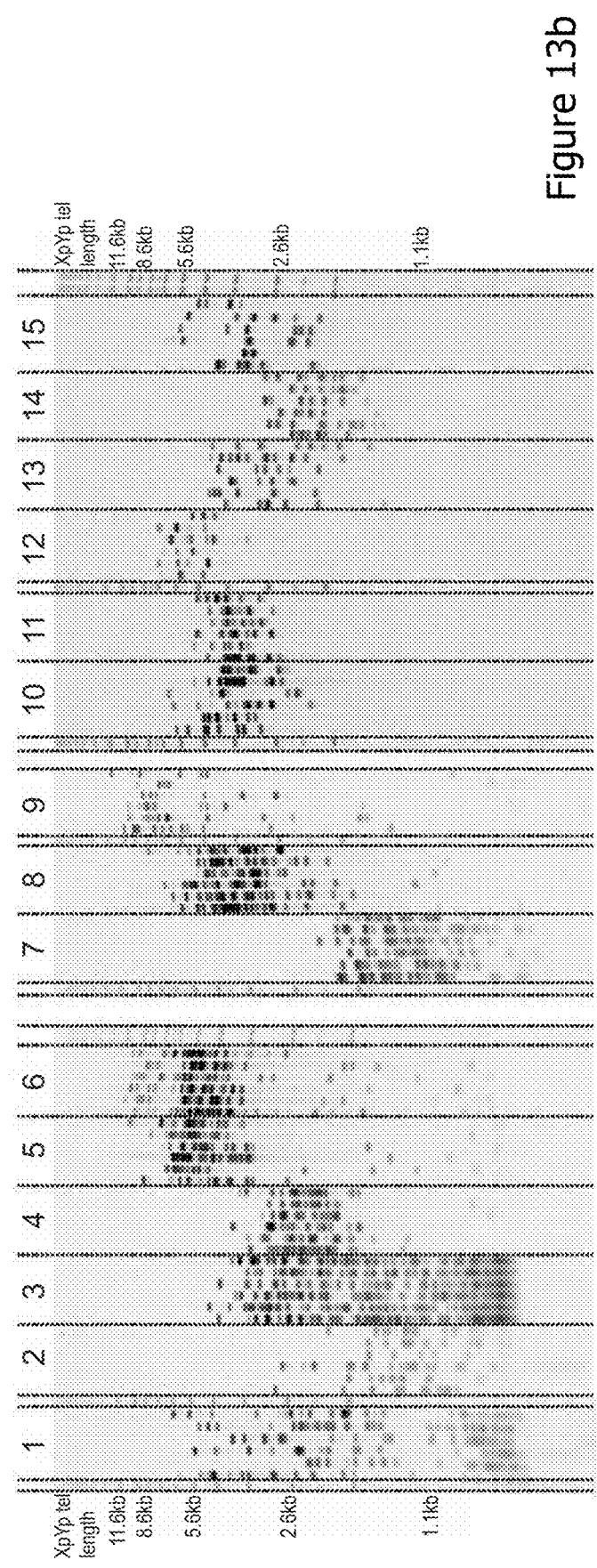
Figure 13a
Figure 13b

| CLL Sample | Mean telomere length (kb) | |
|---|---|---|
| | STELA | HT-STELA |
| 1 LA | 2.230 | 2.595 |
| 1 LA | 5.015 | 5.577 |
| 2 | 1.615 | 1.643 |
| 3 | N/A | N/A |
| 4 | 2.615 | 2.938 |
| 5 | 5.271 | 5.509 |
| 6 | 5.834 | 5.968 |
| 7 | 1.424 | 1.685 |
| 8 | 3.950 | 4.425 |
| 9 | N/A | N/A |
| 10 | 3.956 | 3.978 |
| 11 | 3.865 | 3.670 |
| 12 | 5.477 | 5.460 |
| 13 | 3.040 | 3.295 |
| 14 | 2.110 | 1.798 |
| 15 | 3.726 | 3.677 |

Figure 14a
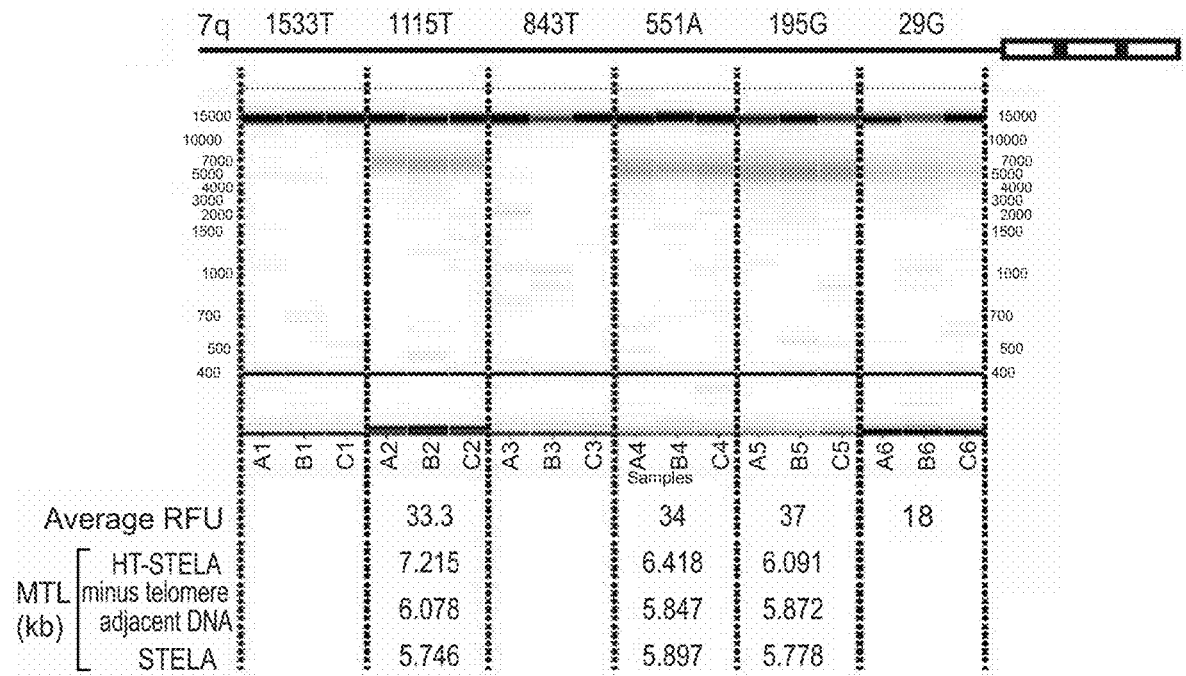
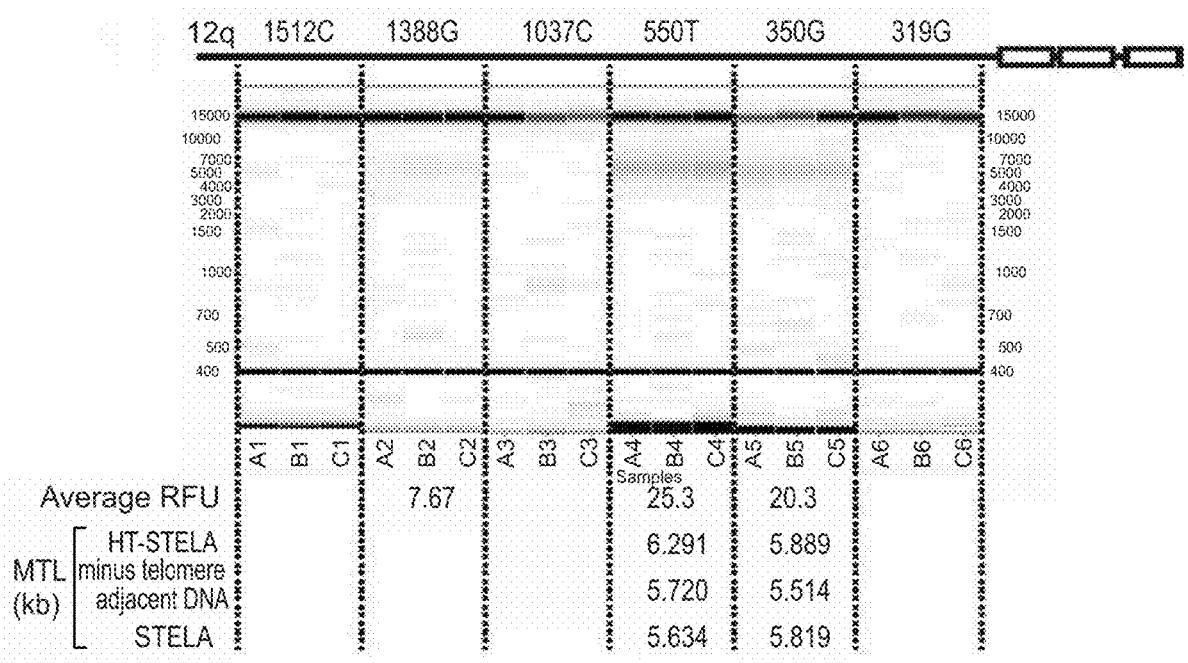
Figure 14b

Figure 15a
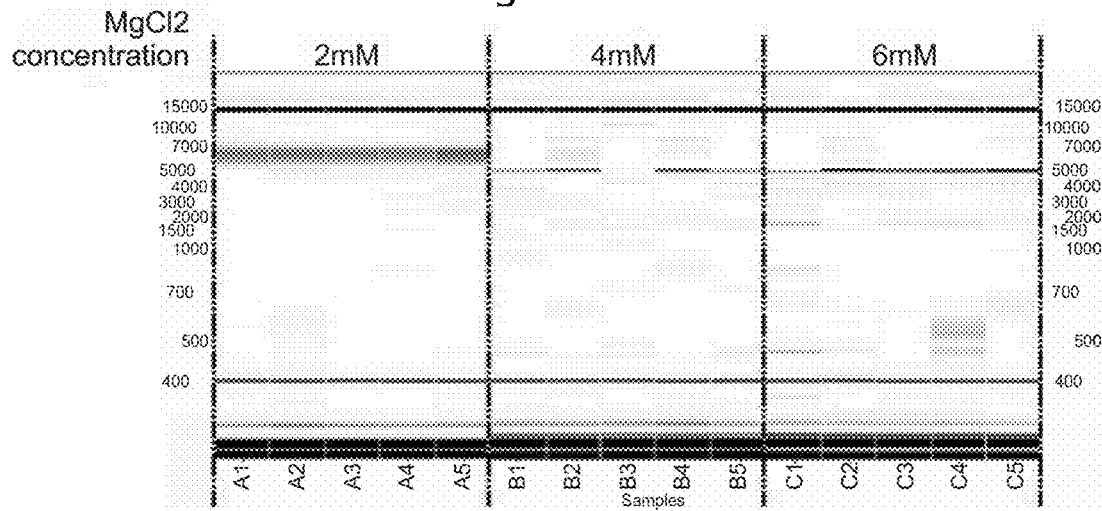
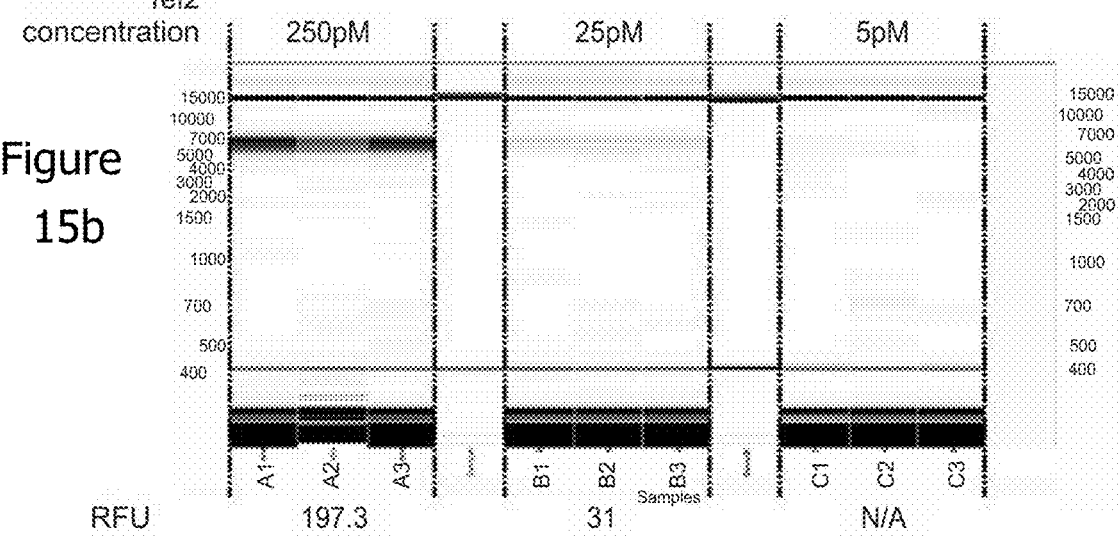
Figure 15b
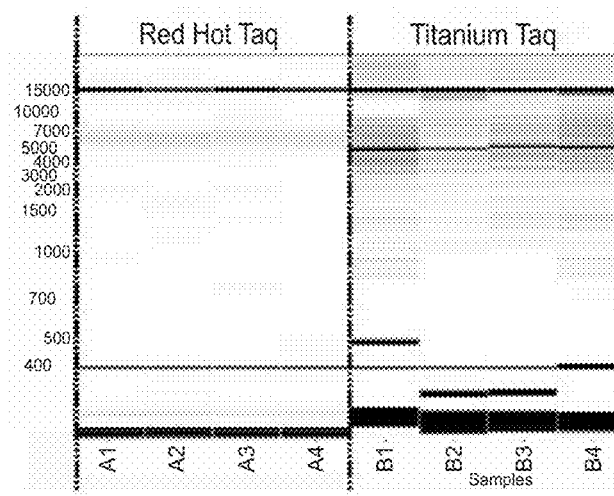
Figure 15c

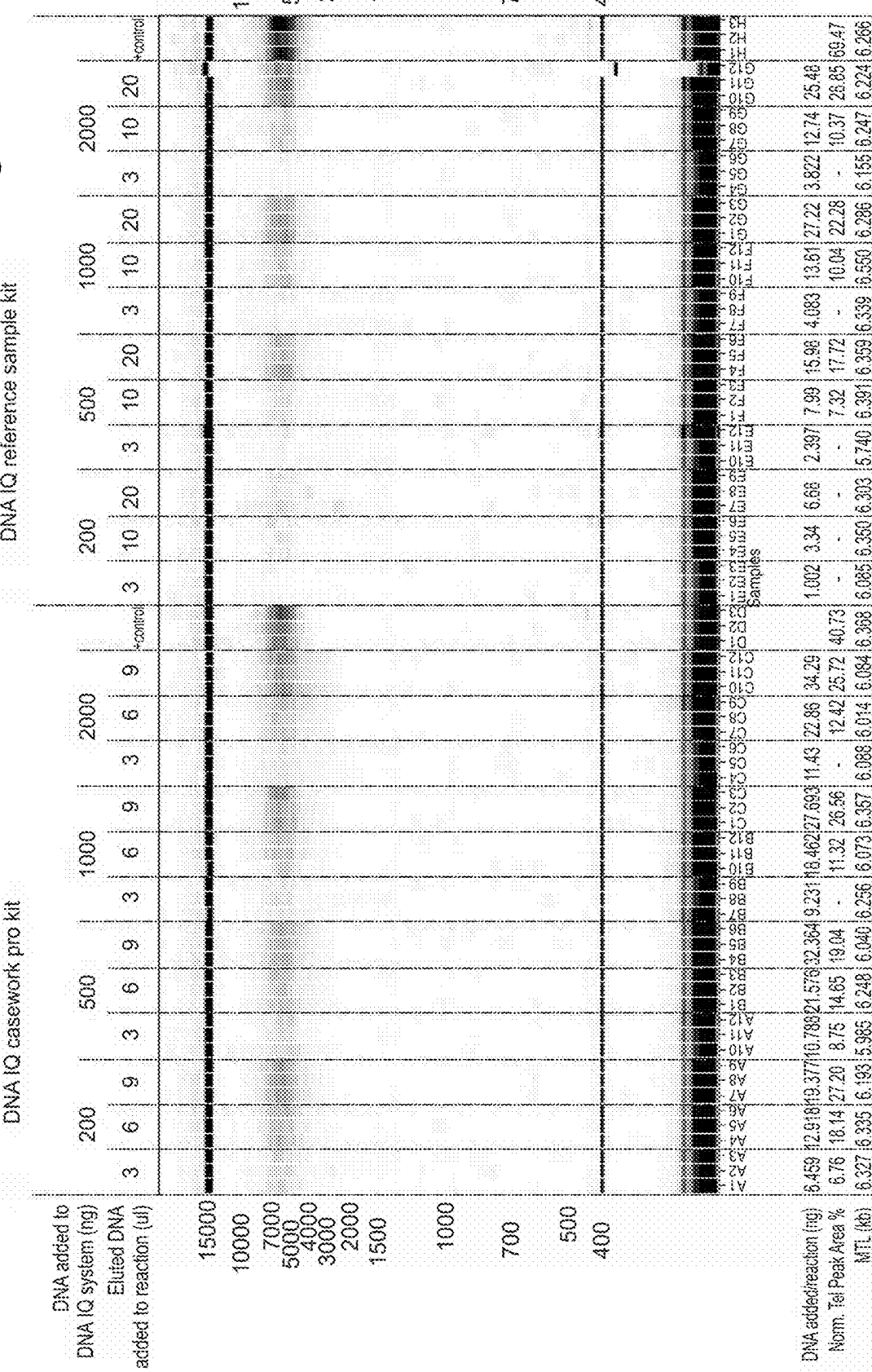

SEQUENCE LISTING

<160> NUMBER OF SEQ ID NOS: 38

<210> SEQ ID NO 1
<211> LENGTH: 21
<212> TYPE: DNA
<213> ORGANISM: Homo sapiens

<400> SEQUENCE: 1
gagctgcgtt ttgctgagca c                                           21

<210> SEQ ID NO 2
<211> LENGTH: 19
<212> TYPE: DNA
<213> ORGANISM: Homo sapiens

<400> SEQUENCE: 2
acggtggcat gcctctctc                                              19

<210> SEQ ID NO 3
<211> LENGTH: 23
<212> TYPE: DNA
<213> ORGANISM: Homo sapiens

<400> SEQUENCE: 3
tctgcgcctg cgatggcgct atg                                         23

<210> SEQ ID NO 4
<211> LENGTH: 24
<212> TYPE: DNA
<213> ORGANISM: Homo sapiens

<400> SEQUENCE: 4
gcattctctt caccacagat gttg                                        24

<210> SEQ ID NO 5
<211> LENGTH: 21
<212> TYPE: DNA
<213> ORGANISM: Homo sapiens

```
<400> SEQUENCE: 5
cccacacagt catctattgt t                                              21

<210> SEQ ID NO 6
<211> LENGTH: 25
<212> TYPE: DNA
<213> ORGANISM: Homo sapiens

<400> SEQUENCE: 6
gaggtgcagt agtgggatc taact                                           25

<210> SEQ ID NO 7
<211> LENGTH: 20
<212> TYPE: DNA
<213> ORGANISM: Homo sapiens

<400> SEQUENCE: 7
gggacagcat attctggttt                                                20

<210> SEQ ID NO 8
<211> LENGTH: 21
<212> TYPE: DNA
<213> ORGANISM: Homo sapiens

<400> SEQUENCE: 8
gcacagcctt ttggggtacc a                                              21

<210> SEQ ID NO 9
<211> LENGTH: 25
<212> TYPE: DNA
<213> ORGANISM: Homo sapiens

<400> SEQUENCE: 9
agtgggagat ccacaccgta gcgtg                                          25

<210> SEQ ID NO 10
<211> LENGTH: 26
<212> TYPE: DNA
<213> ORGANISM: Homo sapiens

<400> SEQUENCE: 10
ccatgcagtg ctaagacagc aatgag                                         26

<210> SEQ ID NO 11
<211> LENGTH: 24
<212> TYPE: DNA
<213> ORGANISM: Homo sapiens

<400> SEQUENCE: 11
cagaccttgg aggcacggcc ttcg                                           24

<210> SEQ ID NO 12
<211> LENGTH: 26
<212> TYPE: DNA
<213> ORGANISM: Homo sapiens

<400> SEQUENCE: 12
cctctggtca ttatgaatag ggcttc                                         26

<210> SEQ ID NO 13
<211> LENGTH: 18
<212> TYPE: DNA
<213> ORGANISM: Homo sapiens
```

```
<400> SEQUENCE: 13
ggggaaaaaa tgcccaag                                                 18

<210> SEQ ID NO 14
<211> LENGTH: 18
<212> TYPE: DNA
<213> ORGANISM: Homo sapiens

<400> SEQUENCE: 14
ccttctcttc ttgatgtc                                                 18

<210> SEQ ID NO 15
<211> LENGTH: 20
<212> TYPE: DNA
<213> ORGANISM: Homo sapiens

<400> SEQUENCE: 15
acagcctttt ggggtaccgt                                               20

<210> SEQ ID NO 16
<211> LENGTH: 26
<212> TYPE: DNA
<213> ORGANISM: Homo sapiens

<400> SEQUENCE: 16
ggcttcattg atggtgaata caatcg                                        26

<210> SEQ ID NO 17
<211> LENGTH: 22
<212> TYPE: DNA
<213> ORGANISM: Homo sapiens

<400> SEQUENCE: 17
gcagcgctga atattcaggg tg                                            22

<210> SEQ ID NO 18
<211> LENGTH: 22
<212> TYPE: DNA
<213> ORGANISM: Homo sapiens

<400> SEQUENCE: 18
cacttattag ttccagtctc tg                                            22

<210> SEQ ID NO 19
<211> LENGTH: 20
<212> TYPE: DNA
<213> ORGANISM: Homo sapiens

<400> SEQUENCE: 19
agaagcagcg aggagcttca                                               20

<210> SEQ ID NO 20
<211> LENGTH: 20
<212> TYPE: DNA
<213> ORGANISM: Homo sapiens

<400> SEQUENCE: 20
cctggcatgg tattgacatg                                               20

<210> SEQ ID NO 21
<211> LENGTH: 23
<212> TYPE: DNA
<213> ORGANISM: Homo sapiens
```

```
<400> SEQUENCE: 21
gctaggaatg gaatcattga ctc                                      23

<210> SEQ ID NO 22
<211> LENGTH: 24
<212> TYPE: DNA
<213> ORGANISM: Homo sapiens

<400> SEQUENCE: 22
gatactggga ggatcatatc tggc                                     24

<210> SEQ ID NO 23
<211> LENGTH: 22
<212> TYPE: DNA
<213> ORGANISM: Homo sapiens

<400> SEQUENCE: 23
ccattagcct gtgggtctg at                                        22

<210> SEQ ID NO 24
<211> LENGTH: 24
<212> TYPE: DNA
<213> ORGANISM: Homo sapiens

<400> SEQUENCE: 24
gaatccacgg attgctttgt gtac                                     24

<210> SEQ ID NO 25
<211> LENGTH: 21
<212> TYPE: DNA
<213> ORGANISM: Homo sapiens

<400> SEQUENCE: 25
aagcaggttg agaggctgag g                                        21

<210> SEQ ID NO 26
<211> LENGTH: 22
<212> TYPE: DNA
<213> ORGANISM: Homo sapiens

<400> SEQUENCE: 26
cacagggatg gttaggtatc tc                                       22

<210> SEQ ID NO 27
<211> LENGTH: 23
<212> TYPE: DNA
<213> ORGANISM: Homo sapiens

<400> SEQUENCE: 27
cgagcaagca tcggaacgtg act                                      23

<210> SEQ ID NO 28
<211> LENGTH: 20
<212> TYPE: DNA
<213> ORGANISM: Homo sapiens

<400> SEQUENCE: 28
accaggtttt ccagtgtgtt                                          20

<210> SEQ ID NO 29
<211> LENGTH: 20
<212> TYPE: DNA
<213> ORGANISM: Homo sapiens
```

```
<400> SEQUENCE: 29
cctgtaacgc tgttaggtac                                              20

<210> SEQ ID NO 30
<211> LENGTH: 21
<212> TYPE: DNA
<213> ORGANISM: Homo sapiens

<400> SEQUENCE: 30
cagggaccgg gacaaataga c                                            21

<210> SEQ ID NO 31
<211> LENGTH: 19
<212> TYPE: DNA
<213> ORGANISM: Homo sapiens

<400> SEQUENCE: 31 accagggct gatgtaacg                                                19

<210> SEQ ID NO 32
<211> LENGTH: 18
<212> TYPE: DNA
<213> ORGANISM: Homo sapiens

<400> SEQUENCE: 32
tgtctcaggg tcctagtg                                                18

<210> SEQ ID NO 33
<211> LENGTH: 18
<212> TYPE: DNA
<213> ORGANISM: Homo sapiens

<400> SEQUENCE: 33
tctcagggtc ctagtgtg                                                18

<210> SEQ ID NO 34
<211> LENGTH: 18
<212> TYPE: DNA
<213> ORGANISM: Homo sapiens

<400> SEQUENCE: 34
gttgtctcag ggtcctag                                                18

<210> SEQ ID NO 35
<211> LENGTH: 18
<212> TYPE: DNA
<213> ORGANISM: Homo sapiens

<400> SEQUENCE: 35
ggggttgtct cagggtcc                                                18

<210> SEQ ID NO 36
<211> LENGTH: 18
<212> TYPE: DNA
<213> ORGANISM: Homo sapiens

<400> SEQUENCE: 36
ttctaggggt tgtctcag                                                18

<210> SEQ ID NO 37
<211> LENGTH: 18
<212> TYPE: DNA
<213> ORGANISM: Homo sapiens
```

```
<400> SEQUENCE: 37
tcttctaggg gttgtctc                                              18

<210> SEQ ID NO 38
<211> LENGTH: 19
<212> TYPE: DNA
<213> ORGANISM: Homo sapiens

<400> SEQUENCE: 38
ctaatctgct cccwcccac                                             19
```

HIGH THROUGHPUT SEQUENCING

TECHNICAL FIELD

The invention relates to a high throughput method for determining telomere length of mammalian chromosomal DNA; primers for use in said method; a kit comprising said primers; use of said method to diagnose or prognose or to determine the risk of developing a telomere shortening disease such as cancer, ageing, neurological disorders including Alzheimer's disease, Parkinson's disease and other dementias, brain infarction, heart disease, chronic HIV infection, chronic hepatitis, skin diseases, chronic inflammatory bowel disease including ulcerative colitis, anaemia, atherosclerosis, Barrett's oesophagus and cancers including pre-cancerous conditions, infertility, telomere syndromes including dyskeratosis congenita, aplastic anaemia, idiopathic pulmonary fibrosis, familial myelodysplastic syndrome-acute myeloid leukaemia, Hoyeraal-Hreiderasson syndrome, Revesz syndrome, Coats plus syndrome, bone marrow failure, and cryptogenic liver cirrhosis. Additionally, the invention also has application in assessing an individual's suitability to be a transplantation donor, for example a bone marrow donor.

BACKGROUND

Telomeres are nucleoprotein structures composed of repetitive DNA sequences (up to 25 kb of predominantly the tandem repeat sequence TTAGGG, termed the telomere repeat array) that cap the ends of linear eukaryotic chromosomes, protecting them from deterioration or fusion with adjacent chromosomes. In addition to TTAGGG repeats, the proximal 1-2 kb of human telomere repeat arrays also contain telomere variant repeats (TVRs) that include amongst others TCAGGG and TGAGGG (e.g. Baird et al EMBO 1995 and Letsolo et al NAR 2010). During DNA replication telomere sequences are lost from the chromosome ends. The enzyme telomerase compensates for this by synthesizing new telomere repeats but in somatic cells this enzyme is inactive and so, over time, the telomere shortens. Telomere ends are, however, maintained in certain cell types such as germ cells, stem cells and certain white blood cells, by telomerase catalysing the RNA templated addition of telomere repeats.

Telomere length is a key determinant of telomeric function and it has been shown that short dysfunctional telomeres can drive genomic instability and tumourigenesis in mouse models. Furthermore, deregulation of telomerase has been shown to drive oncogenesis. Additionally, the loss of telomeres in somatic cells has been linked to replicative senescence which typically would provide genomic stability preventing cancer. Conversely, it has also been shown that malignant cells can bypass this senescence and become immortalised by the aberrant activation of telomerase. Numerous diseases are known to exist as a consequence of genetic abnormalities and, specifically telomere shortening. These diseases include Alzheimer's disease, Parkinson's disease and other dementias, brain infarction, heart disease, chronic HIV infection, chronic hepatitis, skin diseases, chronic inflammatory bowel disease including ulcerative colitis, anaemia, atherosclerosis, Barrett's oesophagus and cancers including pre-cancerous conditions, infertility, telomere syndromes including dyskeratosis congenita, aplastic anaemia, idiopathic pulmonary fibrosis, familial myelodysplastic syndrome-acute myeloid leukaemia, Hoyeraal-Hreiderasson syndrome, Revesz syndrome, Coats plus syndrome, bone marrow failure, and cryptogenic liver cirrhosis. Additionally, a determination of telomere length has application in assessing an individual's suitability to be a transplantation donor, for example a bone marrow donor.

Consistent with the role of telomere biology in tumour progression, there is now a substantial body of evidence indicating that telomere length can provide prognostic information in many human malignancies including chronic lymphoid leukemia (CLL). However, there is a lack of resolution in the currently available technologies for detecting telomere length and this has hampered progress in translating telomeric assays into clinical practice. For example, a putative role of telomere dysfunction during the progression of breast cancer has been shown, and low-resolution telomere length analysis has been shown to provide limited prognostic information. A key problem with these technologies is that they are based on hybridisation of DNA probes to telomere repeat units. Consequently, as telomeres get shorter there is less probe target, and this means the shortened telomeres are not detectable. This is significant because it is the shortened telomeres that become dysfunctional and are subject to fusion, causing the genomic instability that can drive the progression of human cancers. Q-PCR-based methods have also been described for the estimation of telomere repeat content (WO 2004068110US). These methods allow for high throughput analysis however their linearity for the detection of short telomeres (<4 kb) has not been established[18]. This, coupled with the reported high co-efficient of variance (CV) values of up to 28%, renders Q-PCR methods inappropriate for the detection of short telomeres and so unreliable as a prognostic tool for clinical decision making[19]. In summary, hitherto, telomere analysis using existing low-resolution techniques is not a sufficiently informative prognostic tool.

To address this problem, we have previously developed single-molecule technologies that allow us to detect the presence of critically shortened telomeres[20,21] and to characterise telomere end-end fusions[16,17]. Single telomere length analysis (STELA) allows complete resolution of telomere lengths at specific chromosome ends, including telomere lengths at which telomere end-end fusions can occur[16,20]. It therefore permits detection of short telomeres that are potentially dysfunctional and capable of fusion; these telomeres cannot reliably be detected with any other method.

Using STELA and telomere fusion analysis[22,23] we have defined the length of telomeres in tumour cells at which telomere fusion can be detected[24,25]. We have used STELA together with a fusogenic threshold to stratify patients with CLL based on telomere length. These data show that telomere lengths below the fusogenic threshold are highly prognostic and that the mean of the fusogenic range (2.26 kb) provides an optimum prognostic resolution. Telomere length below the fusion threshold was the most powerful predictor of survival in CLL and this was particularly prognostic in early-stage patients[24]. Telomere dysfunction has been implicated in the progression of many tumour types and we have now established that the same thresholds are prognostic in breast cancer and myelodysplastic syndromes. We therefore consider that our threshold may provide clinical utility in many different tumour types.

Given the prognostic significance of our findings, we sort to establish robust high throughput methods, to determine telomere lengths. The complexity of the original STELA method makes it labour intensive and time consuming. Furthermore it utilises Southern hybridisation with radioactively labelled DNA probes, which render the method low throughput. The original STELA method is therefore most suitable for the research laboratory environment where low throughput, but high resolution, is required. However it is not suited for routine high throughput assessment of cancer patients.

To resolve these issues we herein disclose a novel variation of the STELA method—High Throughput STELA (HT-STELA). Like the original STELA method, HT-STELA is a PCR based technique that requires a linker oligonucleotide and amplifies specific human telomeres. However, it differs in that the resolution and detection of telomere length distributions is not achieved through gel electrophoresis and Southern hybridisation. Instead, the PCR products generated during the STELA PCR are resolved via capillary electrophoresis (using a FRAGMENT ANALYZER™ capillary electrophoresis system; Agilent) and detected by a camera that monitors the incorporation of a fluorescent intercalating dye into the PCR product. This altered resolution and detection step significantly decreases the amount of time taken to generate a telomere length measurement. However, the use of these different resolution and detection techniques require process modification if they are to work with the requisite sensitivity needed to reliably measure telomere length, thus, a number of steps have been devised to ensure the sensitivity of the method.

SUMMARY

According to a first aspect of the invention there is provided a high throughput method for determining telomere length of mammalian chromosomal DNA comprising:
i) annealing a primer sequence to a region adjacent a telomere repeat array of chromosomal DNA wherein said region is between 3843 bp-30 bp from said telomere repeat array;
ii) PCR amplifying 20 ng-35 ng of said chromosomal DNA using 21-23 cycles to generate an amplification product; and
iii) detecting the length of the amplification product.

As mentioned, the telomere is a region of repetitive nucleotide sequences predominantly composed of $(TTAGGG)_n$ at each end of a chromosome, thus reference to a region 3843 bp-30 bp from said telomere repeat array is reference to a region upstream from the start of the array (characterized predominantly by TTAGGG repeats) that caps the chromosome end.

Surprisingly, we have discovered that the method works most effectively if the method produces, for analysis, a telomere length distribution 'smear' as opposed to a banding pattern. Through subsequent deduction we have established that there are a number of reasons why a telomere length distribution smear is beneficial: it allows a more rapid analysis of mean telomere length as it requires less human intervention in the analyses of data within the software; it requires less reactions per sample; it increases the total amount of product and it ensures that non-specific background bands present are not incorporated into the sizing analysis. To achieve this telomere length distribution 'smear' we have discovered that we need to use an optimum amount of DNA and an optimum number of PCR cycles. With these two parameters defined we find we can reliably produce a telomere length distribution 'smear' for subsequent analysis. A typical telomere length distribution band is shown in FIG. 1a, in contrast a typical telomere length distribution smear is shown in FIG. 4.

Moreover, we have come to realize that these optimized parameters are consistent with specific amplification of the telomere length distributions that are representative of telomere shortening. Thus the selection of an optimised cycle number and amount of DNA provides a better representation of the telomere length distributions. Indeed, an optimised PCR cycle number results in less artefactual amplification, less heterogeneity and so a more accurate representation of the telomere length distribution.

Using a fluorescent signal or label which intercalates into the PCR amplification product we have discovered that PCR cycle numbers 21 and 23 produce a robust signal (between 27-65 RFU) and a reliable estimation of telomere length (FIG. 11) in a system where the lowest signal to provide a reliable telomere length estimate was 25 RFUs or 25% (Tel Peak area LM peak area, where Tel Peak area is the area under the curve of the telomere-specific products, and the LM area is the area under the curve for the lower marker). Both are determined using the PROSIZE™Data Analysis software (Agilent). Most ideally, PCR cycle number of 23 is used.

In yet a further preferred method of the invention the amount of chromosomal DNA used for PCR amplification is between 25-30 ng.

More ideally the amount of chromosomal DNA used for PCR amplification is selected from the group comprising: 25 ng, 26 ng, 27 ng, 28 ng, 29 ng and 30 ng. Most ideally, 25 ng of chromosomal DNA are used and 22 PCR cycles are executed to provide the amplification product. More preferably still, 30 ng of chromosomal DNA was subjected to 23 PCR cycles.

In yet a further preferred method of the invention said primer is provided at a concentration of 0.1, 0.2, 0.3, 0.4, 0.5, 0.6, 0.7 or 0.8 µM, but most ideally at 0.1 or 0.2 µM.

In yet a further preferred method of the invention, said chromosomal DNA is extracted from at least one cell, and ideally a plurality of cells, using an automated extraction method with a view to providing an equal amount of DNA into the PCR reaction each time the reaction is undertaken. An example of a suitable DNA extraction system is the Promega DNA IQ™ system. Using this system, DNA was extracted from cell suspensions and subsequently diluted to the single molecule level to provide an equal number of amplifiable molecules with the original STELA method. We then further optimized the method to ensure the production of a telomere length distribution smear for use in HT-STELA, this was done by determining the optimal elution volumes from the Promega DNA IQ™ system and subsequent volume of DNA solution added to the HT-STELA reactions. It was found that this provided a reliable telomere length distribution smear without the need to quantify input DNA. This increases the speed and reliability of the STELA process and allows for automation of DNA extraction, dilution and PCR setup. It also increases the ranges of samples that can be analysed, allowing for example, the use of FTA DNA cards with fingersticks or buccal swabs. Advantageously, this technology also allows individuals to provide the samples at home and send them in the standard post for telomere testing.

For the routine assessment of samples from patients, the isolation of cells to be tested (e.g. CD19+ CLL) and the subsequent extraction of DNA from these cells, HT-STELA PCR, resolution and detection of generated PCR products and the measurement of mean telomere length (e.g. using XpYp chromosome) from these products could all be achieved within one working day: whereas with the original STELA method this would have taken 7 working days to achieve. Thus HT-STELA provides a powerful tool allowing a rapid, accurate prognostic evaluation of cancer patients.

In a preferred embodiment of the method, said cell can be extracted from any biological sample. Reference herein to biological sample refers to any sample, or processed derivative thereof, taken from a subject whose telomere length is to be analysed. This includes but is not limited to complex samples, such as whole blood, tissue samples or tumour samples, or purified cell samples thereof.

Alternatively, a processed derivative of a biological sample may be used such as, but not limited to, cells harvested previously isolated and extracted from a biological sample and, if necessary, re-suspended in an appropriate medium. For example, FTA cards are a commonly used format for the convenient sampling and storage of blood samples for subsequent downstream DNA analysis. It provides a quick method for patients that may require a telomere test, to provide a sample at home, without the requirement of a clinician or phlebotomist. A small blood sample is spotted onto an FTA card then returned to the testing facility by standard mail services.

In a preferred embodiment of the invention, the DNA IQ system appears to be saturated at $4 \times 10^5$ cells and so the preferred method involves the use of between $2 \times 10^5$ and $6 \times 10^5$ and preferably $4 \times 10^5$ cells.

It has been found that occasionally telomere lengths can display considerable heterogeneity, for example in samples derived from peripheral blood of normal individuals, which can lead to unfavourable PCR amplification products. In these circumstances, it has been found that pre-digesting the chromosomal DNA prior to performing HT-STELA reduces the complexity of sample DNA providing a simpler target for amplification.

Therefore, in a further preferred embodiment of the invention said chromosomal DNA is digested with a restriction endonuclease that cleaves non-telomeric DNA. As will be appreciated by those skilled in the art, any enzyme that cleaves the DNA phosphodiester bond within the polynucleotide chain can be used provided it does not cleave within the telomere to be amplified.

However, given that we are assessing telomere length it is advisable to use a restriction endonuclease that does not cleave the telomeric region and so, more ideally, said restriction enzyme is selected on the basis it does not cleave between the 5' end of said primer and the telomere repeat array or chromosome telomere end.

In yet a further preferred embodiment of the invention said detecting the length of the amplified product involves the use of markers: a lower marker that was larger than the size of the larger primer complexes and primer-dimers (200 bp) but smaller than the smallest fragment size of a telomere generated with HT-STELA (such as 882 bp or 415 bp); and an upper marker that was larger than the longest mean telomere length observed in our cohorts of CLL. Thus, ideally, a lower marker less than 882 bp or 415 bp was chosen. Ideally, the marker is selected from the group comprising: 882 bp, 881 bp, 880 bp, 879 bp, 878 bp, 877 bp, 876 bp, 875 bp, 874 bp, 873 bp, 872 bp, 871 bp, 870 bp, 410 bp, 409 bp, 408 bp, 407 bp, 406 bp, 405 bp, 404 bp, 403 bp, 402 bp, 401 bp, 400 bp, 399 bp, 398 bp, 397 bp, 396 bp, 395 bp, 394 bp, 393 bp, 392 bp, 391 bp, and 390 bp. Ideally, a commercially available 400 bp DNA fragment was obtained for this purpose (NoLimits, Thermo Scientific). Similarly, an upper marker greater than 10 kb was chosen such as a marker selected form the group comprising: 11 kb, 12 kb, 13 kb, 14 kb, 15 kb, 16 kb, 17 kb, 18 kb, 19 kb and 20 kb, including all 0.1 kb integers therebetween.

In yet a further preferred method of the invention to achieve specificity for a particular chromosome, primers are designed to anneal with a region adjacent a telomere repeat array of chromosomal DNA of chromosomes XpYp, 7q, 12q and 17p. More ideally still, telomere-adjacent primers are designed incorporating telomere specific nucleotides at the 3' end.

Preferably, the 7q chromosome primers are designed around i.e. to be complementary to the 7q-specific nucleotides (with respect to the beginning of the telomere repeat array, or hg38 human genome reference sequence) 1115T (chr7:159334755 hg38), 551A (chr7:159335319 hg38), 195G (chr7:159335675 hg38) and, to a lesser extent, 29G (chr7:159335841 hg38). These primers produced robust telomere length distribution smears.

Preferably, the 12q chromosome primers are designed around i.e. to be complementary to the 12q specific nucleotides (with respect to the beginning of the telomere repeat array, or hg38 human genome reference sequence) 350G (chr12:133264524 hg38) and 550T (chr12:133264324 hg38). These primers generated robust telomere length distribution smears.

Preferably, the XpYp chromosome primers are designed around i.e. to be complementary to the XpYp specific nucleotides (with respect to the beginning of the telomere repeat array, or hg38 human genome reference sequence) 397C (XpYpE5)(chrX:10432 hg38) and 861C (XpYpC) (chrX:10896 hg38). These primers generated robust telomere length distribution smears.

Preferably, the 17p chromosome primers are designed around i.e. to be complementary to the 17p specific nucleotides 292C (17pseq1rev), 1018T (17pseq2rev), 1837C (17pseq4rev), 2559C (17p2) and 3018G (17p7) (with respect to the beginning of the telomere repeat array). These primers generated robust telomere length distribution smears.

Preferably, primers designed to amplify other chromosomal telomeres, including 2p, 4q, 4p, 5p, 11q, 16p and 18q, that also generate telomere-specific products with the orginal STELA method, may also provide utility with HT-STELA. These primers include: 2p2 (chr2: 10755 hg38), 4qK1 (chr4:190122098 hg38), 4p4 (chr4:10457 hg38), 5p3 (chr5:12240 hg38), 11q13B (chr11:135076467 hg38), 16prev1 (chr16:10241 hg38) and 18qrev4M (chr18: 80262147 hg38).

In fact, we have found that primers that anneal up to at least 3.843 kb from the start of the telomere repeat array yield robust telomere profiles. However, it was also apparent that primers that anneal within 30 bp of the telomere repeat array did not produce efficient or specific amplification. Accordingly, when working the invention we use primers that anneal to a region of the chromosome that is between 3843 bp-30 bp from the start of the telomere repeats TTAGGG.

As used herein, the term "primer(s)" describes an oligonucleotide that hybridizes under physiological or reaction conditions (see HT-STELA PCR, page 20) to end chromosome DNA. Those skilled in the art will recognize that the exact length of the oligonucleotide and its degree of complementarity with its target will depend upon the specific target selected, including the sequence of the target and the particular bases which comprise that sequence, notwithstanding the fact that ideally the oligonucleotide primers are designed to be complementary to at least one and ideally a plurality of said chromosome end specific nucleotides.

It is preferred that the oligonucleotide be constructed and arranged so as to bind selectively with the target under physiological/reaction conditions, i.e., to hybridize substantially more to the target sequence than to any other sequence in the target cell under physiological/reaction conditions.

In order to be sufficiently selective and potent the oligonucleotides should comprise at least $7^{26}$ and more preferably, at least 15 consecutive bases which are complementary to the target. Most preferably, the oligonucleotides comprise a complementary sequence of 20-30 bases.

In yet a further preferred embodiment of the invention detecting said amplification product(s) involves a resolution (or separation) process using capillary electrophoresis, an example of a suitable apparatus for undertaking this work is the FRAGMENT ANALYZER™ capillary electrophoresis system (available from Agilent). Other capillary gel systems are available from Lifetechnologies. Moreover, once the amplification product(s) have been separated using capillary electrophoresis it/they is/are detected using an appropriate signal or label and we prefer to use a fluorescent dye, ideally one that intercalates into the amplification product. Using the method of the invention we have discovered that a fluorescent signal or label which intercalates into the PCR amplification product and produces a signal between 27-65 RFU, ideally at least 25 RFU, is robust and reliable enough for an estimation of telomere length (FIG. 11) in a system where the lowest signal to provide a reliable telomere length estimate was 25 RFUs, this equates to, or can be expressed as 25% of (the area under the curve for the HT-STELA signal divided by the area under the curve for lower marker as shown in FIG. 11 i.e. Tel Peak area/LM peak area). Please see page 35, Quality Control.

In yet a further embodiment of the invention said method is undertaken to diagnose or prognose or to determine the risk of developing a condition selected from the group comprising: cancer, ageing, neurological disorders including Alzheimer's disease, Parkinson's disease and other dementias, brain infarction, heart disease, chronic HIV infection, chronic hepatitis, skin diseases, chronic inflammatory bowel disease including ulcerative colitis, anaemia, atherosclerosis, Barrett's oesophagus and cancers including pre-cancerous conditions, infertility, telomere syndromes including dyskeratosis congenita, aplastic anaemia, idiopathic pulmonary fibrosis, familial myelodysplastic syndrome-acute myeloid leukaemia, Hoyeraal-Hreiderasson syndrome, Revesz syndrome, Coats plus syndrome, bone marrow failure, and cryptogenic liver cirrhosis.

In yet a further embodiment of the invention said method is undertaken to assess an individual's suitability to be a transplantation donor, for example a bone marrow donor.

According to a further aspect of the invention there is provided a kit for determining telomere length of mammalian chromosomal DNA comprising:
at least one oligonucleotide primer able to anneal to a region adjacent a telomere repeat array of chromosomal DNA wherein said region is between 3843 bp-30 bp from said telomere repeat array.

In a preferred kit of the invention a plurality of primers are provided and ideally said primers are able to anneal to at least said region in one of the following chromosomes 7q, 12q, 17p, XpYp, 2p, 4q, 4p, 5p, 11q, 16p and 18q.

More preferably still, said kit comprises reagents for carrying out said method.

In yet a further aspect of the invention there is provided a primer selected from the group comprising:

| Chromosome end | Primer name | Genomic Coordinates (HG38) | Sequence |
|---|---|---|---|
| 2p | 2p2 | chr2: 10755 | GAGCTGCGTTTTGCTGAGCAC (SEQ ID NO: 1) |
| 4q | 4qK1 | chr4: 190122098 | ACGGTGGCATGCCTCTCTC (SEQ ID NO: 2) |
| 4p | 4p4 | chr4: 10457 | TCTGCGCCTGCGATGGCGCTATG (SEQ ID NO: 3) |
| 5p | 5p3 | chr5: 12240 | GCATTCTCTTCACCACAGATGTTG (SEQ ID NO: 4) |
| 7q | 7q1533C | chr7: 159334337 | CCCACACAGTCATCTATTGTT (SEQ ID NO: 5) |
| | 7q1115T | chr7: 159334755 | GAGGTGCAGTAGTGGGGATCTAACT (SEQ ID NO: 6) |
| | 7q843T | chr7: 159335027 | GGGACAGCATATTCTGGTTT (SEQ ID NO: 7) |
| | 7q551A | chr7: 159335319 | GCACAGCCTTTTGGGGTACCA (SEQ ID NO: 8) |
| | 7q195G | chr7: 159335675 | AGTGGGAGATCCACACCGTAGCGTG (SEQ ID NO: 9) |
| | 7q29G | chr7: 159335841 | CCaTGCAGTGCTAAGACAGCAATGAG (SEQ ID NO: 10) |
| 11q | 11q13B | chr11: 135076467 | CAGACCTTGGAGGCACGGCCTTCG (SEQ ID NO: 11) |
| 12q | 12q1511C | chr12: 133263363 | CCTCTGGTCATTATGAATAGGGCTTC (SEQ ID NO: 12) |
| | 12q1387G | chr12: 133263487 | GGGGAAAAAATGCCCAAG (SEQ ID NO: 13) |
| | 12q1036C | chr12: 133263838 | CCTTCTCTTCTTGATGTC (SEQ ID NO: 14) |
| | 12q550T | chr12: 133264324 | ACAGCCTTTTGGGGTACCGT (SEQ ID NO: 15) |
| | 12q350G | chr12: 133264524 | GGCTTCATTGATGGTGAATACAATCG (SEQ ID NO: 16) |
| | 12q319G | chr12: 133264555 | GCAGCGCTGAATATTCAGGGTG (SEQ ID NO: 17) |
| 16p | 16prev1 | chr16: 10241 | CACTTATTAGTTCCAGTCTCTG (SEQ ID NO: 18) |
| 17p | 17p8 | | AGAAGCAGCGAGGAGCTTCA (SEQ ID NO: 19) |
| | 17p7 | | CCTGGCATGGTATTGACATG (SEQ ID NO: 20) |
| | 17p2 | | GCTAGGAATGGAATCATTGACTC (SEQ ID NO: 21) |
| | 17pseq4rev | | GATACTGGGAGGATCATATCTGGC (SEQ ID NO: 22) |
| | 17pseq2rev | | CCATTAGCCTGTGGGGTCTGAT (SEQ ID NO: 23) |
| | 17pseq1rev | | GAATCCACGGATTGCTTTGTGTAC (SEQ ID NO: 24) |
| | 17pseq1B | | AAGCAGGTTGAGAGGCTGAGG (SEQ ID NO: 25) |
| 18q | 18qrev4M | chr18: 80262147 | CACAGGGATGGTTAGGTATCTC (SEQ ID NO: 26) |

-continued

| Chromosome end | Primer name | Genomic Coordinates (HG38) | Sequence |
|---|---|---|---|
| XpYp | XpYpB | chrX: 12573 hg38 | CGAGCAAGCATCGGAACGTGACT (SEQ ID NO: 27) |
|  | XpYpM | chrX: 11688 | ACCAGGTTTTCCAGTGTGTT (SEQ ID NO: 28) |
|  | XpYpO | chrX: 11660 | CCTGTAACGCTGTTAGGTAC (SEQ ID NO: 29) |
|  | XpYpC | chrX: 10896 | CAGGGACCGGGACAAATAGAC (SEQ ID NO: 30) |
|  | XpYpP | chrX: 10575 | ACCAGGGGCTGATGTAACG (SEQ ID NO: 31) |
|  | XpYpE2 | chrX: 10427 | TGTCTCAGGGTCCTAGTG (SEQ ID NO: 32) |
|  | XpYpE3 | chrX: 10425 | TCTCAGGGTCCTAGTGTG (SEQ ID NO: 33) |
|  | XpYpE4 | chrX: 10429 | GTTGTCTCAGGGTCCTAG (SEQ ID NO: 34) |
|  | XpYpE5 | chrX: 10432 | GGGGTTGTCTCAGGGTCC (SEQ ID NO: 35) |
|  | XpYpE6 | chrX: 10437 | TTCTAGGGGTTGTCTCAG (SEQ ID NO: 36) |
|  | XpYpE7 | chrX: 10439 | TCTTCTAGGGGTTGTCTC (SEQ ID NO: 37) |
|  | XpYpJ | chrX: 10064 | CTAATCTGCTCCCWCCCAC (SEQ ID NO: 38) |

In the claims which follow and in the preceding description of the invention, except where the context requires otherwise due to express language or necessary implication, the word "comprises", or variations such as "comprises" or "comprising" is used in an inclusive sense i.e. to specify the presence of the stated features but not to preclude the presence or addition of further features in various embodiments of the invention.

All references, including any patent or patent application, cited in this specification are hereby incorporated by reference. No admission is made that any reference constitutes prior art. Further, no admission is made that any of the prior art constitutes part of the common general knowledge in the art.

Preferred features of each aspect of the invention may be as described in connection with any of the other aspects.

Other features of the present invention will become apparent from the following examples. Generally speaking, the invention extends to any novel one, or any novel combination, of the features disclosed in this specification (including the accompanying claims and drawings). Thus, features, integers, characteristics, compounds or chemical moieties described in conjunction with a particular aspect, embodiment or example of the invention are to be understood to be applicable to any other aspect, embodiment or example described herein, unless incompatible therewith.

Moreover, unless stated otherwise, any feature disclosed herein may be replaced by an alternative feature serving the same or a similar purpose.

BRIEF DESCRIPTION OF THE DRAWINGS

The invention will now be described by way of example only with reference to the following tables and figures:

FIG. 1. The electrophoresis and detection of PCR products generated by STELA on the FRAGMENT ANALYZER™ capillary electrophoresis system. 250 pg HT1080 cl.2 DNA was added to 30 µl STELA PCR reactions and cycled for 22 PCR cycles with an annealing temperature of 65° C. (a) 4 µl from each reaction was subsequently taken and analysed by the STELA protocol. (b) (i) The remainder of the STELA PCR product was electrophoresed and detected using the FRAGMENT ANALYZER™ capillary electrophoresis system along with a positive control PCR from which PCR products can be detected. (ii) Example of an electropherogram generated from one capillary through which one of the PCR reactions was resolved LM=lower marker, UM=upper marker.

FIG. 8. Improving the visibility of the lower marker for optimal capillary-to-capillary normalisation (a) Example of an electropherogram of HT-STELA PCR products which have not been purified resolved within a single capillary along with 0.5 ng/µl lower (75 bp) and upper (20 kb) markers provided within the DNF-930 dsDNA reagent kit (Advanced Analytical). 'UM' indicates the location of the upper marker however the presence of PCR artefacts less than 200 bp masks the position of the 75 bp lower marker 'LM'. (b) Electropherogram showing the same as (a) but after PCR purification of HT-STELA PCR products. (c) Electropherogram of resolved HT-STELA PCR products within a capillary along with new 400 bp and 15 kb NoLimits DNA fragments (0.5 ng/µl). The new 400 bp lower marker results in a single clear peak separate from the unwanted PCR artefacts.

FIG. 19. Optimisation of the DNA IQ system to clean up and normalize DNA input samples to achieve HT-STELA telomere length distribution smears with consistent intensity. 200, 500, 1000 and 2000 ng HT1080 cl.2 DNA was added to DNA IQ casework pro kit cartridges (CW) or DNA IQ reference sample cartridges (RS). DNA was eluted into either 50 ul (CW) or 300 ul (RS). For the CW purified samples either 3, 6 or 9 ul eluted DNA was added to individual HT-STELA reactions. For the RS purified samples 3, 10 or 20 ul eluted DNA was added to each HT-STELA reaction. HT-STELA reactions were then subject to 23 PCR cycles and generated PCR product was resolved and detected on the FRAGMENT ANALYZER™ capillary electrophoresis system. DNA concentration was measured in triplicate with picogreen using the nanodrop 3300 fluorospectrometer. (Tel peak area/LM peak area) %=(area under a telomere length distribution smear peak on an electropherogram/peak area under lower marker peak on electropherogram)*100. Mean telomere length (MTL) was calculated for each HT-STELA reaction triplicate using the smear analysis tool within the PROSIZE™Data Analysis software.

Figure 2B:
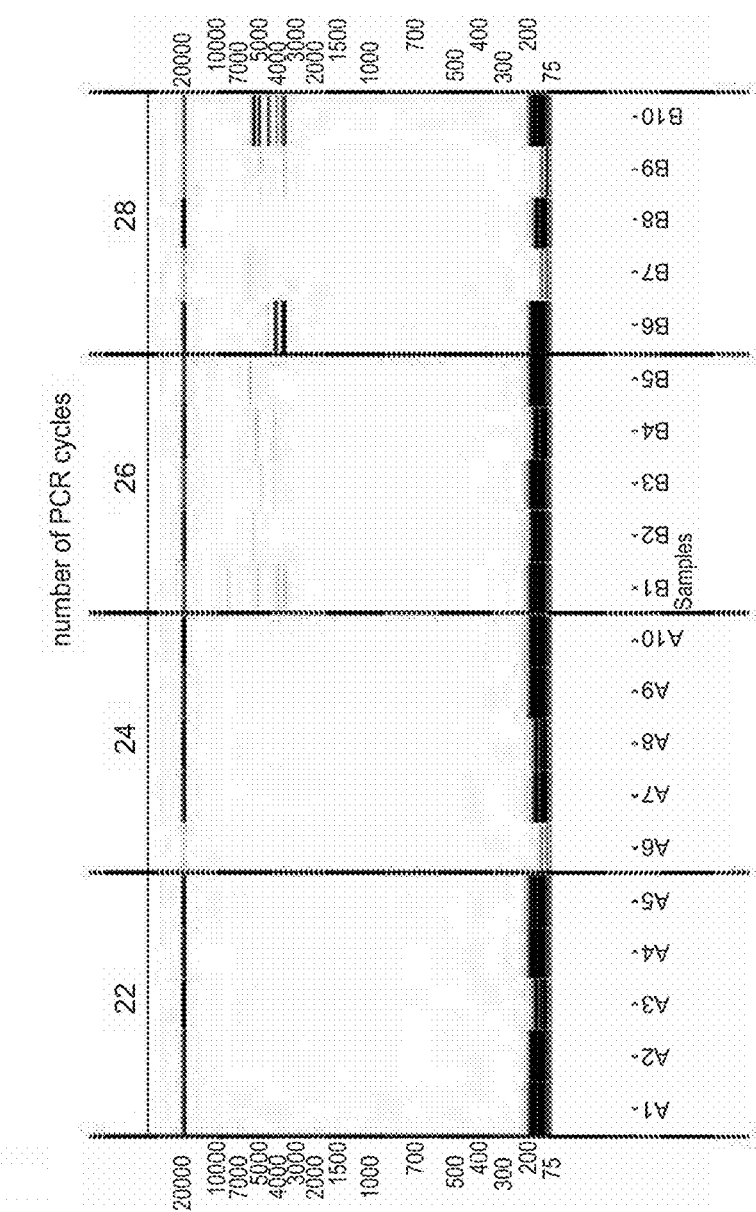
FIG. 2. Increased number of PCR cycles increases the amount of HT-STELA PCR product generated to allow their visualisation on the FRAGMENT ANALYZER™ capillary electrophoresis system. 250 pg MRC5 cl.13 DNA was added to 30 µl STELA PCR reactions and subject to 22, 24, 26 or 28 PCR cycles with an annealing temperature of 65° C. 4 µl PCR products generated were taken for (a) conventional STELA analysis and the remaining 26 µl was loaded onto a 96 well plate for capillary electrophoresis and detection (b).

Table-1. List of oligonucleotides.

Table-2. Coefficient of variation analysis for HT-STELA. 30 ng MRC5 cl.5 DNA was added to 95 HT-STELA PCR reactions and subject to 23 PCR cycles. The resulting PCR products were electrophoresed and detected on the FRAGMENT ANALYZER™ capillary electrophoresis system on three independent occasions. Mean XpYp telomere length was measured for lower and upper allele after each allele. For each of the 95 PCR reactions the variation between the mean XpYp telomere length measurement after each assay was determined using the formula % CV=SD/average MTL. This was performed for both the lower and upper allele.

DETAILED DESCRIPTION

Materials and Methods
Oligonucleotides

Oligonucleotides were designed based on human DNA sequences obtained from H. Reithman at the Wistar institute (www.wistar.upenn.edu/Reithman) and National Centre for Biotechnology Information (NCBI). The oligonucleotides were synthesised by MWG-Biotech AG (Ebersberg, Germany). All primers used during this study are listed in table 1.

CLL Cell Isolation

CD19+ CLL cells were isolated using MACS whole blood CD19 microbeads. A volume of whole blood containing $2 \times 10^6$ white blood cells was taken and brought up to 1000 ul with 1×PBS. 20 ul MACS whole blood microbeads were then added before mixing thoroughly and incubating at room temperature for 15 minutes. After incubation blood samples were loaded onto AutoMACS Pro separator (Miltenyi Biotech) and CD19+ cells were positively selected using the posselwb program.

DNA Extraction
Maxwell

Genomic DNA was extracted from cell pellets using the Maxwell 16 LEV DNA-la DNA kit (Promega) along with the Maxwell 16 instrument. Cell lysis was achieved through incubation of the cell pellet with 400 µl lysis buffer and 10 µl proteinase K at 56° C. for at least one hour. Cell lysates were then loaded into the cartridges and placed in the Maxwell 16 instrument. The forensic mode with LEV hardware was ran to extract DNA from the cell lysates. Extracted DNA was eluted into 40 µl elution buffer.

Phenol/Chloroform

Genomic DNA from cell pellets containing over 3×106 cells was extracted by standard phenol/chloroform extraction (Sambrook et al., 1989). Briefly, cells were lysed overnight at 45° C. in 300-500 µl lysis buffer (10 mM Tris-Hcl pH8, 100 mM NaCl, 5 mM EDTA pH8, 0.5% SDS) containing 30 µg RNase A (Sigma; stock 10 mg/ml) and 60 µg proteinase K (Sigma; stock 20 mg/ml). After brief centrifugation 300-500 µl phenol/chloroform was added to the cell lysate and rotated for 20 mins at room temperature. The mixture was centrifuged at 13000 rpm for 5 mins to separate the phases, the aqueous and interphase phases were removed and added to an eppendorf containing 300 µl phenol/chloroform. This was rotated again for 20 mins and then centrifuged (13000 rpm) for 5 minutes. The aqueous phase was removed and to this was added 30 µl 3M sodium acetate pH5.3 (Sigma) and 900 µl ice-cold 100% ethanol to precipitate the DNA. The mix was left at –20° C. for at least an hour. After brief centrifugation (13000 rpm, 1 min) the DNA pellet was washed in 70% ice-cold ethanol and air dried in the micro-flow hood. DNA was then resuspended in 10 mM Tris-Hcl pH8.

DNA Quantification

DNA concentrations were determined in triplicate either by Hoechst 33258 flurometry as described previously (Baird et al., 2003) or using a Nanodrop 3300 fluorospectrometer (Thermo scientific). Briefly an equal amount of a 2× dilution of Quant-iT Picogreen dsDNA reagent (Life Technologies) and DNA were mixed and incubated at room temperature for 5 minutes. 2 ul was loaded onto the pedestal to measure the fluorescence. The fluorescence measurement was then converted to DNA concentration using a standard curve constructed using DNA of known quantity.

STELA PCR

DNA was diluted to 250 µg/µl in 10 mM Tri-Hcl (pH 8) containing 250 µM Tel2 linker. Multiple 10 µl reactions were set up per sample (typically 6) each containing 1× Taq buffer (75 mM Tris-HCl (pH8.8), 20 mM (NH4)SO4, 0.01% Tween-20) (Abgene), 2 mM MgCl2, 1.2 mM dNTPs, telomere-specific primer (0.5 µM), teltail primer (0.5 µM), and 1 U Taq/PWO (Abgene/Roche) at a ratio of 10:1. 1 µl DNA/tel2 mix (250 µg) was added to each reaction. These reactions were then cycled in a DNA ENGINE TETRAD® Thermal Cycler (Bio-Rad) using the following conditions: 94° C. (20 sec), 65° C. (30 sec), 68° C. (8 mins) for 22 cycles.

HT-STELA PCR

DNA was diluted to 10 ng/µl in 10 mM Tris-Hcl (pH8) containing 250 µM Tel2 linker. Multiple 30 ul reactions were set up per sample (typically 3-5) each containing 1× Taq buffer (75 mM Tris-HCl (pH8.8), 20 mM (NH4)SO4, 0.01%

Tween-20) (Abgene), 2 mM MgCl2, 1.2 mM dNTPs, telomere-specific primer (0.2 µM), teltail primer (0.2 µM), and 1 U Taq/PWO (Abgene/Roche) at a ratio of 10:1. 3 µl DNA/tel2 mix (30 ng) was added to each reaction. These reactions were then cycled in a DNA ENGINE TETRAD® Thermal Cycler (Bio-Rad) using the following conditions: 94° C. (20 sec), 65° C. (30 sec), 68° C. (5 mins) for 23 cycles Gel Electrophoresis DNA fragments were resolved using a 40 cm long, 0.5% Tris-acetate-EDTA agarose gel submerged in 1×TAE cooled to 4° C. by a circulating cooling system. 4 ul STELA PCR reactions containing 1× ficol-based loading dye (5% bromophenol blue, 5% xylene, 15% ficol) were loaded in the gel and ran through the length of the gel at 120V for 16 hours.

Capillary Electrophoresis 30 ul HT-STELA PCR reactions were loaded onto a 96 well plate (sample plate) along with a 75 bp-15 kb ladder in one well. Another 96 well plate (marker plate) was loaded which contained 22 ul of the combined lower (400 bp) and upper (15 kb) markers in every well. Both plates were placed into FRAGMENT ANALYZER™ capillary electrophoresis system along with a deep well 96 well plate containing 1.1 ml 1× inlet buffer. Both marker DNA fragments and HT-STELA PCR fragments were then resolved through DNF-930 dsDNA gel containing 0.001× intercalating gel using the following conditions: prerun (6 kV, 30 seconds), marker injection (1 kV, 10 seconds), sample injection (4 kV, 50 seconds), separation 6 kV, 120 minutes).

Southern Blotting

The resolved STELA PCR products were depurinated by washing the gel twice in depurination buffer (0.25M HCl) for 6 minutes. After rinsing, the gel was then washed in denaturation buffer (1.5M NaCl/0.5MNaOH) for 15 minutes. The DNA was then transferred onto a positively charged membrane (Hybond XL, Amersham) by alkaline Southern blotting with denaturation buffer for 4-6 hours.

Probe Labelling and Hybridisation

Probe Synthesis 25 ng probe DNA and ladder (1:1 of 1 kb:2.5 kb) in TE buffer (10 mM Tric-Hcl and 1 mM EDTA) was labelled using Ready-To-Go DNA labelling beads (GE Healthcare). This kit generates labelled probes using random hexaprime labelling with [α-33P] dCTP.

Hybridisation

After blotting the membranes were rinsed in H2O before undergoing pre-hybridization for 15 mins in church buffer (0.5M sodium phosphate buffer (1M disodium hydrogen phosphate and 1M sodium dihydrogen phosphate), 1 mM EDTA, 1% BSA, 7% SDS, pH 7.2). 25 µl of radioactively labelled probe was added to the hybridisation bottles which were then left to hybridize at 60° C. overnight.

Removing Unbound Probe

To remove unbound probes the membrane was washed with 0.1× sodium chloride sodium citrate (SSC)/0.1% sodium dodecyl sulphate (SDS) several times at 60° C. The washed blots were then dried in the hybridization oven at 60° C. for ~30 mins.

Visualisation of Radiolabelled Blots

Radiolabelled southern blots were placed in a cassette with a phosphoimager screen (Amersham) for 24 hours. The phosphoimager screen was then scanned using the Typhoon 9410 biomolecular imager (GE healthcare).

DNA Template Digestion

Peripheral blood was obtained from healthy individuals using contact-activated lancets (BD). DNA was extracted directly from peripheral blood samples (300 µl) using DNA IQ casework pro kit cartridges and eluted into 50 µl elution buffer (Promega). Extracted DNA was digested using EcoR1. Briefly, 17.3 µl DNA was added to 20 µl reactions containing RE 1× buffer, acetylated BSA (1 ug/µl) and EcoR1 restriction enzyme (5 U). Reactions were then incubated at 37° C. for 2 hours followed by a 5 min incubation at 65° C. to heat inactivate the restriction enzyme. Following digestion was then quantified using NanoDrop 3300 fluorospectrophotometer (Thermo Scientific) and diluted to ~10 ng/ul.

HT-STELA 250 pM Tel2 linker was added to each digested DNA. Three 30 ul reactions were set up per sample each containing 1× Taq buffer (75 mM Tris-HCl (pH8.8), 20 mM (NH4)SO4, 0.01% Tween-20) (Abgene), 2 mM MgCl2, 1.2 mM dNTPs, XpYpC primer (0.2 µM), teltail primer (0.2 µM), and 1 U Taq/PWO (Abgene/Roche) at a ratio of 10:1. Either 2 µl or 3 µl DNA/tel2 mix was added to each reaction. These reactions were then cycled in a DNA ENGINE TETRAD® Thermal Cycler (Bio-Rad) using the following conditions: 94° C. (20 sec), 65° C. (30 sec), 68° C. (5 mins) for 21, 22 or 23 cycles.

Capillary Electrophoresis

30 µl HT-STELA PCR reactions were loaded onto a 96 well plate (sample plate) along with a 75 bp-15 kb ladder in one well. Another 96 well plate (marker plate) was loaded which contained 22 ul of combined lower (400 bp) and upper (15 or 20 kb) markers. Both plates were placed into the FRAGMENT ANALYZER™ capillary electrophoresis system along with a deep well 96 well plate containing 1.1 ml 1× inlet buffer. Both marker DNA fragments and HT-STELA PCR fragments were then resolved through DNF-930 dsDNA gel containing 0.001× intercalating gel using the following conditions: prerun (6 kV, 30 seconds), marker injection (1 kV, 10 seconds), sample injection (4 kV, 75 seconds), separation 6 kV, 120 minutes).

DNA Normalisation Using the DNA IQ System

Genomic DNA was added directly to 400 µl lysis buffer which was then loaded into DNA IQ casework pro kit cartridges or DNA IQ reference sample kit cartridges (Promega) and placed in the Maxwell 16 instrument. For the DNA IQ casework pro kit DNA was extracted using the forensic mode with low elution volume (LEV) hardware. DNA was eluted into 80 µl elution buffer. For the reference sample kit DNA was extracted using the forensic mode with the standard elution volume (SEV) hardware. For this kit extracted DNA was eluted into 300 µl elution buffer.

DNA Extraction from Dried Blood Spots

125 µl blood was pipetted onto an FTA card sample target and left to air-dry overnight. Two 3 mm punches were cut from each dried blood spot and incubated at 65° C. with shaking (1400 rpm) with 40 µl 10 mg/ml proteinase K and 360 µl casework extraction buffer (Promega). The eluted cell lysate was removed from the stripped FTA cardpunches by adding both the punches and supernatant to spin baskets (Promega) inserted into Eppendorf tubes that were centrifuged at 12000 rpm for two minutes. Cell lysates were then loaded into DNA IQ casework pro kit cartridges (Promega) and placed in the Maxwell 16 instrument. The forensic mode with LEV hardware was ran to extract DNA from the cell lysates. Extracted DNA was eluted into 50 µl elution buffer.

HT-STELA and FTA STELA

250 µM Tel2 linker was added to each extracted DNA. Three 30 µl reactions were set up per sample each containing 1× Taq buffer (75 mM Tris-HCl (pH8.8), 20 mM (NH4)SO4, 0.01% Tween-20) (Abgene), 2 mM MgCl2, 1.2 mM dNTPs, XpYpC primer (0.2 µM), teltail primer (0.2 µM), and 1 U Taq/PWO (Abgene/Roche) at a ratio of 10:1. 4 µl DNA/tel2 mix was added to each reaction. These reactions were then cycled in a DNA ENGINE TETRAD® Thermal Cycler (Bio-Rad) using the following conditions: 94° C. (20 sec), 65° C. (30 sec), 68° C. (5 mins) for 23 cycles.

Capillary Electrophoresis

30 µl HT-STELA PCR reactions were loaded onto a 96 well plate (sample plate) along with a 75 bp-15 kb ladder in one well. Another 96 well plate (marker plate) was loaded which contained 22 µl of the combined lower (400 bp) and upper (15 kb) markers in every well. Both plates were placed into FRAGMENT ANALYZER™ capillary electrophoresis system along with a deep well 96 well plate containing 1.1 ml 1× inlet buffer. Both marker DNA fragments and HT-STELA PCR fragments were then resolved through DNF-930 dsDNA gel containing 0.001× intercalating gel using the following conditions: prerun (6 kV, 30 seconds), marker injection (1 kV, 10 seconds), sample injection (4 kV, 75 seconds), separation 6 kV, 120 minutes).

Statistical Analysis

STELA Band Quantification

Gels scanned using the Typhoon 9410 were subsequently analysed using Molecular dynamics ImageQuant 5.0 (GE). The molecular weights of individual telomeres on each STELA Southern blot were calculated using Phoretix 1D software (Nonlinear dynamics). Mean telomere length measurements were then calculated.

HT-STELA—Data Interpretation and Statistical Analysis

The output data from the FRAGMENT ANALYZER™ capillary electrophoresis system was viewed in PROSIZE-™Data Analysis software. The following peak analysis settings were applied when analysing the data: peak width—50 seconds, minimum peak height—25 RFU with no valley to valley baseline. Baseline setpoints were determined manually for each sample. Mean telomere length was calculated using the smear analysis function within the PRO-SIZE™Data Analysis software. The smear range was manually set for each sample. The mean telomere length was calculated from the smear analysis result for all reactions within each sample reaction set.

Results

STELA Product Detection with a FRAGMENT ANA-LYZER™ Capillary Electrophoresis System STELA PCR was performed using DNA extracted from a clonal population of the HT1080 fibrosarcoma cell line (HT1080 cl.2). This DNA was used as it displays a homogenous telomere length profile at XpYp that is similar to what is observed in CLL patients. Based on the reaction conditions for the original STELA method for the XpYp telomere, 250 pg DNA was added to 30 µl STELA PCR reactions which were then subject to 22 PCR cycles using an annealing temperature of 65° C. 4 µl of each reaction was used for the standard STELA analysis and the remainder of the PCR products resolved and detected using the FRAGMENT ANALYZER™ capillary electrophoresis system (FIG. 1). With the original methodology the STELA PCR products are readily detected by the annealing of a radioactively labelled telomere repeat containing probe (FIG. 1a). However, as can be seen from the digital gel image generated with the PROSIZE™Data Analysis software, these same PCR products are not abundant enough to be to be detected fluorescently with the FRAGMENT ANALYZER™ capillary electrophoresis system (FIG. 1b(i)). An electropherogram of one of the capillaries through which the generated PCR products were electrophoresed further confirms the lack of any fluorescent signal generated from the STELA PCR products (FIG. 1b(ii)). The lower and upper markers are clearly visible as are large amounts of artefacts <200 bp formed in the STELA PCR. The STELA PCR conditions therefore required modification to ensure that telomere length distributions could be detected by capillary electrophoresis (using the FRAGMENT ANALYZER™ capillary electrophoresis system).

Improving Conditions to Detect STELA PCR Products Directly on the FRAGMENT ANALYZER™ Capillary Electrophoresis System As the original STELA conditions resulted in insufficient PCR product to be detected by the FRAGMENT ANA-LYZER™ capillary electrophoresis system, a number of factors were optimised to increase the amount of PCR product generated and hence increase the signal intensity measured by the system.

Increased Cycle Number

Figure 2A:
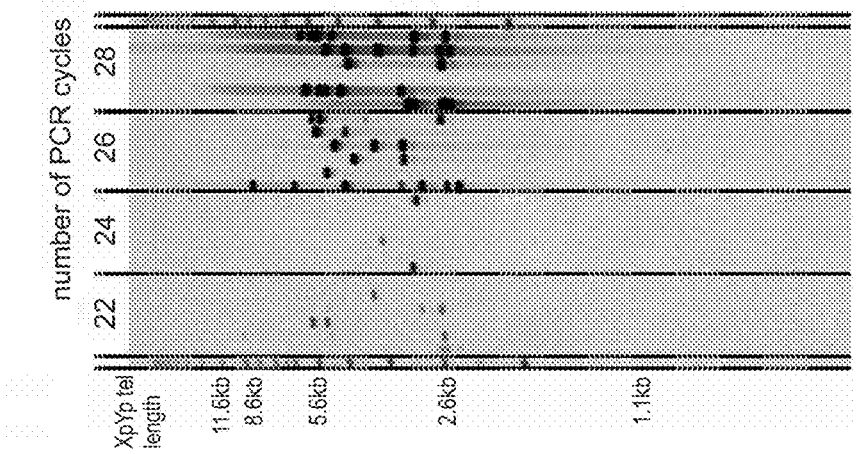

The first attempt to increase the amount of STELA PCR product generated was to increase the number of PCR cycles. 250 pg DNA extracted from a clonal population of MRC5 fibroblasts was added to multiple 30 µl PCR reactions and subject to either 22, 24, 26 or 28 cycles (FIG. 2). A small number of STELA-PCR products were generated when the reactions were subject to either 22 or 24 PCR cycles however the intensity of these products was not sufficient to result in their detection using the FRAGMENT ANALYZER™ capillary electrophoresis system (FIG. 2a&b). However when STELA PCR reactions were cycled 26 times a larger amount of PCR product was generated, resulting in more intensely hybridising bands on the STELA Southern blot. This was sufficient to allow the detection of the majority of the bands with the FRAGMENT ANA-LYZER™ capillary electrophoresis system (FIG. 2a&b). Reactions subject to 28 cycles showed an even greater intensity on both the STELA blot and the FRAGMENT ANALYZER™ capillary electrophoresis system output gel (FIG. 2a&b) and all the DNA fragments detected with the original method could be detected. Therefore subsequent HT-STELA PCR reactions were cycled 28 times as opposed to 22 cycles.

Alternative XpYp Telomere-Adjacent Primers

Figure 3A:
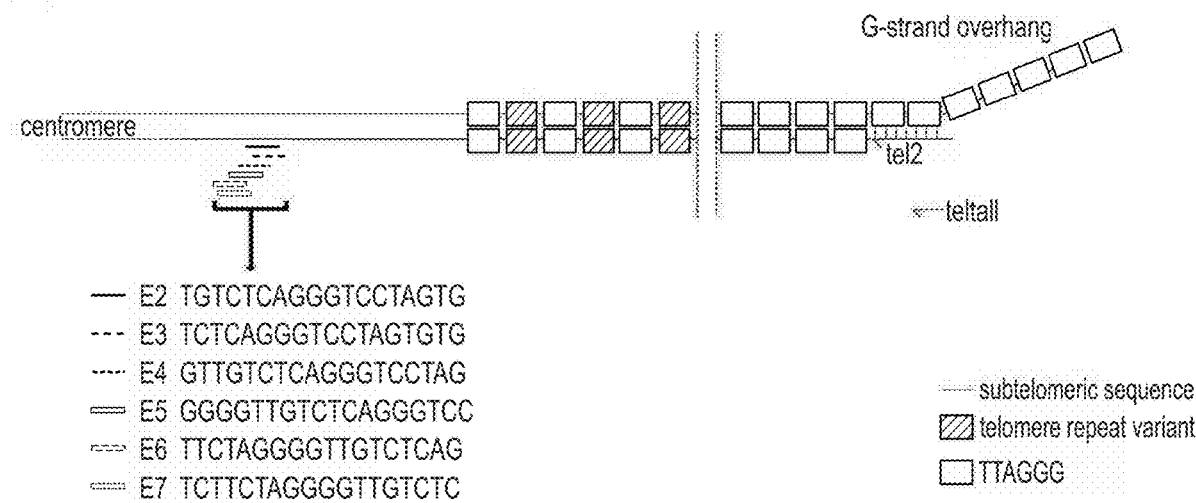
FIG. 3. Improving HT-STELA PCR product yield through the design and use of alternative XpYp telomere adjacent primers. (a) A number of alternative XpYp telomere adjacent primers were designed around the same region as XpYpE2. (b) All five of the XpYp telomere-adjacent primers were used in STELA PCR and primer performance was compared between the five primers and also to XpYpE2 to determine whether there were any increases in PCR efficiency and the generation of more PCR product. (c) Triplicate HT-STELA PCR reactions containing either XpYpE2 of XpYpE5 were loaded into a 96 well plate for analysis using the FRAGMENT ANALYZER™ capillary electrophoresis system. Relative fluorescent units (RFU) were used to indicate the amount of PCR product produced by each individual PCR reaction. The average RFU of each reaction set was then used to determine the quantity of PCR product generated using either primer.
Figure 3B:
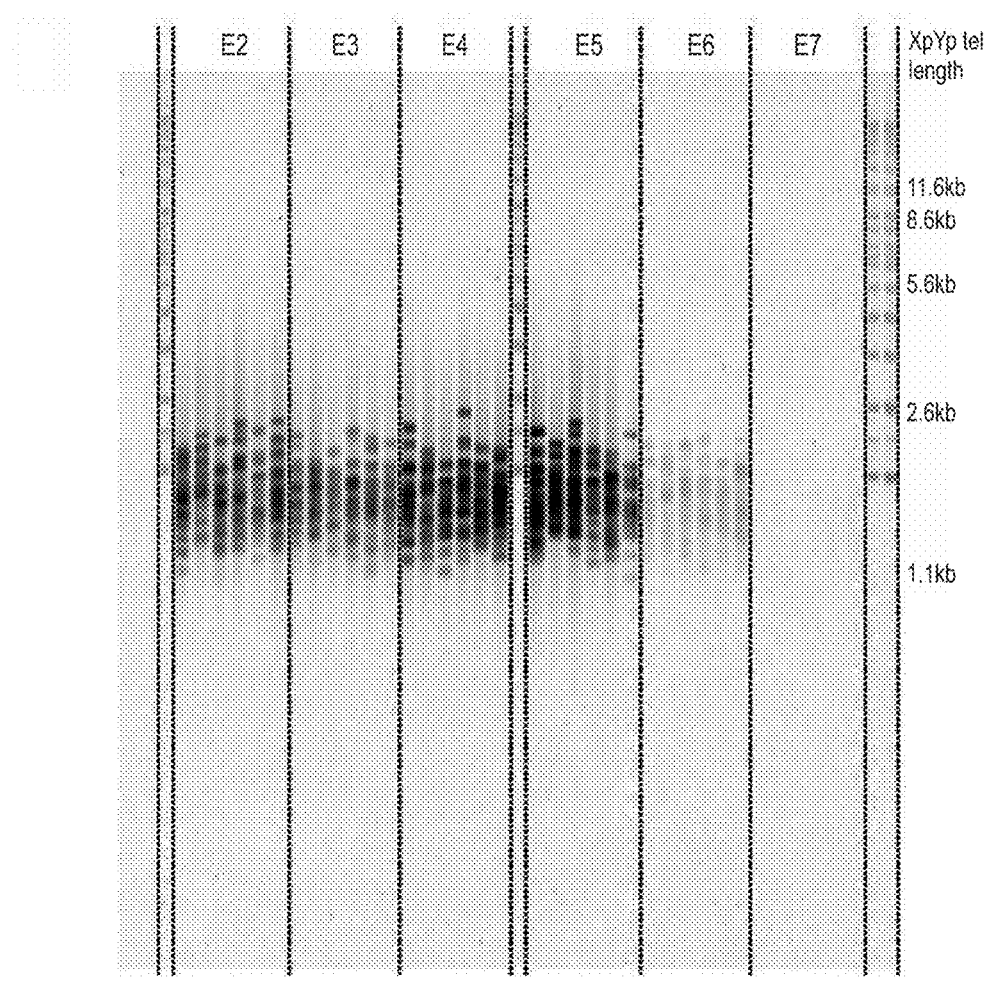
Figure 3C:
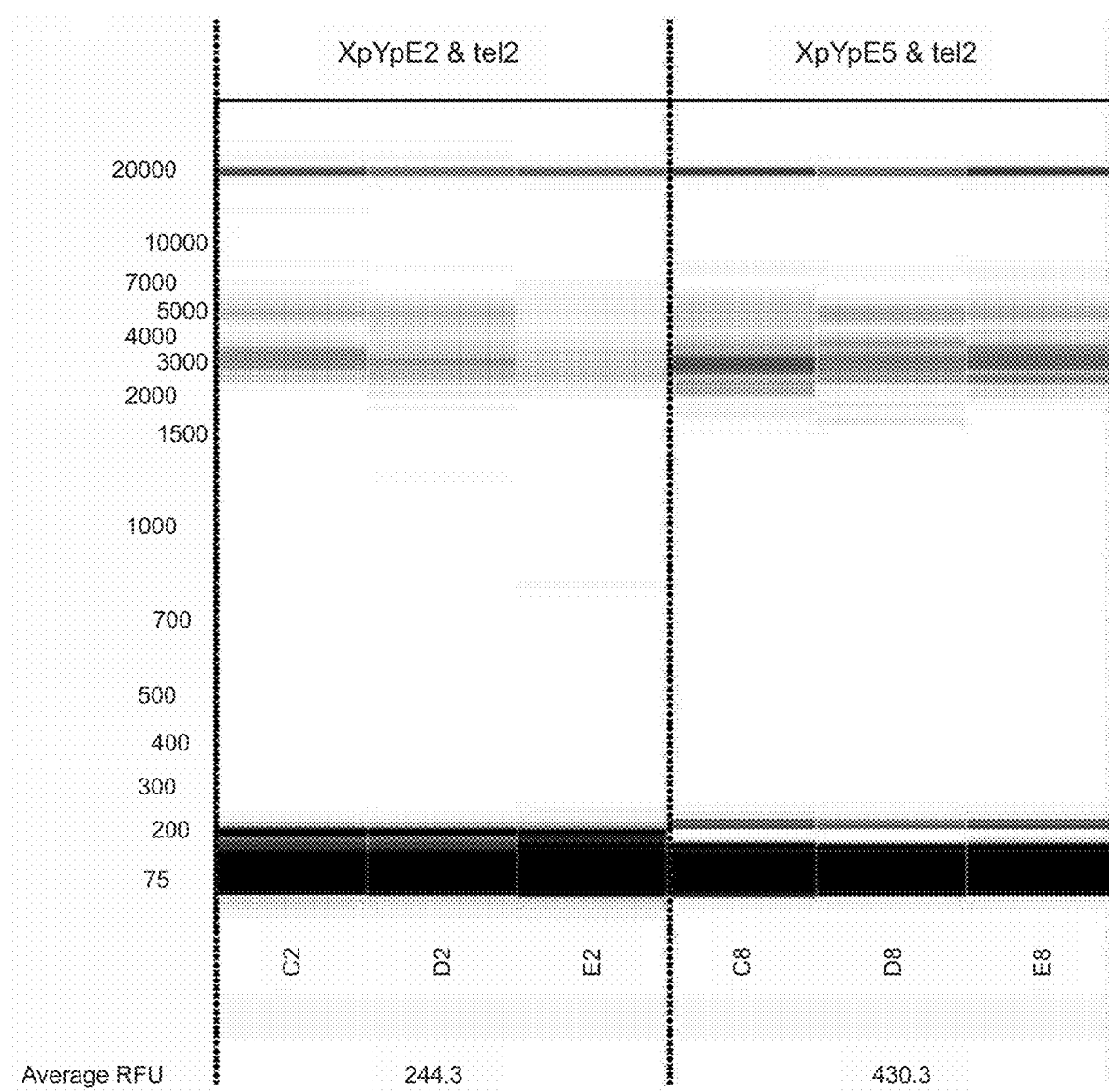

Another approach taken to increase the amount of PCR product generated during STELA PCR was to increase the efficiency PCR amplification. To do this we focused on the telomere adjacent primer used to amplify telomeric DNA in the original STELA method. XpYpE2 resides 408 nucleotides from the start of the XpYp telomere. A number of similar primers were designed around this region and used in STELA PCR to replace XpYpE2, in an attempt to increase the PCR efficiency and thereby increase the amount of PCR product generated. Five additional primers were designed (E3, E4, E5, E6 and E7) (FIG. 3a). The original STELA method was performed using each of these telomere adjacent primers and revealed that XpYpE5 resulted in the most intense banding pattern out of all the telomere adjacent primers, suggesting that this primer gave the greatest PCR efficiency (FIG. 3b). To confirm whether this increase in PCR efficiency was also detected by the FRAGMENT ANALYZER™ capillary electrophoresis system a similar experiment was performed in which the difference in PCR product generated by XpYpE2 and XpYpE5 was compared. The relative fluorescence units (RFU) given by the PRO-SIZE™Data Analysis software reflects the signal intensity of the PCR products and thereby the amount of PCR product generated. As observed with the original STELA method the XpYpE5 primer results in a more efficient PCR and the generation of more PCR product compared to XpYpE2 (FIG. 3c). When XpYpE5 was used the average relative fluorescence was 430.3 units, approximately double the relative fluorescence achieved by the STELA PCR reaction containing XpYpE2 (244.3 RFU). Therefore subsequent HT STELA PCR was performed using XpYpE5 as opposed to XpYpE2.

Increasing the Input DNA Quantity

In addition to increasing the cycle number and changing the telomere adjacent primers another approach which was taken to increase PCR product signal intensity was to increase the amount of input DNA within each STELA-PCR reaction. The purpose of this approach was two-fold: not only was it to result in more PCR product being generated allowing easier fluorescent detection, it was also an attempt to produce a telomere length distribution 'smear' as opposed to a banding pattern. There are a number of reasons why a telomere length distribution smear would be beneficial: it would allow a more rapid analysis of mean telomere length as it would require less human intervention in the analyses of data within the PROSIZE™Data Analysis software; it would require less reactions per sample; it would increase the total amount of product and it would ensure that non-specific background bands present are not incorporated into the sizing analysis.

Figure 4A:
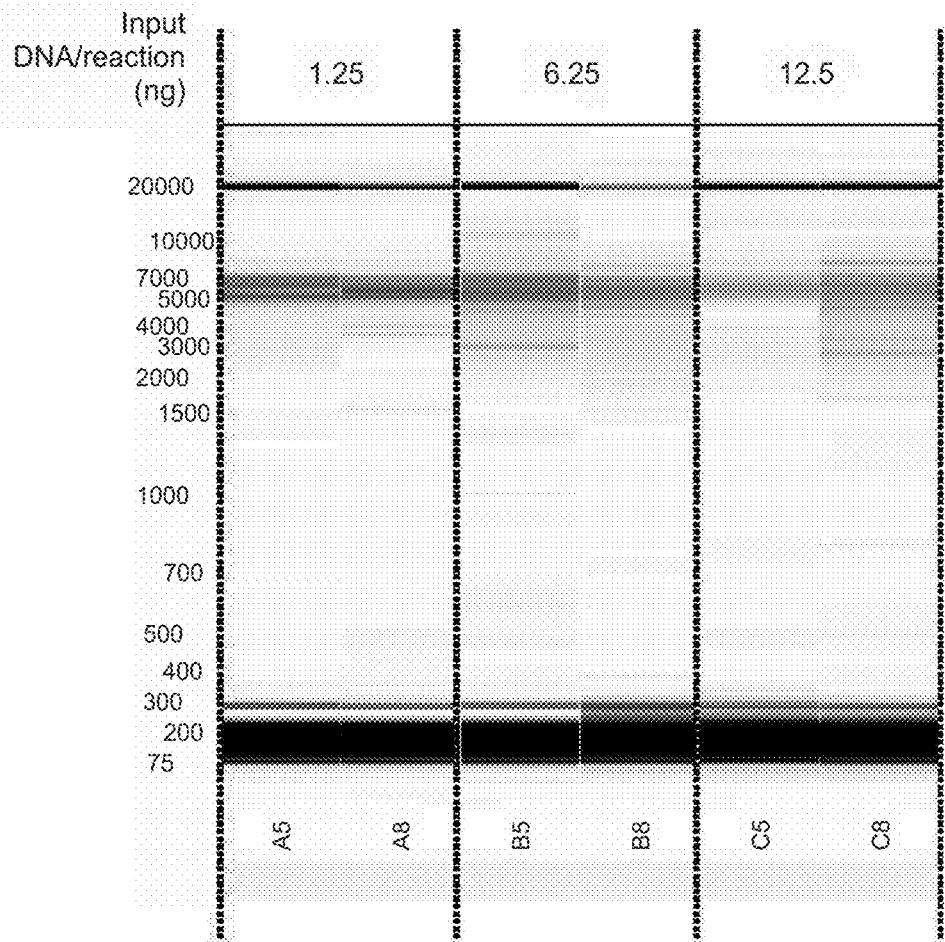
FIG. 4. Increasing the amount of input DNA per reaction results in the formation of a telomere length distribution smear as opposed to a banding pattern. (a) 1.25 ng, 6.25 ng or 12.5 ng HT1080 cl.5 DNA was added to duplicate 30 µl HT-STELA PCR reactions containing XpYpE5 and subject to 28 PCR cycles. The resulting PCR products generated were resolved and detected using the FRAGMENT ANALYZER™ capillary electrophoresis system. (b) The process in (a) was repeated but with DNA taken from a CLL patient (patient id—4408) displaying a more heterogeneous telomere length distribution. 1.25 ng, 3.125 ng, 6.25 ng, 12.5 ng, 25 ng and 47.5 ng 4408 DNA was added to multiple 30 µl HT-STELA PCR reactions which were then subject to 28 PCR fragments. Generated PCR products were resolved and detected using the FRAGMENT ANALYZER™ capillary electrophoresis system.

A DNA quantity titration was used to determine the optimum amount of DNA to add to the STELA PCR reactions. In the original STELA method 10 ng/μl dilutions are made from the concentrated stock DNA samples. 1 μl (10 ng) were taken from this dilution and added to 40 μl Tris-Hcl (pH8) containing tel2 linker oligonucleotide. 1 μl (250 μg) of this DNA/tel2 mix was then added to each PCR reaction. On the FRAGMENT ANALYZER™ capillary electrophoresis system this approach produced a faint banding pattern only after 28 PCR cycles (FIG. 2b). To allow the detection of telomere length distributions as smears using the FRAGMENT ANALYZER™ capillary electrophoresis system, increasing amounts of DNA was added to the DNA tel2 mix. Specifically, a 50 ng/μl dilution was made from stock HT1080 cl.2 DNA. 1 μl (50 ng), 5 μl (250 ng) or 10 μl (500 ng) of this dilution was added to DNA/tel2 mixes. 1 μl of these DNA/tel2 mixes were added to multiple 30 μl HT-STELA reactions giving a final concentration of 1.25, 6.25 and 12.5 ng/reaction respectively. When the generated STELA PCR products were resolved and detected by the FRAGMENT ANALYZER™ capillary electrophoresis system all three input DNA quantities resulted in visible telomere length distribution smears (FIG. 4a).

Figure 4B:
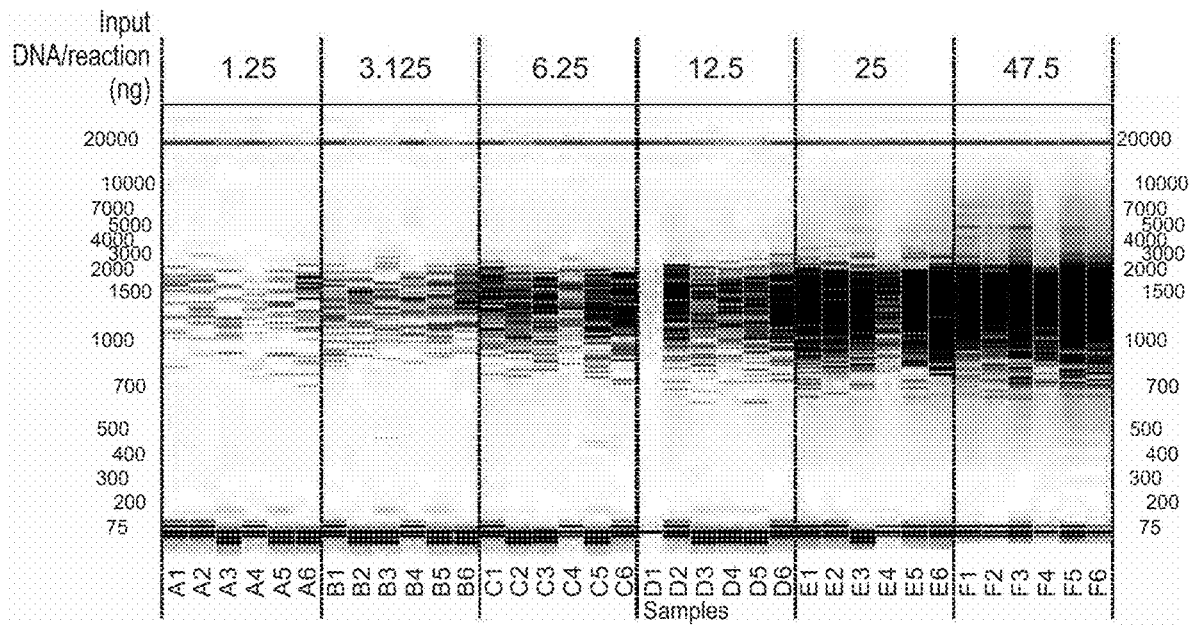

The HT1080 cl.2 XpYp telomere length distribution is homogenous. Although XpYp telomere length distributions from CLL patients are also expected to be homogenous previous work in which the XpYp telomere length distribution was studied in a panel of CLL patients by STELA revealed that the telomere length heterogeneity varies somewhat between patients. Hence the amount of input DNA that would create a telomere length distribution smear for a homogenous telomere length distribution such as HT1080 cl.2 will not necessarily produce a smear in a sample that displays a more heterogeneous XpYp telomere length distribution. To test this, a DNA sample from a CLL patient (4408) was selected that displayed a heterogeneous XpYp telomere length distribution. DNA from this patient was used for an input DNA titration ranging from 1.25-47.5 ng/reaction (FIG. 4b). The input DNA amounts that produced a telomere length distribution smear in the HT1080 cl.2 cell population, did not produce a similar smear for patient 4408, instead a clear banding pattern was observed. Once the amount of DNA in the reactions was increased to 25 ng DNA and above, the telomere length distribution was resolved as a smear in this CLL sample (FIG. 4b); the smear was robust with a strong signal and was reproducible.

Reducing Primer Concentration within HT-STELA PCR Reactions

Figure 5A:
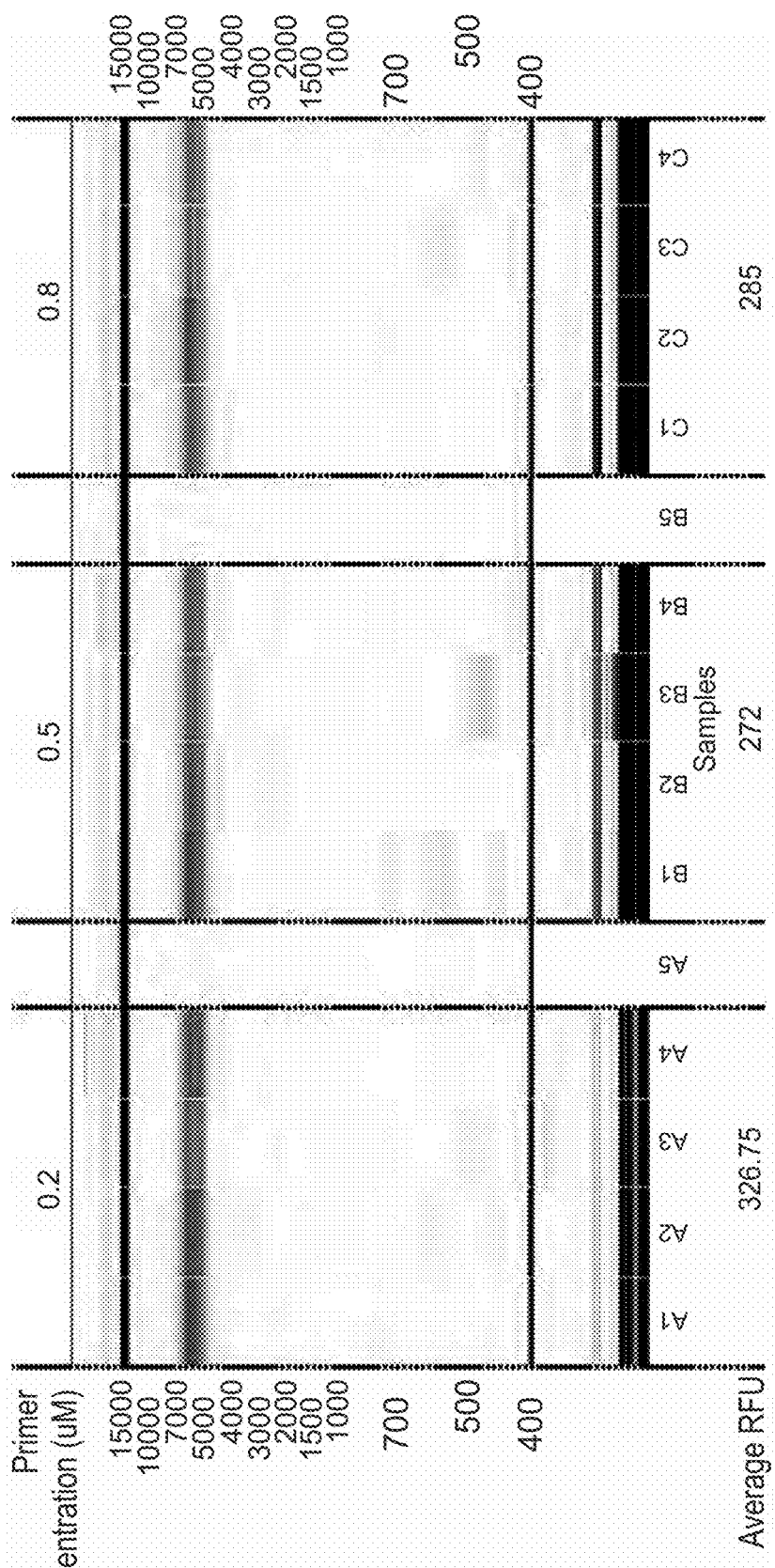
FIG. 5. Decreasing XpYpE5 and teltail primer concentration increases the amount of HT-STELA PCR product generated. (a) 30 ng HT1080 cl.5 DNA was added to multiple reactions containing either 0.2 µM, 0.5 µM or 0.8 µM telomere adjacent XpYpE5 and teltail primers. Resulting PCR products generated from the reactions were then resolved and detected using the FRAGMENT ANA- LYZER™ capillary electrophoresis system. The Relative Fluorescence Units (RFU) was given for each reaction. Within each reaction set the individual reaction RFUs were averaged giving an indication of the quantity of PCR product generated by a particular primer concentration. (b) The process in (a) was repeated but with HT STELA PCR reactions containing different primer concentrations. PCR products generated from reaction sets containing 0.05 µM, 0.1 µM or 0.2 µM were resolved and detected on the FRAGMENT ANALYZER™ capillary electrophoresis system and average RFU for a reaction set was calculated.
Figure 5B:
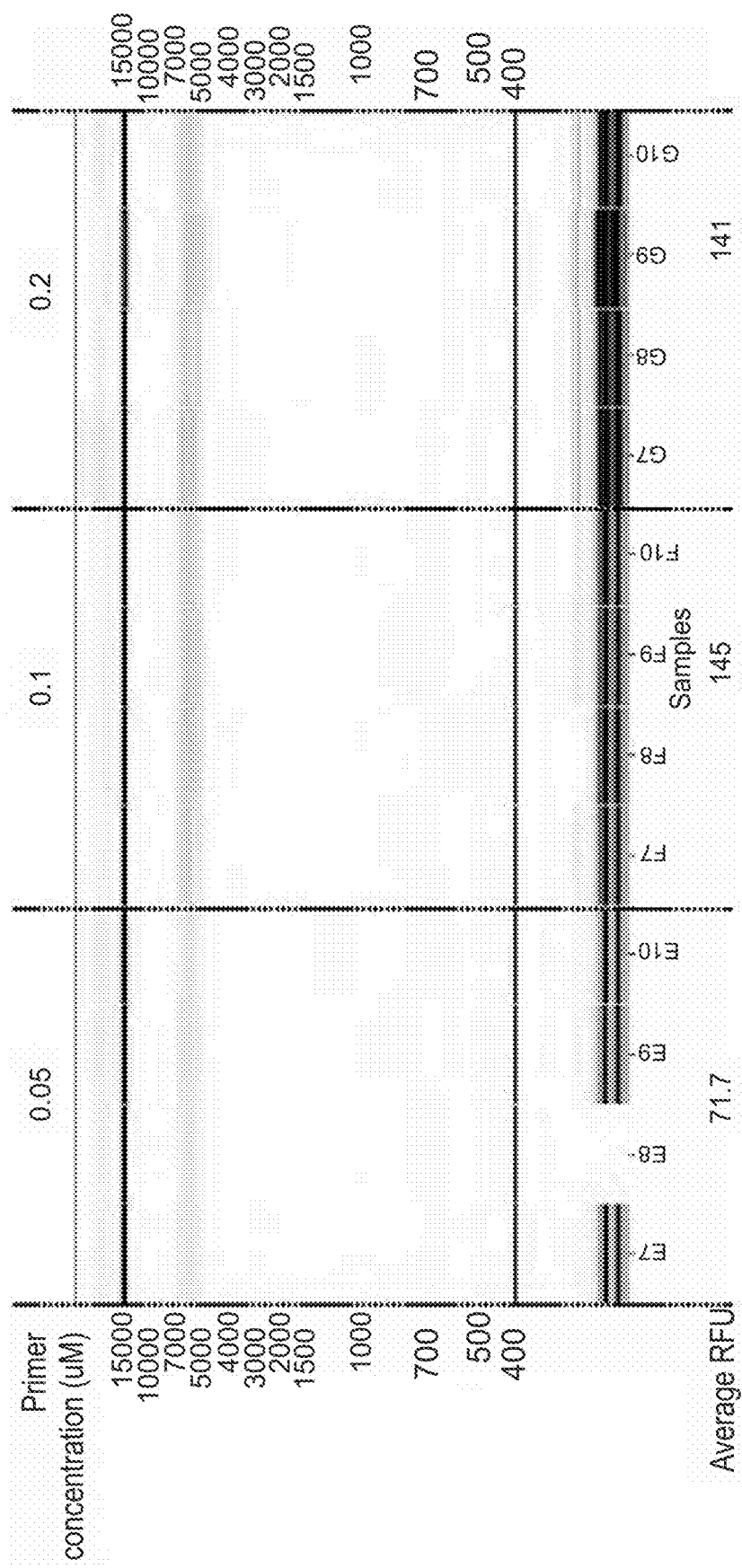
Figure 15D:
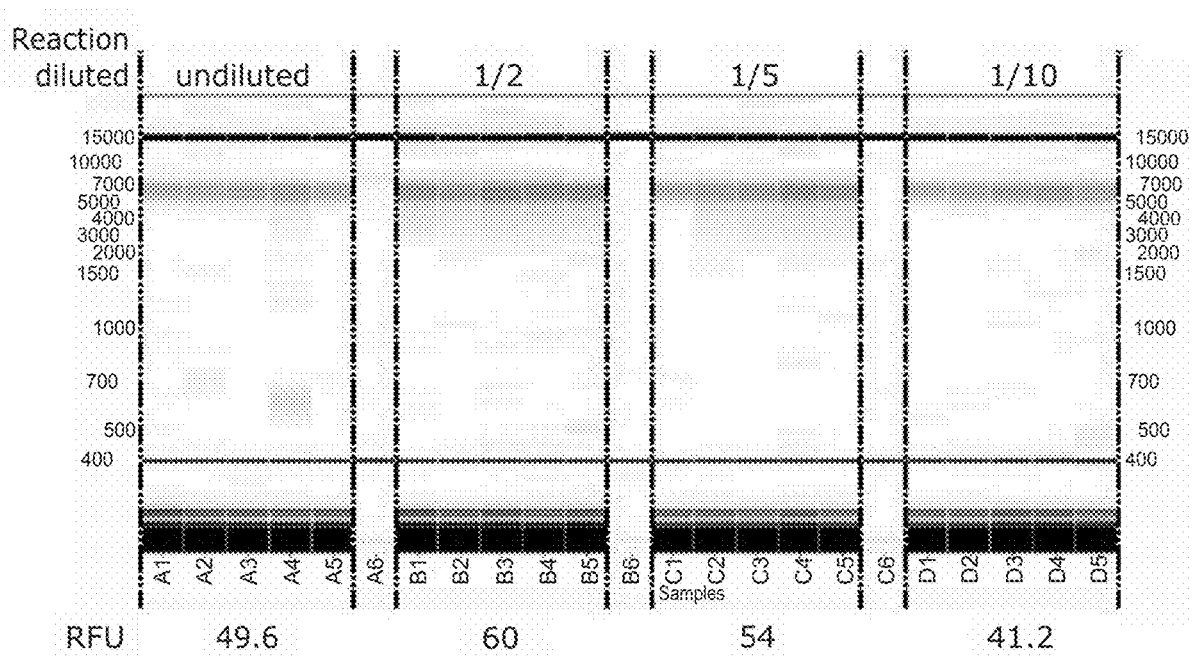
FIG. 15. Optimisation of HT-STELA PCR to improve PCR product yield. A number of different optimisation experiments were performed to improve HT-STELA PCR product yield. For each optimisation experiment generated PCR products were resolved and detected on the FRAGMENT ANALYZER™ capillary electrophoresis system (a) 30 ng HT1080 cl.2 DNA/tel2 mix was added to HT-STELA PCR reactions containing either 2 mM, 4 mM or 6 mM MgCl$_2$. (b) The linker oligonucleotide tel2 was added to HT1080 cl.2 DNA (10 ng/µl) to either 250 µM, 25 µM or 5 µM final concentration. 30 ng of each DNA/tel2 mix was added to HT-STELA PCR reaction. After electrophoresis and detection RFU (Relative Fluorescence Units) were measured by the PROSIZE™Data Analysis software. RFU are indicative of how much PCR product was detected by the FRAGMENT ANALYZER™ capillary electrophoresis system. (c) 30 ng HT1080 cl.2 DNA/tel2 mix was added to HT-STELA PCR reactions containing either Red Hot Taq polymerase (Thermo Scientific) or Titanium Taq (Clontech). (d) A 30 µl HT-STELA PCR reaction was either undiluted or diluted 2×, 5× and 10×. The amount of PCR product detected was measured by RFU analysis. (e) 30 ng HT1080 cl.2/tel2 mix was added to HT-STELA PCR reactions with a volume of either 30 µl or 60 µl. The amount of PCR product detected was measured by RFU analysis.
Figure 15E:
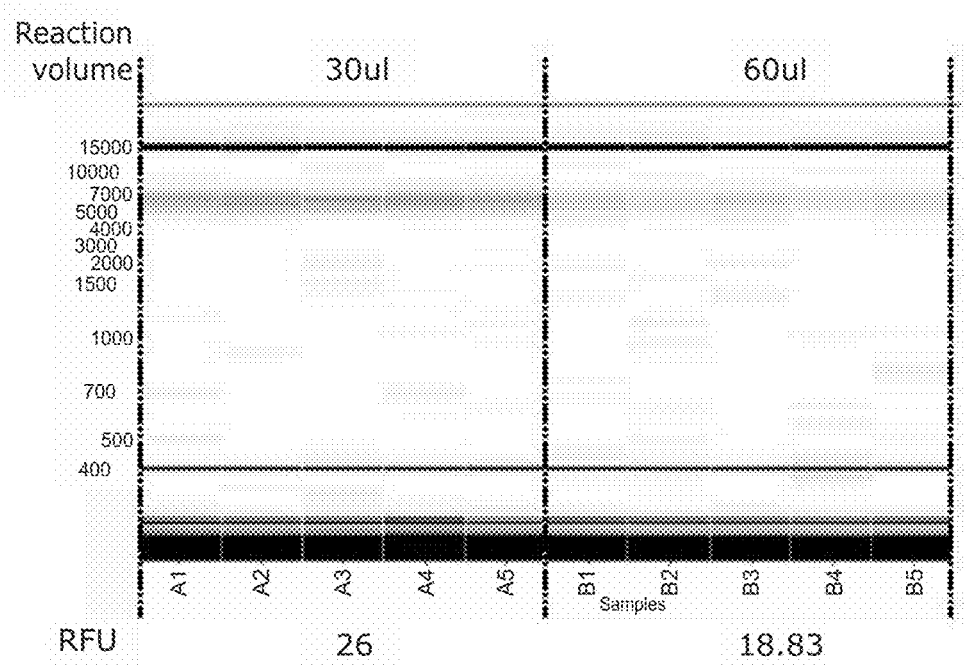

A number of other factors were altered in an attempt to boost the signal intensity of the HT-STELA PCR products. These including further increasing the PCR reaction volume, diluting the PCR reactions, altering the $MgCl_2$ concentration and changing the Taq polymerase (FIG. 15). None of these modifications increased the relative fluorescence of the PCR products on the FRAGMENT ANALYZER™ capillary electrophoresis system however reducing the primer concentration within the PCR reactions did increase PCR product formation. In the original STELA reaction conditions the final primer concentration is 0.5 μM. A primer titration was performed using primer concentrations of 0.2, 0.5 and 0.8 μM. A comparison of the average relative fluorescence given by each reaction set revealed that the reactions containing 0.2 μM XpYpE5 and teltail generated more PCR product than the reactions containing 0.5 and 0.8 μM primers (FIG. 5a). Because of the increased PCR product formation observed when primer concentration was reduced, the primer titration was extended further to incorporate even lower primer concentrations (0.05-0.2 μM). However, reducing the primer concentration further did not result in an increase in PCR product formation. PCR reactions which contained 0.1 μM XpYpE5 and teltail generated PCR products to level as the reactions containing 0.2 μM primers. PCR product formation began to recede as primer concentration was reduced below 0.1 μM (FIG. 5b). Therefore subsequent HT-STELA PCR reactions were performed with XpYpE5 and teltail concentrations of 0.2 μM.

Figure 6A:
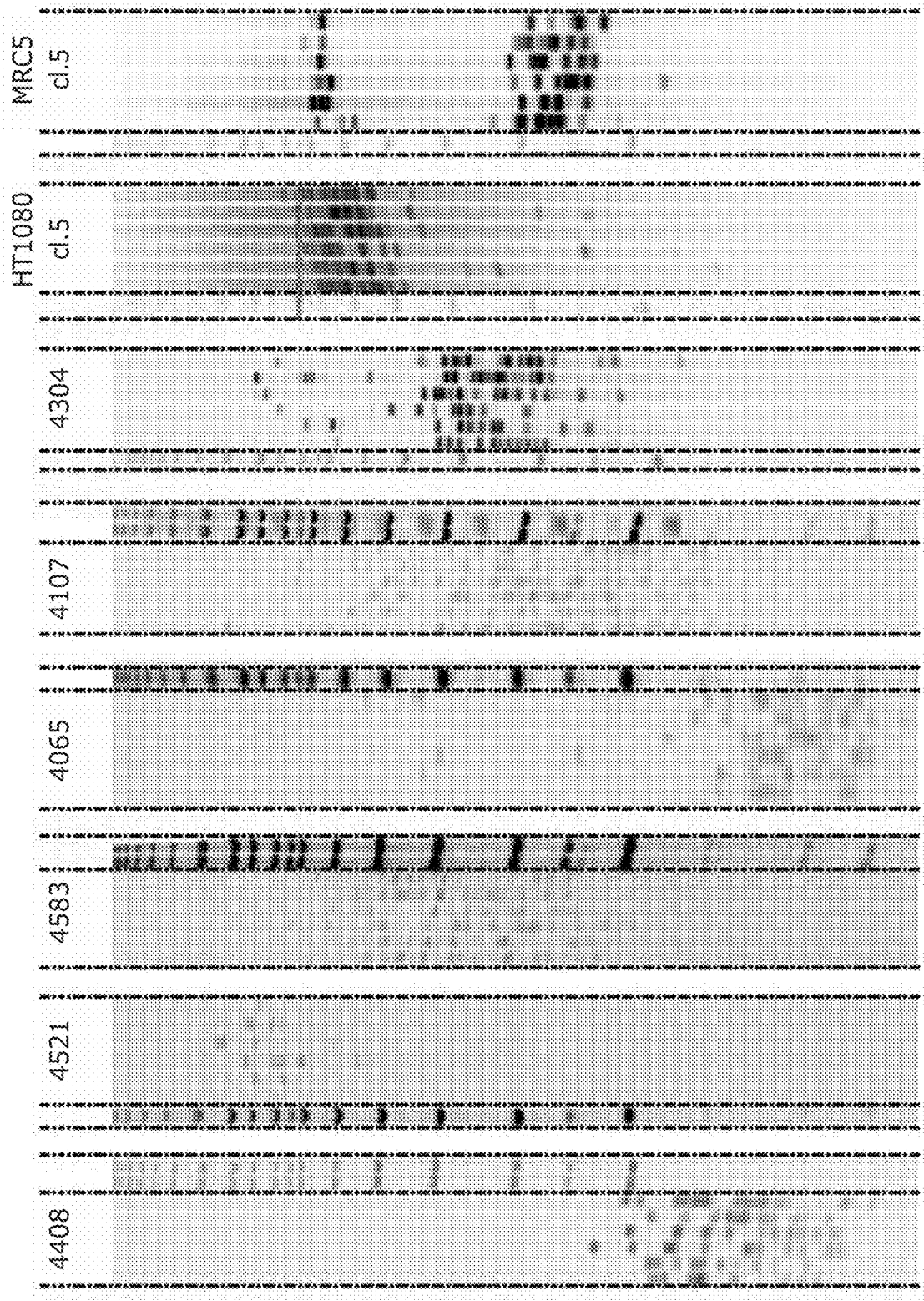
FIG. 6. Comparison of mean telomere length measured by conventional Single Telomere Length Analysis (STELA) and High Throughput STELA (HT-STELA) (a) Mean XpYp telomere length from a panel of CLL samples along with clonal populations of the HT1080 and MRC5 was analysed by conventional STELA. Mean telomere length was measured by band quantification using Phoretix software (Non-Linear dynamics) and taking a mean of all the quantified bands. (b) XpYp telomere length from the same panel of samples was also measured by HT-STELA using the newly optimised conditions. For HT-STELA mean telomere length was calculated for each individual lane by the smear analysis function on the PROSIZE™Data Analysis software and calculating the average mean telomere length across all the reactions for a particular sample. (c) comparison of MTL estimate generated with STELA and HT-STELA.

Optimizing the Mean Telomere Length Sizing Accuracy Using the FRAGMENT ANALYZER™ Capillary Electrophoresis System Once the conditions were optimised to give a robust and reproducible telomere length distribution smear detected with the FRAGMENT ANALYZER™ capillary electrophoresis system, the sizing accuracy of the HT-STELA technique was compared to the original STELA method. HT-STELA and STELA was performed on a panel of CLL samples, as well as on clonal populations of the HT1080 (cl.5) and MRC5 (cl.5) cell lines (FIG. 6). The original STELA method revealed the expected high degree of variability in both the mean telomere length, as well the levels of heterogeneity of the XpYp telomere length distributions between samples (FIG. 6a). A useful feature of the MRC5 cl.5 DNA was that it displayed a bimodal XpYp telomere length distribution (Baird et al., 2003), providing a test of the resolution for the FRAGMENT ANALYZER™ capillary electrophoresis system in determining whether it is able to successfully amplify and resolve the two allelic telomere length distributions separately (FIG. 6a).

Figure 6B:
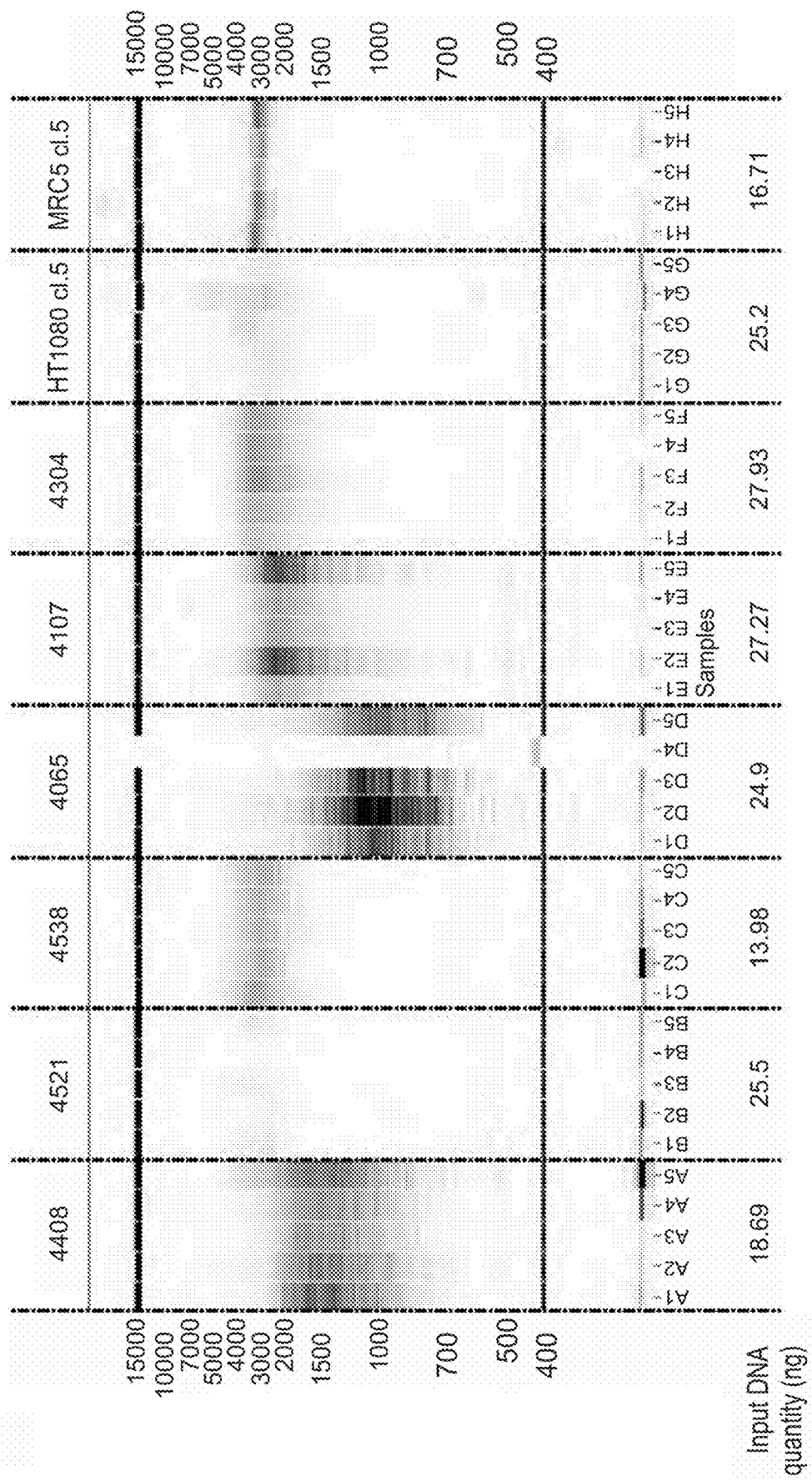
Figure 6C:
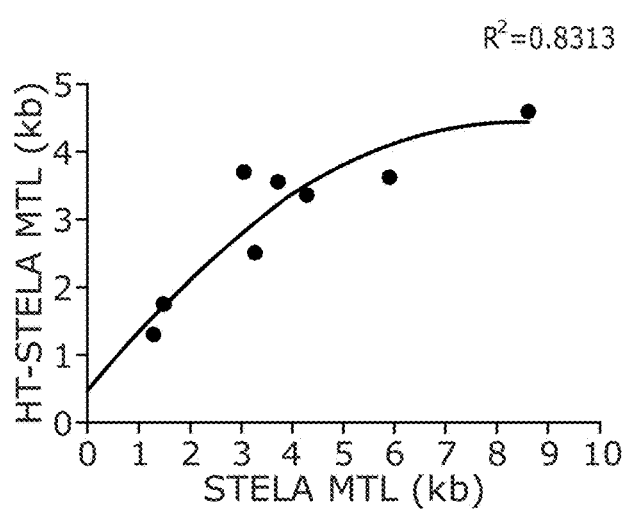

Quantification of the STELA PCR products was performed using Phoretix software (FIG. 6c; NonLinear Dynamics) and calculation of mean telomere length revealed that it varied from 1.29 kb (CLL sample 4065) to 8.598 kb (CLL sample 4521) (FIG. 6c). When the same panel of samples was analysed by HT-STELA using the newly optimised conditions a telomere length distribution smear was produced for all samples. However the intensity of the telomere length distribution smears differed between samples, suggesting differences in PCR efficiency between reaction sets (FIG. 6b). One explanation for this could have been that this variation in PCR product formation could be due to differences in the input DNA quantity for each reaction set. However when comparing the input DNA quantity per reaction this does not correlate with the differences in signal intensity observed on the FRAGMENT ANALYZER™ capillary electrophoresis system output gel (FIG. 6b). Another explanation could be that the DNA samples of the panel may contain differing levels of PCR inhibitors which could affect PCR product formation.

The correlation between HT-STELA and the original STELA method was not absolute, indeed the optimal relationship was not linear (R2=0.83; FIG. 6c). The results are summarised in FIG. 6c. It was clear that large discrepancies in mean telomere length measurement were present between STELA and HT-STELA, particularly for longer telomeres such as those in CLL sample 4521 (FIG. 6). The original STELA method revealed that HT1080 cl5 XpYp telomeres exhibit a homogenous telomere length distribution, however when this same DNA is analysed by HT-STELA a weak but considerably heterogeneous distribution is present (FIG. 6a-b). Moreover the MRC5 cl5 exhibits a clear bimodal XpYp telomere length distribution (FIG. 6a). However analysis by HT-STELA results in the detection of only the lower allele telomere allele on the output gel. Therefore, when the mean telomere length was measured for this sample, only the lower allele was represented. Mean telomere length was measured by the smear analysis function within the PROSIZE™Data Analysis software. Overall these discrepancies resulted in an underestimation in telomere length by a mean of 892 bp when measured by HT-STELA. This will be problematic when using the technology in a prognostic setting.

Whilst there was a considerable improvement in the ability to detect telomere length distributions using HT-STELA with the FRAGMENT ANALYZER™ capillary electrophoresis system the loss of the longer telomere length distributions need to be addressed. Determination of mean telomere length rapidly, but also accurately, was required for accurate prognostication, therefore steps were taken to improve the accuracy of HT-STELA.

Cycle Titration

Figure 7A:
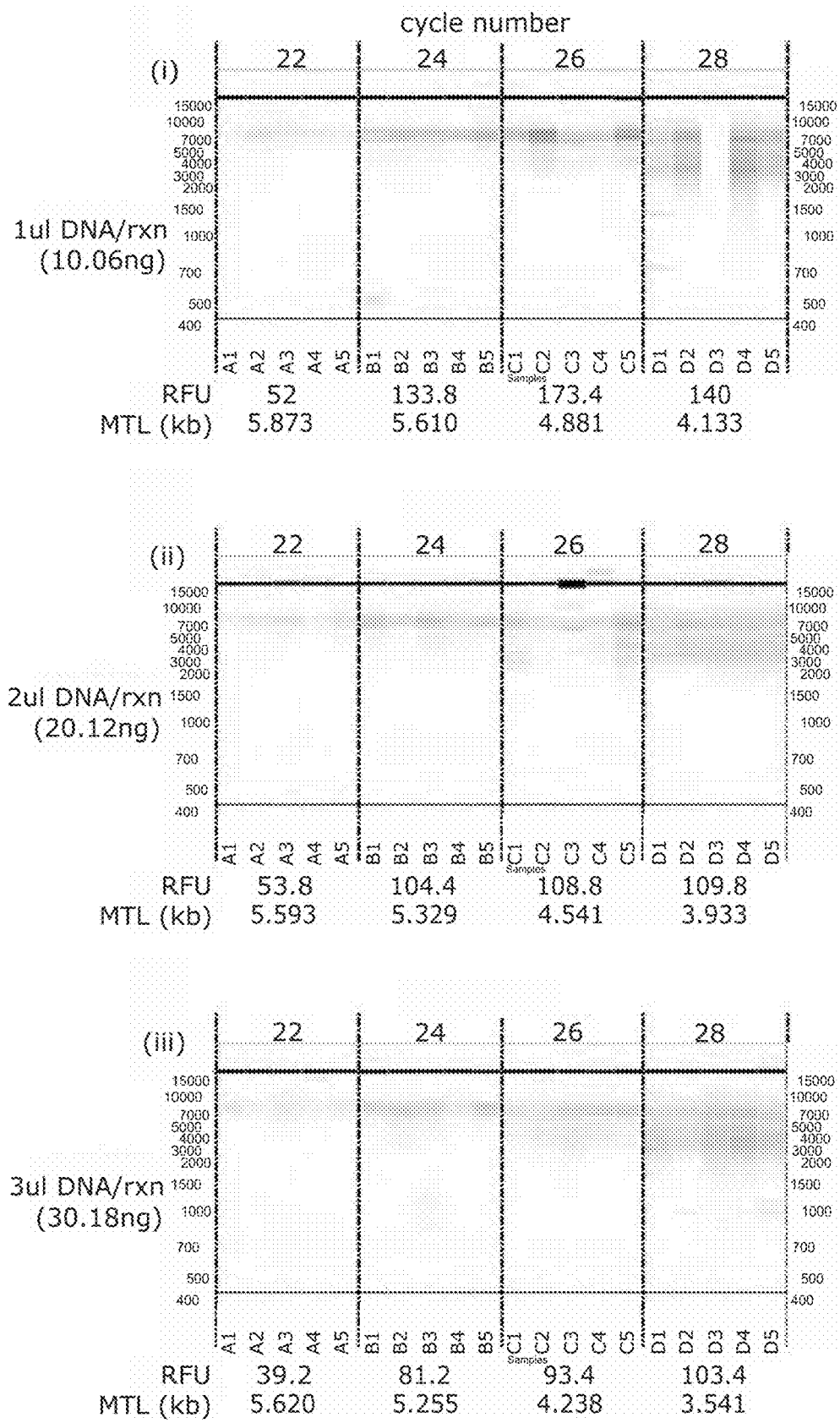
FIG. 7. Reducing the amount of PCR cycles reduces the amplification of artefactual short molecules and preferential amplification of shorter telomeres in HT-STELA and results in an accurate mean XpYp telomere length measurement (a) 1 µl (10.06 ng), 2 µl (20.12 ng) and 3 µl (30.18 ng) HT1080 cl.5 DNA was added to multiple HT-STELA PCR reactions and subject to 22, 24, 26 or 28 PCR cycles. Generated PCR product was resolved and detected on the FRAGMENT ANALYZER™ capillary electrophoresis system. (b) The same process as (a) was performed but with 1 µl (6.6 ng), 2 µl (13.2 ng) or 3 µl (19.9 ng) MRC5 cl.5 DNA. (c) 30 ng HT1080 cl.2 DNA was added to multiple HT-STELA PCR reactions and subject to either 22 or 23 PCR cycles. Generated PCR products were resolved and detected on the FRAGMENT ANALYZER™ capillary electrophoresis system. Average RFU (Relative fluorescent units) is used to indicate the average amount of PCR product produced by each PCR reaction set. The mean telomere length (MTL) for each reaction set was calculated using the smear analysis on the PROSIZE™Data Analysis software. UA/LA=The ratio in peak height between the upper telomeric allele and the lower telomeric allele.

A cycle titration was performed in which HT-STELA PCR reactions containing 10.06 ng, 20.12 ng or 30.18 ng of HT1080 cl.5 DNA were cycled for between 22-28 cycles (FIG. 7a); it was apparent that the heterogeneity of the product sizes generated was dependent on the number of PCR cycles. When all three sets of HT-STELA PCR reactions were subject to 22 PCR cycles, a homogenous telomere length distribution was observed with a mean telomere length very similar to the mean telomere length measured by the original STELA method (5.822 kb) (FIG. 6a). 24 cycles of PCR resulted in a reduction in the mean fragment length of 263 bp, 264 bp and 365 bp for the 10.06 ng, 20.12 ng or 30.18 ng reaction sets respectively (FIG. 7a). Further increasing the PCR cycle number results in an even greater reduction in mean telomere length to the point where after 28 PCR cycles the 1 µl, 2 µl and 3 µl reaction sets had a mean telomere length measurement 1.741 kb, 1.659 kb and 2.079 kb lower than the PCR reactions cycled 22 times. From the FRAGMENT ANALYZER™ capillary electrophoresis system output gel it was clear that for all three sets of reactions the telomere length distribution smear extended downwards as an increased number of smaller PCR products are generated and it is this that caused such dramatic underestimations in mean telomere length: The mean telomere length measurements after 28 PCR cycles observed in FIG. 7 was very similar to the HT1080 cl.5 mean telomere length measurement made when measured along with the CLL4 panel (3.618 kb) (FIG. 6c), suggesting this may be the cause of the mean telomere length measurement inaccuracies observed in the panel CLL of samples previously tested (FIG. 6). These data are consistent with amplification of non-telomeric products with high cycle numbers.

Additionally we noted that the amount of variation in mean telomere length between the different reaction sets containing different DNA quantities increased the more the reactions are cycled. After 22 PCR cycles the difference between the HT-STELA PCR reactions containing 10.06 ng DNA (FIG. 7ai) and 30.18 ng DNA (FIG. 7aiii) is 254 bp. However after 28 cycles this difference was 592 bp. Such differences in the concentration of the input DNA into the HT-STELA reaction may sometimes occur when this process is tested on CLL patient DNA. Using 22 cycles as opposed to 28 reduced the variation within the system and provided a more reliable comparison of mean telomere length between samples.

Figure 7B:
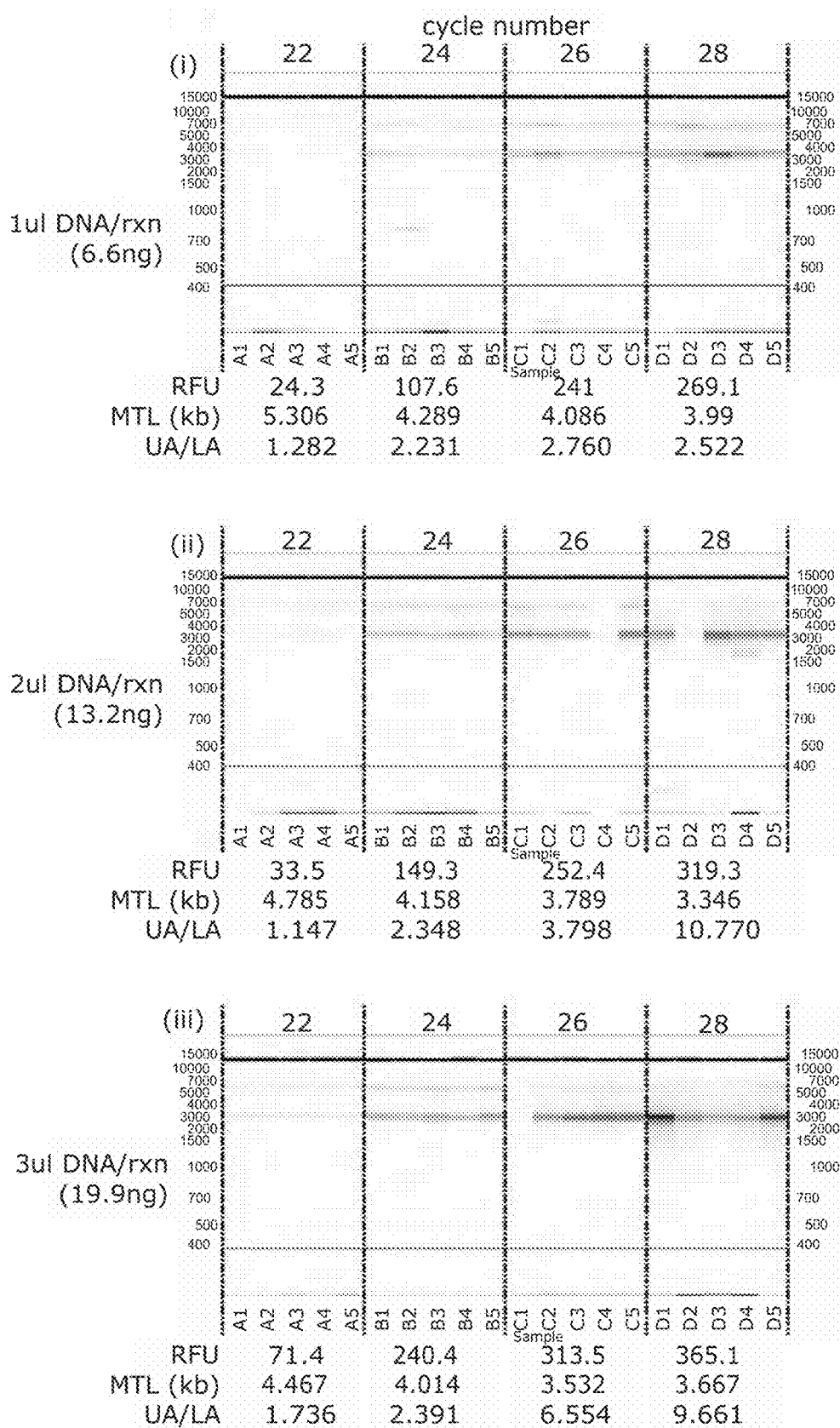

A cycle titration was also undertaken using DNA from a clonal population of the MRC5 fibroblast cell line (clone 5), this clone displays a bi-allelic telomere length distribution however when analysed using HT-STELA a single telomere length distributions could be detected (FIG. 6). Three reaction sets were constructed containing either 6.6 ng, 13.2 ng or 19.8 ng MRC5 cl.5 DNA. These reactions were then subject to 22, 24, 26 or 28 PCR cycles (FIG. 7b). It was clear from these experiments that both the number of cycles and the amount of input DNA influenced the distributions obtained. With the 2 µl and 3 µl reaction sets, a reduction in the cycle numbers from 28 to 22 resulted in an improvement in the ratio of the peak height between the upper telomeric allele (UA) and the lower telomeric allele (LA), such that at 22 cycles a ratio close to expected 1:1 allelic ratio was obtained, whereas at 28 cycles the ratio was 1:10. The UA/LA ratio was also improved by reducing the cycle number from 28 to 22 in the 1 µl reaction set. At 22 cycles the UA/LA ratio was 1:1.282 (FIG. 7b(i)). After 28 cycles the ratio was 1:2.522 which is not as high as the 2 µl and 3 µl reaction sets indicating that the ratio between alleles was also influenced by the amount of input DNA, with a reduction in the amount of input DNA improving the ratio of allelic amplification. These data are consistent with a preferential amplification of shorter telomeres that becomes apparent with increasing cycle number and DNA concentration. Thus a reduction in both the cycle number and input DNA provides a better representation of the telomere length distributions.

Figure 7C:
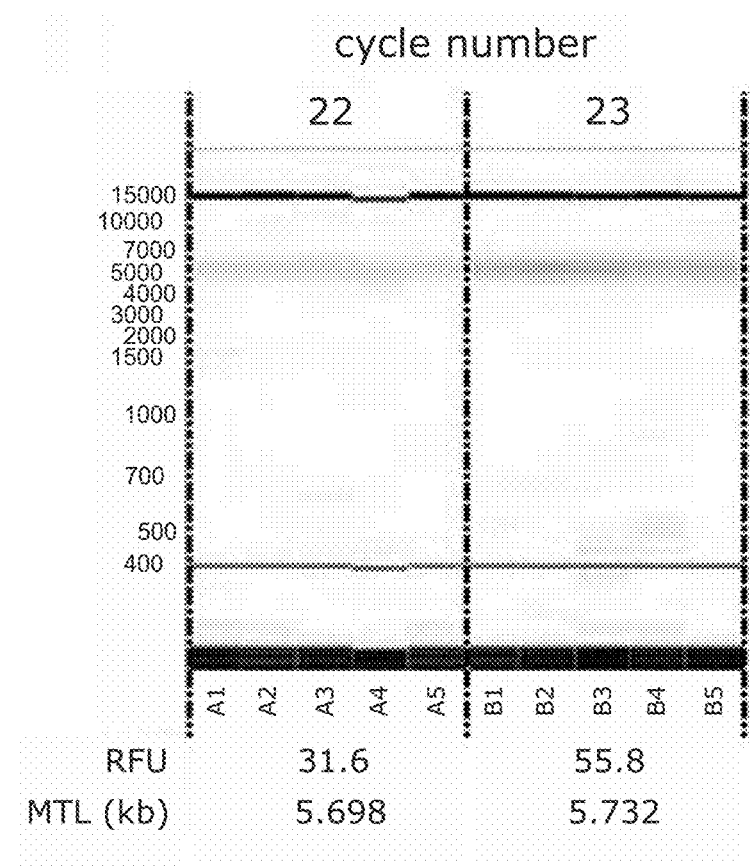

Whilst it was clear that 22 cycles yielded a robust telomere length profile, the total signal was relatively low and close the limit below which telomere sizing becomes inaccurate (as defined later in (FIG. 11)). The cycle number was therefore increased to 23 as this increased the amount of PCR product generated with no effect on mean telomere length measurement (FIG. 7c).

Taken together these data demonstrate that a reduction in the PCR cycle number results in less artefactual amplification, less heterogeneity and a more accurate representation of the telomere length distribution. It also demonstrated that this could be improved still further by the optimisation of the amount of input DNA.

Marker Optimisation

Another potential source of sizing inaccuracies within the HT-STELA method is the lower (75 bp) and upper (20 kb) markers provided with the DNF-930 dsDNA kit (Advanced Analytical) that are used for inter-capillary normalisation. During STELA-PCR a large number of fragments less than 200 bp in size are generated, these are composed of primer complexes and primer-dimers. The intensity of these fragments on the FRAGMENT ANALYZER™ capillary electrophoresis system masked the position of the lower 75 bp marker (FIG. 8a) making it difficult to identify this marker. This led to incorrect normalisation of the STELA products and subsequently inaccurate telomere length measurements. A number of strategies were taken to resolve this issue. Firstly PCR purification was performed using the 96 well plate QIAquick columns (Qiagen) in an attempt to remove these smaller DNA fragments. Although this purification removed a significant amount of the fragments <200 bp it was not sufficient to completely eliminate them and the same problem remained (FIG. 8b). Additionally, the PCR purification was inconsistent between samples and also removed some of the telomere derived PCR products thereby reducing their signal intensity. It was therefore not possible to purify away the fragments that prevented detection of the lower mark and this strategy was not pursued further.

An alternative approach was to customise the markers to suit HT-STELA on the FRAGMENT ANALYZER™ capillary electrophoresis system. We used a lower marker that was larger than the size of the larger primer complexes and primer-dimers 200 bp but smaller than smallest fragment size of a telomere generated with STELA using the XpYpE5 (415 bp) or the XpYpC (882 bp) primers. Thus a commercially available 400 bp DNA fragment was obtained for this purpose (NoLimits, Thermo Scientific). The upper marker was also customised for STELA: 15 kb was chosen which was over 5 kb larger than the longest mean telomere length observed in our cohorts of CLL or colorectal cancer tumour samples[24, 27]. As this 15 kb marker was smaller than the 20 kb marker supplied with the DNF-930 kit, it will be better resolved in the gel matrix and thus sizing will be improved. These marker DNA fragments were mixed, diluted to the same concentration as the 75 bp and 20 kb markers supplied within the DNF-930 kit (0.5 ng/µl) and then resolved on the FRAGMENT ANALYZER™ capillary electrophoresis system along with STELA PCR reactions (FIG. 8c). The electropherogram revealed that the new 400 bp marker is represented as a clear single peak that is distinct from the primer complexes and primer-dimers (FIG. 6c). The resolution of the 15 kb fragment was improved compared to the 20 kb marker provided with the DNF-930 kit. Together these custom markers allow inter-capillary normalisation on the FRAGMENT ANALYZER™ capillary electrophoresis system when used for resolving HT-STELA products.

Figure 9A:
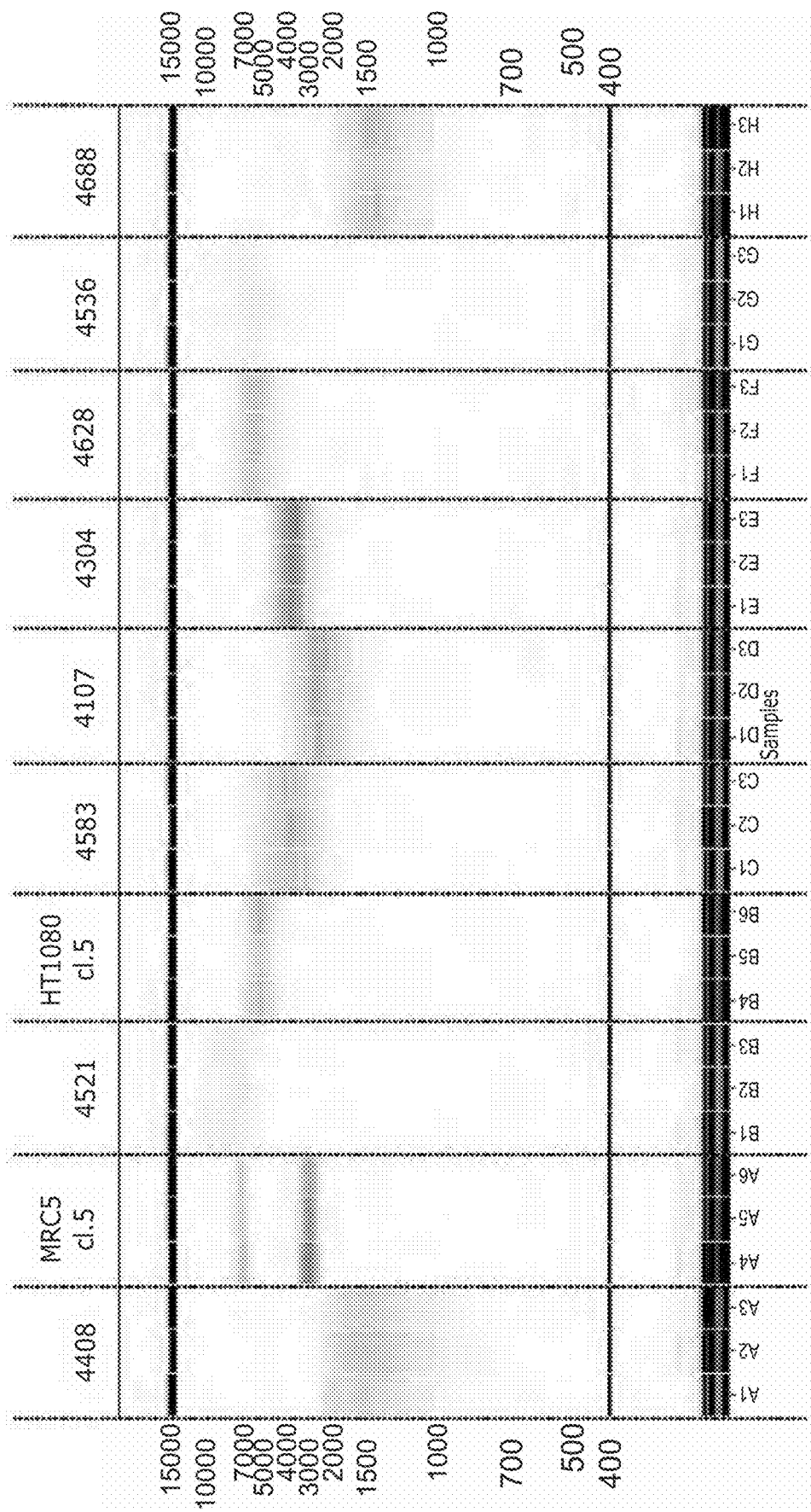
FIG. 9. Reanalysis of mean telomere length measured by High Throughput STELA (HT-STELA) after reducing PCR cycle number (a) XpYp HT-STELA PCR was performed on a panel of CLL samples as well as on clonal populations of HT1080 and MRC5. 20-30 ng DNA of each DNA was added to 30 µl HT-STELA PCR reactions which were then subject to 22 PCR cycles. Resulting PCR products generated were resolved and detected on the FRAGMENT ANALYZER™ capillary electrophoresis system. Mean XpYp telomere length was calculated for each individual lane by the smear analysis function on the PROSIZE™Data Analysis software (Advanced Analytical) and calculating the average mean telomere length across all the reactions for a particular sample. (b) comparison of MTL estimate generated with STELA and HT-STELA.
Figure 9B:
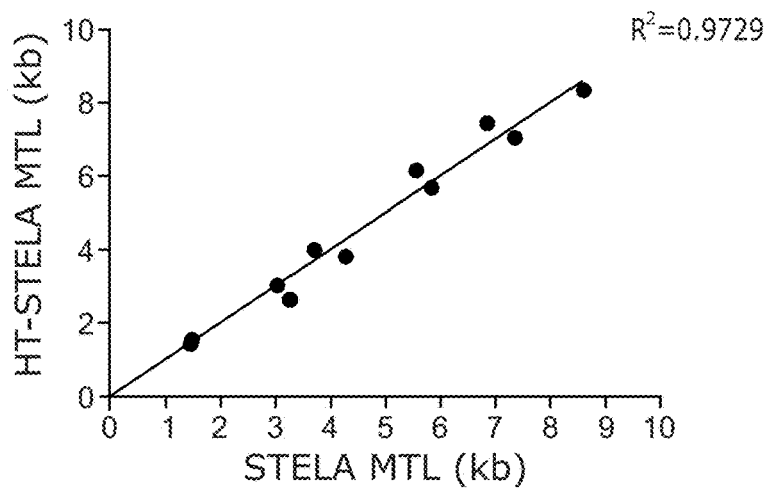

Reanalysis of Mean Telomere Length Using Optimised DNA Input, Cycle Number and the Custom Markers Once HT-STELA PCR conditions were altered to improve the sizing accuracies of the method the mean telomere length of an additional panel of CLL samples as well as the clonal populations of MRC5 (cl.5) and HT1080 (cl.5) was analysed (FIG. 9). Strong, robust telomere length distribution smears were obtained for the samples. MRC5 cl.5 displayed a clear bi-allelic telomere length distribution and HT18080 XpYp telomeres formed a homogenous distribution similar to what is seen with the original STELA method (FIG. 9a). The mean telomere length determined with HT-STELA was compared with the original STELA method. This revealed far less variation between the two methods with a highly significant linear correlation between STELA and HT-STELA ($p<0.0001$; $R2=0.97$; FIG. 9b). Before adjusting the HT-STELA conditions the relationship between STELA and HT-STELA was not linear (FIG. 6c) and accurate mean telomere length measurements over 2.5 kb was not possible. However the modified conditions provided a linear relationship between STELA and HT-STELA allowing accurate determination of telomere length within the full telomere length ranges analysed.

Coefficient of Variance

Figure 10A:
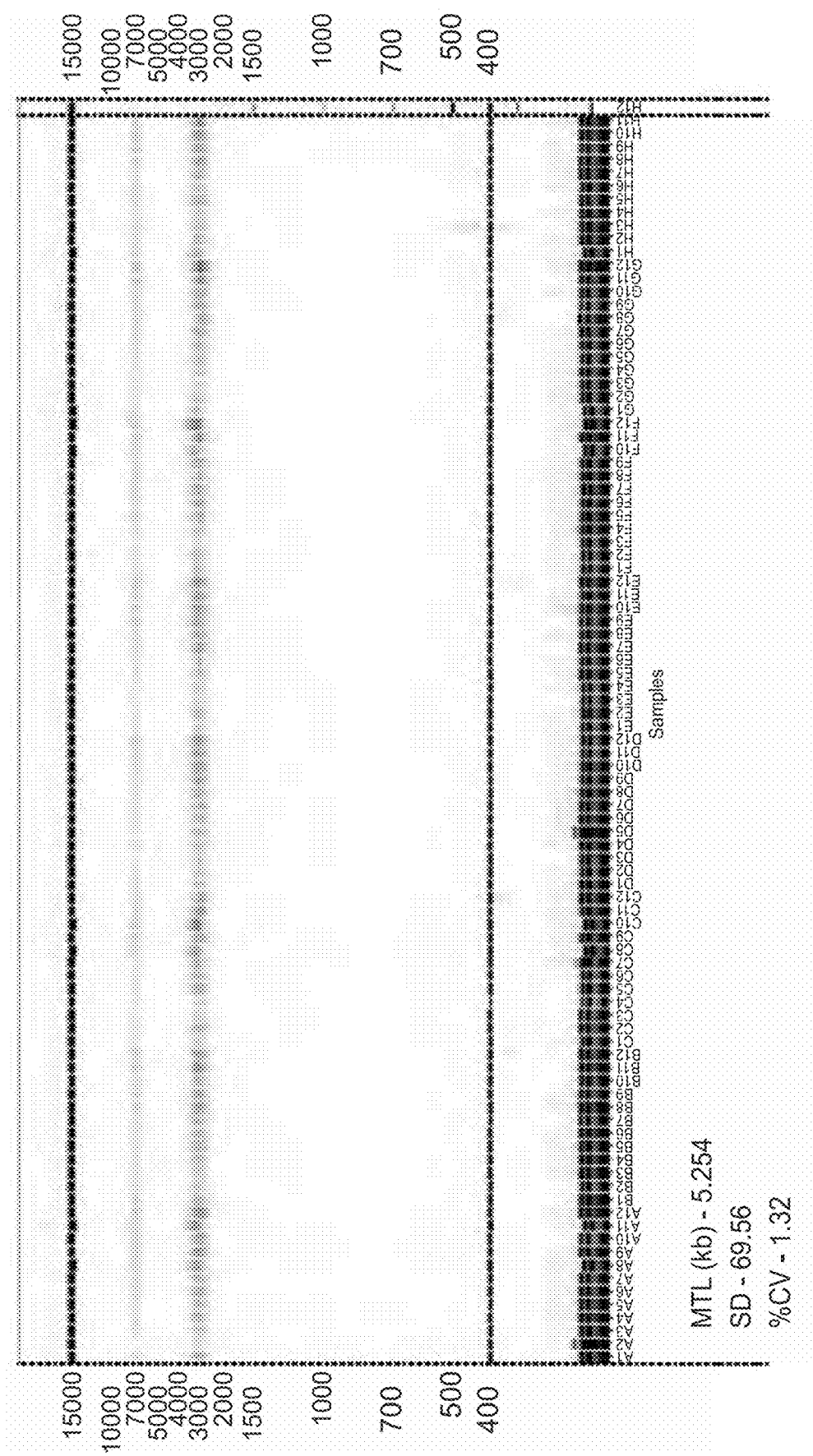
FIG. 10. Analysis of the coefficient of variance of HT-STELA (a, b & c). 30 ng MRC5 cl.5 DNA was added to 95×30 µl replicate HT-STELA PCR reactions containing the telomere-adjacent primer XpYpE5 and subject to 23 PCR cycles. The generated PCR products were loaded onto a 96 well plate before being resolved and detected by the FRAGMENT ANALYZER™ capillary electrophoresis system. The resulting output gels shown are from three independent runs using the same PCR reactions. Telomere length for both telomeric alleles was measured using the smear analysis tool in PROSIZE™Data Analysis software. The mean telomere length was then calculated for all 95 HT-STELA PCR reactions. Coefficient of variance (% CV) was calculated using the formula % CV=(SD/MTL)*100 and was calculated between PCR reactions within the same 96 well plate (stated underneath each output gel) or for the same PCR reaction resolved and detected in three independent runs (table 1).
Figure 10B:
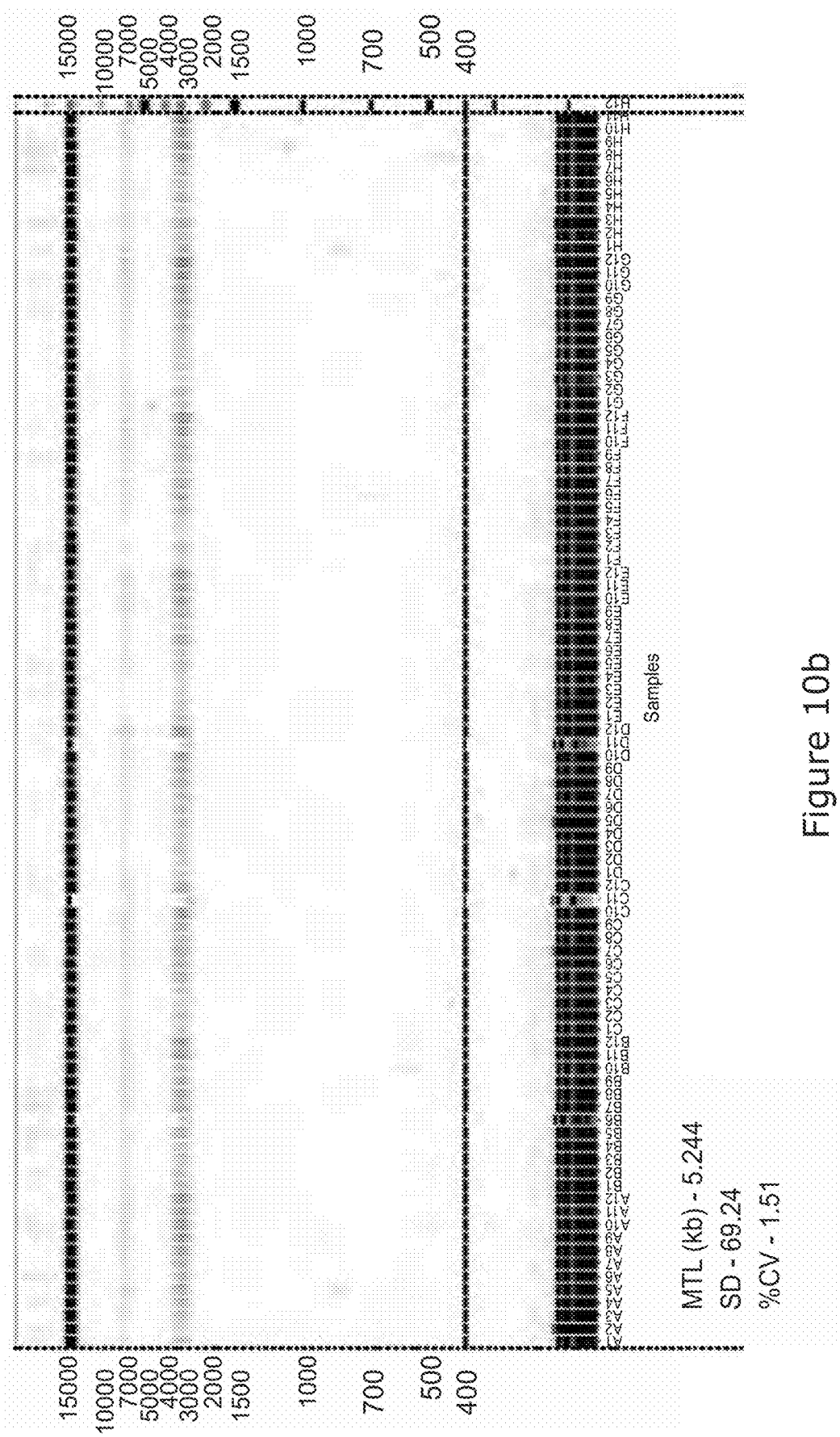
Figure 10C:
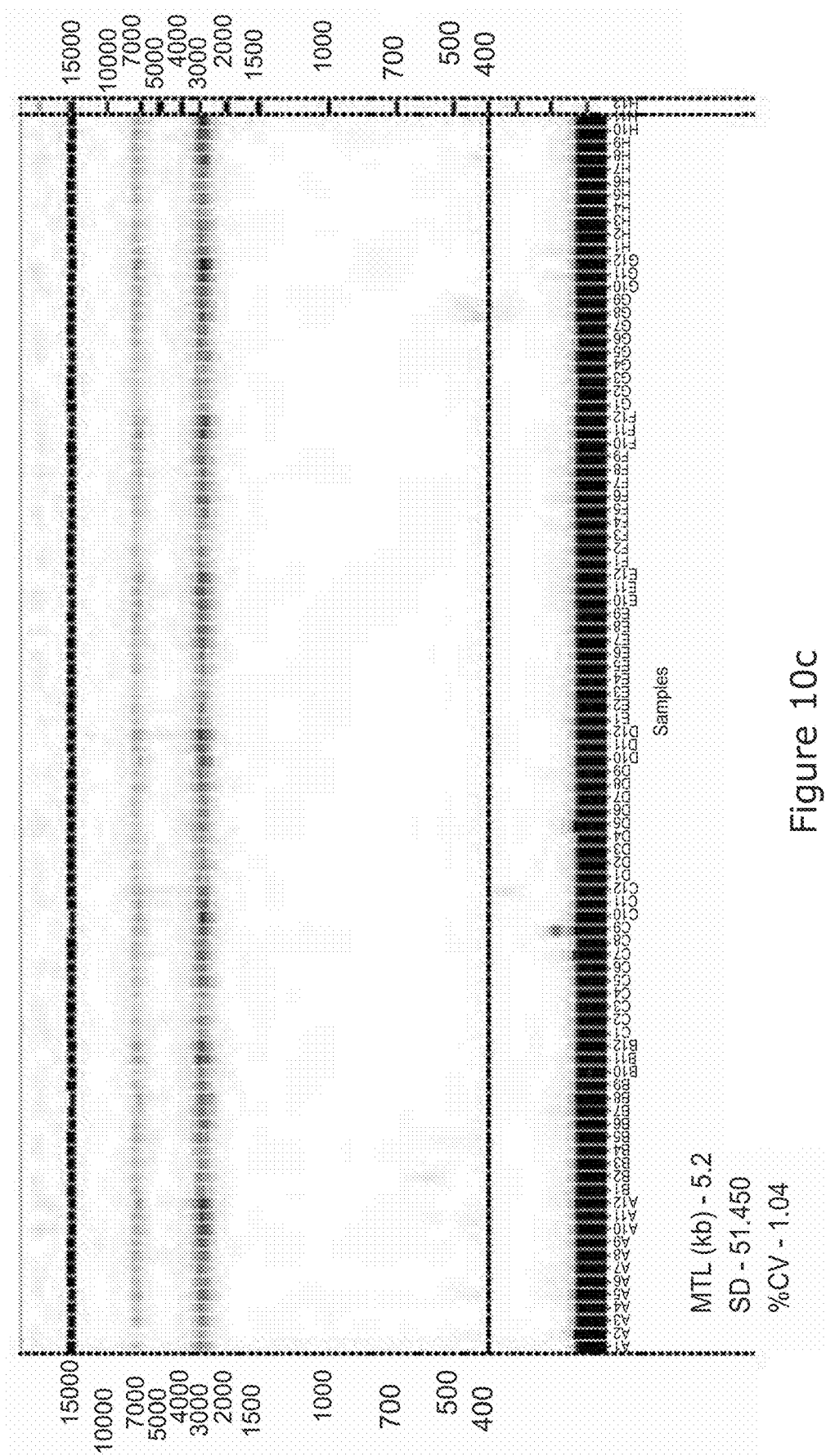

We determined the measurement error within the HT-STELA system by calculating the inter- and intra-assay coefficient of variation. To do this we applied HT-STELA to the same MRC5 cl.5 DNA sample. Each reaction contained 30 ng DNA and was subjected to 22 PCR cycles, across one 96 well plate containing 95 separate STELA reactions and one molecular weight marker. The plate was analysed three times using the FRAGMENT ANALYZER™ capillary electrophoresis system (FIG. 10). The intra-assay coefficient of variance was determined for each of the three runs of the FRAGMENT ANALYZER™ capillary electrophoresis system and ranged from 1.04 to 1.51% with a mean of 1.29% (FIG. 10). The inter-assay coefficient of variance was determined as 1.23% (table 2). Overall the inherent variation within the system is very low and means that robust, reproducible telomere length measurements can be made with confidence using this approach.

Quality Control

It was important to incorporate a quality control measure into the HT-STELA assay to ensure that the technique maintains the high level of telomere length measurement accuracy observed in the original STELA method. In this regard an important aspect of the output data generated by HT-STELA was the total signal generated as defined by the relative fluorescence units (RFU) detectable with FRAGMENT ANALYZER™ capillary electrophoresis system given for each telomere length distribution smear.

Figure 11:
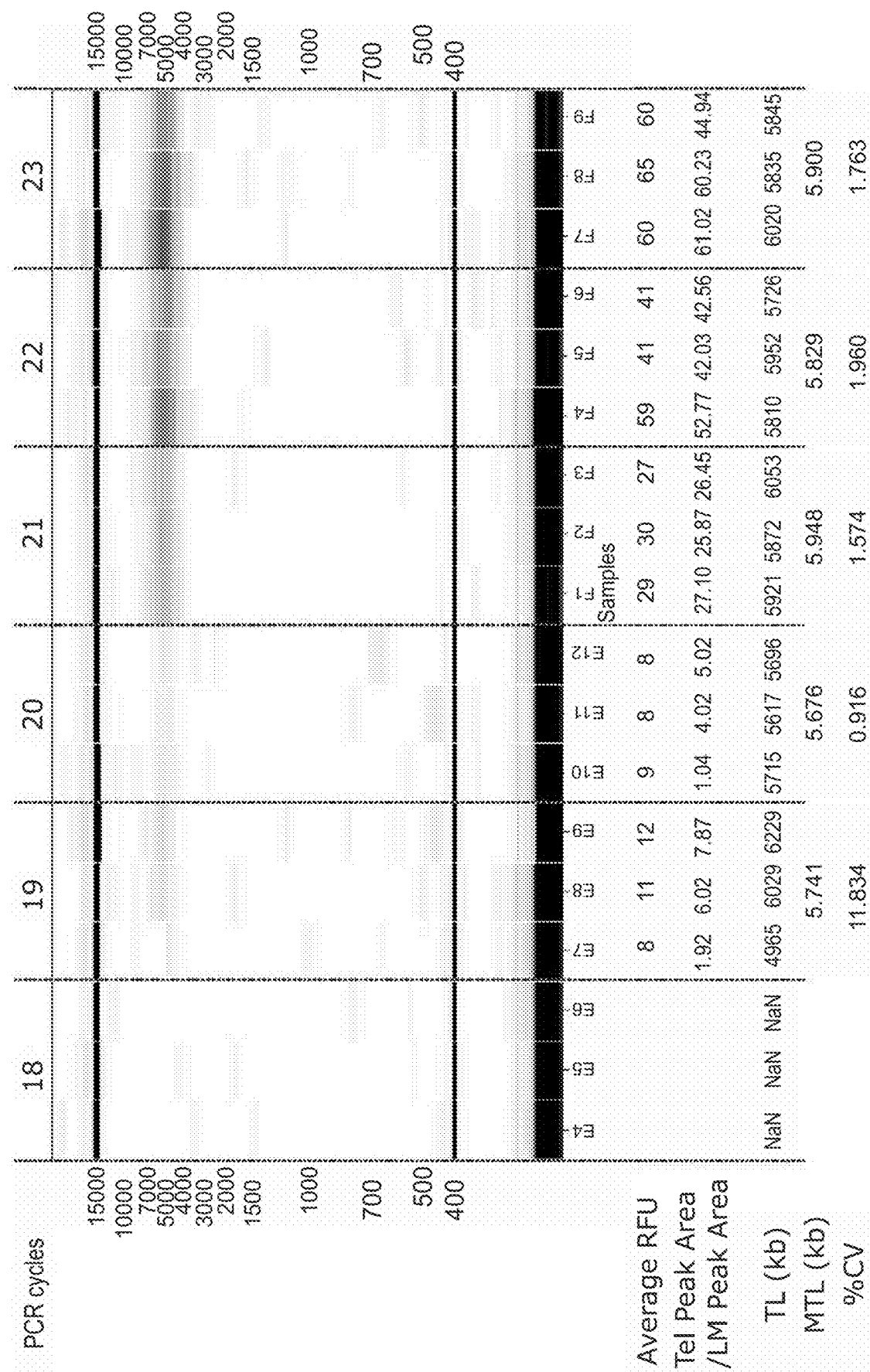
FIG. 11. Peak height analysis to determine what RFU value gives inaccurate mean telomere length measurement. 30 ng HT1080 cl.2 DNA was added to HT-STELA PCR reactions. These reactions were then subject to 18, 19, 20, 21, 22 or 23 PCR cycles. Generated PCR products were resolved and detected on the FRAGMENT ANALYZER™ capillary electrophoresis system. Relative Fluorescence Units (RFU) represent the PCR product amount. Mean telomere length was calculated for each lane using the smear analysis tool within the PROSIZE™Data Analysis software (Advanced Analytical). Tel peak area=area under a telomere length distribution smear peak on an electropherogram in PROSIZE™Data Analysis software. LM peak area=peak area under lower marker peak on electropherogram. Tel peak area was designated as a percentage of the LM peak area using the peak area values given by PROSIZE™Data Analysis software in the formula (Tel peak area/LM peak area)*100. TL=telomere length, MTL=mean telomere length, % CV=coefficient of variation.

To determine the lower RFU limit at which the mean telomere length measurement becomes unreliable a PCR cycle titration was performed: HT1080 cl.2 DNA was added to HT-STELA reactions which were then subject to 18-23 PCR cycles. The rationale behind this experiment was that as PCR cycle number decreases the amount of PCR product generated and hence the RFU value also decreases. The point at which telomere length measurement becomes inaccurate can then be monitored. The signal intensity of the HT1080 cl.2 telomere smears decreased as a function of decreasing cycle numbers, such that after 18 cycles no telomere signal could be detected. Between cycle numbers 21 and 23 a robust signal was obtained (between 27-65 RFU) and the estimation of telomere length was consistent (FIG. 11). The signal decreased still further at 19-20 cycles to 8-12 RFU. The telomere smear could be detected however the peak intensity of the smear was similar to that of the background and the mean telomere length estimate had deceased (FIG. 11). We therefore considered that the lowest signal to provide a reliable telomere length estimate was 25 RFUs.

Although the peak RFU value is indicative of the amount of PCR product generated and detected this will not always be consistent, for several reasons: Firstly RFU will be subject to variation between different fragment analyzer machines. Secondly the RFU measurement is taken from the highest point of a peak on the electropherogram. The heterogeneity of a telomere length distribution and hence the width of a telomere smear peak on the electropherogram is not taken into account. Therefore robust heterogeneous telomere length distributions whose RFU signal is more dispersed may be discarded as their peak height is lower than for homogenous distributions. Although this may not pose too much of a problem in CLL patients as XpYp telomere length in this disease has been shown to be homogenous it is more pertinent when applying the same criteria to other cancers which show more telomere length heterogeneity.

It was necessary to identify a unit which could be used to determine the lower limit of acceptable PCR product formation during HT-STELA without discriminating against heterogeneous telomere length distributions and would be consistent between different fragment analyzers. The area under a telomere length distribution peak (Tel peak area) may provide a more appropriate measure of PCR product formation as it encapsulates all HT-STELA PCR products detected by the fragment analyzer. However the same machine-to-machine variability problem still existed and required normalization. One constant in the electrophoresis and detection process were the markers. Normalizing the telomere smear peak area value by a marker peak area value such as the lower marker peak area (LM peak area), although any marker may be selected and used consistently, would negate any such variation as differences in signal detection of a sample plate between fragment analyzers would be mirrored by the same detection differences between the lower marker on a marker plate. Additionally slight capillary-to-capillary PCR product detection variation within the same assay would also be resolved. This approach was applied to the cycle titration experiment (FIG. 11) and as mentioned earlier a consistent estimation of telomere length was obtained when HT-STELA PCR reactions were subject to 21-23 PCR cycles. A high Tel peak area/LM peak area percentage was also obtained for these PCR reactions (between 25.87-61.02%. Reducing the cycle number to less than 20 cycles resulted in decreased telomere length estimation and a large reduction in Tel peak area/LM peak area percentage (<8%) (FIG. 11). Therefore when used as a quality control measure we considered that the lowest Tel peak area/LM peak area percentage that provides a reliable telomere length estimate to be 25% when the lower marker used in the system is at a concentration of 0.5 ng/µl and marker injection of 1 kV for 10 seconds.

Maxwell DNA IQ—DNA Extraction

The use of the FRAGMENT ANALYZER™ capillary electrophoresis system provides a fast high-throughput method to measure mean telomere length in a large number of CLL patients. One key aspect of the STELA is the extraction and accurate quantification of DNA. Standard protocols based on phenol/chloroform extraction are time consuming, however this has largely been overcome by various methods that have been developed to allow rapid automated extraction of DNA. However one limiting factor is the requirement for quantification of each extracted DNA followed by subsequent dilution to a standard normalised concentration prior to the PCR steps of the process. The quantification steps can be overcome by extraction systems designed to extract defined amounts of DNA. We tested the DNA IQ Casework Pro kit (Promega) that is run on the Maxwell 16 automated DNA extraction system (Promega). This system utilises paramagnetic beads that are calibrated to absorb 100 ng of DNA from a cell preparation; therefore as long as the system is saturated, an equal amount of DNA should be extracted from each sample.

We first determined the minimum number of CLL B-cells from which 100 ng DNA can be extracted and provide a consistent HT-STELA profile. Differing numbers of CLL B-cells ($5\times10^3$, $1\times10^4$, $1.6\times10^4$, $5\times10^4$, $2\times10^5$, $5\times10^5$, $1\times10^6$ and $2\times10^6$) isolated from a blood sample of a CLL patient (FIG. 12a) were collected before being lysed for 1 hour and loaded into DNA IQ Casework Pro kits on the Maxwell instrument for DNA extraction. DNA was eluted into 80 µl of elution buffer and the tel2 oligonucleotide was added directly to the elution buffer at a final concentration of 250 pM. HT-STELA was performed on the DNA/tel2 mixes and the PCR products resolved and detected with the FRAGMENT ANALYZER™ capillary electrophoresis system (FIG. 12b). Fewer PCR products were generated from the DNA extracted from $1\times10^4$ and $5\times10^4$ cells compared to DNA extracted from greater cell numbers suggesting that this number of cells does not contain enough DNA (100 ng) to saturate the DNA IQ system. When XpYp HT-STELA was performed on DNA extracted from $2\times10^5$ to $6\times10^5$ cells a relatively consistent telomere length profile was obtained (FIG. 12b), however the number of bands and therefore the amount of DNA extracted from $8\times10^5$ and above appeared to decrease suggesting that this cell number is too great for the DNA IQ system and actually inhibits the extraction of 100 ng DNA. The DNA IQ system appears to be saturated at $4\times10^5$ cells. As sufficient DNA is extracted from this amount of cells to provide a robust HT-STELA profile, this number cell was chosen for subsequent use. Furthermore this cell number is relatively small and thus small samples can be reliably analysed.

Once the cell number at which the DNA IQ system was saturated had been determined, the reproducibility of the HT-STELA process using DNA extracted from this cell number was assessed. DNA was extracted from eight independent replicates of $4\times10^5$ CLL cell pellets. DNA from four of the eight replicates were eluted into 40 µl elution buffer whereas the other four were eluted into 80 µl which should result in a two fold reduction in the DNA concentration. HT-STELA was performed using the eluted DNA (FIG. 12c). A relatively consistent telomere length distribution profile was observed between the 40 µl eluate replicates and between the 80 µl eluate replicates, with a more intense banding pattern observed in the 40 µl elution compared to the 80 µl elution. Although overall the DNA concentration given by the Nanodrop 3300 (Thermo Scientific) was higher for the 40 µl eluate replicates it was not double the concentration of the 80 µl eluate; indicated that DNA elution is less efficient at 40 µl compared to 80 µl.

Figure 12E:
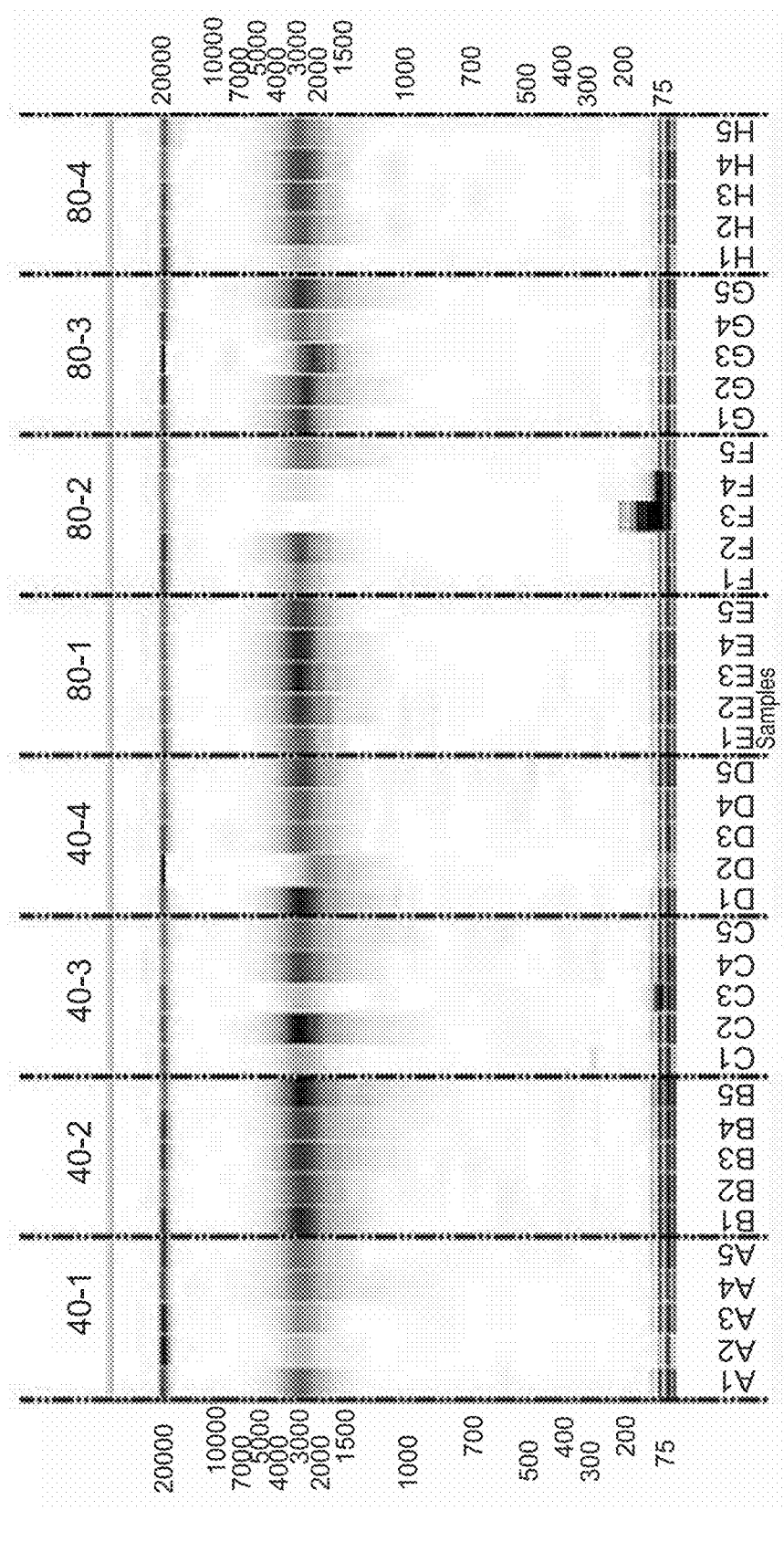
FIG. 12. Optimisation of automated DNA extraction on the Maxwell 16 Instrument using the DNA IQ protocol to generate telomere length distribution smears. (a) STELA was performed on isolated CLL cells. (b) Differing amounts of the same cell population as in (a) were lysed for 1 hour before being loaded into the Maxwell 16 instrument for automated DNA extraction using the DNA IQ protocol. DNA was eluted into 80 µl. After adding tel2 oligonucleotide (250 µM) this DNA/tel2 mix was analysed by HT-STELA. Generated PCR products were resolved and detected on the FRAGMENT ANALYZER™ capillary electrophoresis system (c) DNA was extracted from eight replicates of 4×10⁵ isolated CLL cells using the DNA IQ protocol. Four of the replicates were eluted into 40 µl elution buffer (40-1-40-4) and the remaining four were eluted into 80 µl (80-1-80-4). DNA concentration was measured using the Nanodrop 3300-fluorospectrometer (Thermo scientific). (d) Increasing amounts of DNA (1 µl, 3 µl & 5 µl) extracted from replicate 80-4 were added to multiple HT-STELA PCR reactions to achieve a telomere length distribution smear. (e) Process in (c) was repeated but with 3 µl eluted DNA added to HT-STELA PCR reactions instead of 1 µl.

The relatively consistent telomere length distributions given using DNA extracted from the different eluate replicates from the DNA IQ system was encouraging, however they consisted of a banding pattern as opposed to the desired telomere length distribution smear. In an attempt to achieve this smear an input DNA titration was performed using DNA from one of the replicates (80-4): 1 µl, 3 µl or 5 µl was added to multiple HT-STELA PCR reactions (FIG. 12d). When 1 µl DNA is added per reaction the similar banding pattern to what was seen in FIG. 12c was evident, however when the input DNA was increased to 3 µl and 5 µl a robust telomere length distribution smear was observed (FIG. 12d). HT-STELA was then repeated for all the $4\times10^5$ replicates but with 3 µl DNA added to PCR reactions as opposed to 1 µl (FIG. 12e). Robust telomere length smears were generated instead of banding patterns across all the PCR reactions for every replicate.

These experiments allowed us to optimise the DNA IQ system to provide robust HT-STELA smears.

Validation of HT-STELA in a CLL Patient Cohort

Figure 13C:
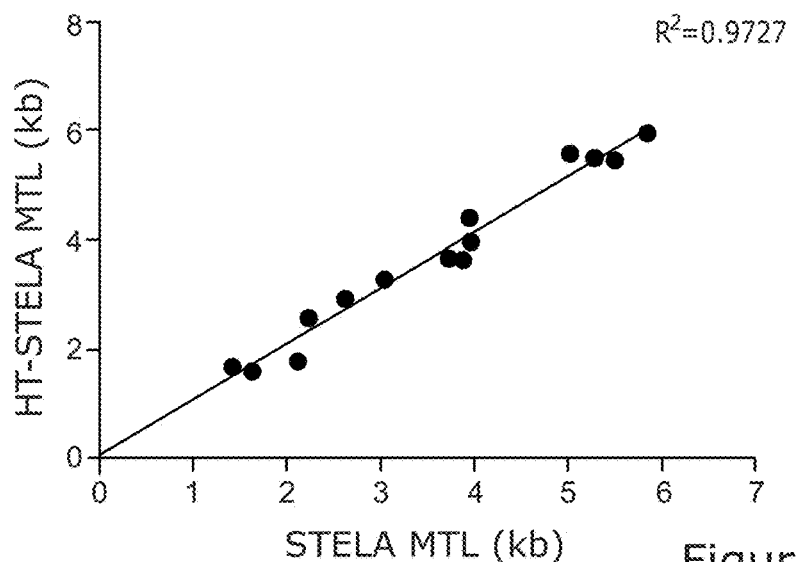
FIG. 13. Analysis of mean XpYp telomere length of CD19+ cells isolated from whole blood of Chronic Lymphoid Leukaemia (CLL) patients CD19+ cells were isolated from whole blood using MACS whole blood CD19 microbeads and the AutoMACS Pro separator (Miltenyi Biotech). DNA was extracted from $4\times10^5$ cells CCD19+cells using the DNA IQ protocol on the Maxwell 16 instrument. Eluted DNA was then used to analyse the mean XpYp telomere length in the CLL patients by (a) STELA or by (b) HT-STELA. (c) Comparison of the mean XpYp telomere length measured by the two techniques.

We tested the HT-STELA system in a cohort of 15 CLL samples. Blood samples were obtained and CD19+ cells purified using MACS whole blood CD19 microbeads and an AutoMACS Pro separator (Miltenyi Biotech). Isolated cells were then counted using a VI-cell instrument (Beckman Coulter) and aliquoted into $4\times10^5$ cell pellets. The cell pellets were lysed for 1 hour and DNA was extracted from the lysates using the DNA IQ protocol Maxwell 16 instrument (Promega) and eluted into 40 µl elution buffer. A portion of this eluted DNA was taken to be analysed by STELA (FIG. 13b) and the rest was used for HT-STELA analysis. Briefly tel2 linker oligonucleotide was added to the eluted DNA to a final concentration of 250 pM and 3 µl DNA/tel2 mix was added to the 30 µl HT-STELA PCR reactions, containing 0.2 uM XpYpE5 and cycled 23 times. The PCR products were resolved and detected using the FRAGMENT ANALYZER™ capillary electrophoresis system (FIG. 13a). Mean XpYp telomere length for each individual reaction was measured using the smear analysis function within the PROSIZE™Data Analysis software and the resulting mean telomere lengths for the three replicates for each patient were combined and averaged giving a final XpYp mean telomere length. For the original STELA method band quantification using Phoretix software (Non-linear Dynamics) was performed and mean XpYp telomere length was subsequently calculated. The mean telomere length measured by both techniques were then compared (FIG. 13c). The output gel from the PROSIZE™Data Analysis software shows that XpYp telomere length distribution smears were generated for 14 of the 15 samples tested. Importantly all the RFU values were greater than the 25 RFU threshold which we had defined as the lower limit from which an accurate reproducible telomere length measurement could be made. The telomere length distributions generated with the HT-STELA and the original STELA methods were remarkably similar (FIG. 13a&b) and the length estimates were significantly correlated (R2=0.97; FIG. 13c).

Patient stratification based on XpYp telomere length determined using STELA together with the fusogenic telomere length threshold, provides high resolution prognostic information for CLL patients (Lin et al., 2014). The entire HT-STELA process from a blood sample of a CLL patient, to the generation of a robust telomere length profile can be performed within 7.5 hours. The development of HT-STELA now facilitates the application of this technology for the routine prognostic assessment of CLL patients, as well as patients with other tumour types for which the prognostic thresholds are informative.

HT-STELA at Additional Chromosome Ends

Once a reproducible HT-STELA assay was developed for the XpYp chromosome end, the technique was developed to allow the measurement of mean telomere length at additional chromosome ends. To achieve specificity for a particular chromosome end telomere-adjacent primers were designed incorporating telomere specific nucleotides at the 3' ends. It is this design parameter which gives specificity to one chromosome end as a mismatch will occur when the primer anneals to other subtelomeric sequences from other chromosome ends that exhibit high levels of sequence homology, resulting in failure of the Taq polymerase to extend from the primer in a PCR reaction and hence failure to produce a PCR product from other telomeres. Using this primer design approach a number of primers were designed for telomere adjacent regions at the 7q and 12q chromosome ends. Several primers specific to the 17p telomere adjacent region were already available as were additional XpYp specific primers. These primers were tested under the same conditions as XpYpE5 to determine whether they could generate telomere length distribution smears using HT1080 cl.2 DNA for their respective chromosome end (FIG. 14).

Figure 16:
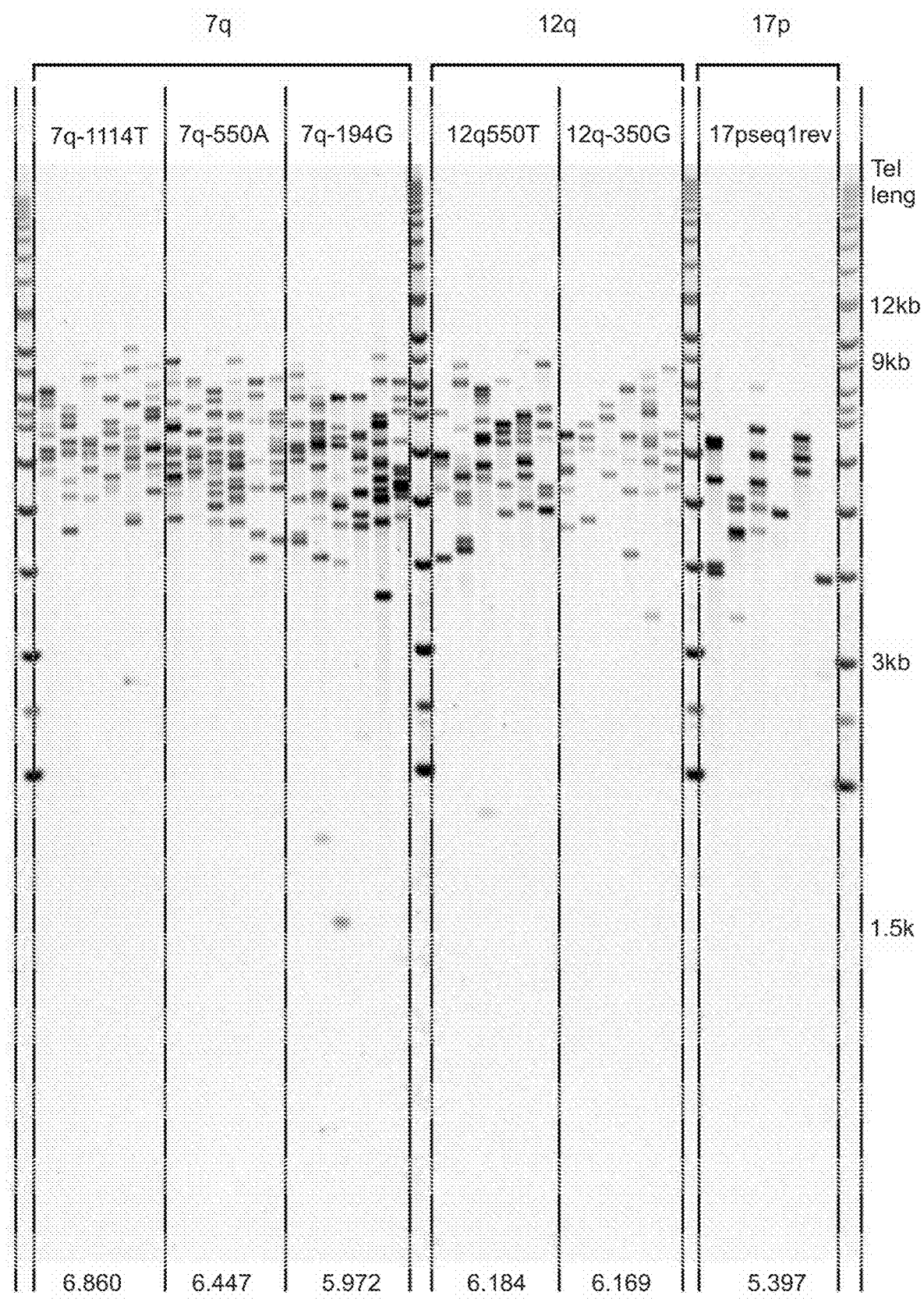
FIG. 16. STELA analysis of 7q, 12q and 17p chromosome ends in HT1080 cl.2 using newly designed primers. Traditional STELA was using HT1080 cl.2 DNA at 7q and 12q chromosome ends using primers designed around the stated telomere-specific nucleotides. 17p STELA was performed using the previously designed 17pseq1rev. PCR product size was quantified using Phoretix software (Nonlinear Dynamics) and mean telomere length was subsequently calculated.

At the 7q chromosome end primers designed around the 7q-specific nucleotides 1115T, 551A, 195G and, to a lesser extent, 29G produced robust telomere length distribution smears (FIG. 14a). The mean molecular weight of the fragments calculated using the smear analysis tool on the PROSIZE™Data Analysis software showed the expected increase that was dependent on the distance from the start of the telomere repeat array. Calculation of the mean telomere length from these telomere length distribution smears by subtracting the distance from the primer to the start of the telomere repeat array resulted in a similar mean telomere length estimate irrespective of the distance from the start of the telomeres. 7q telomere length estimates with HT-STELA were comparable to those determined with the original STELA method (FIG. 14a; FIG. 16).

Figure 14C:
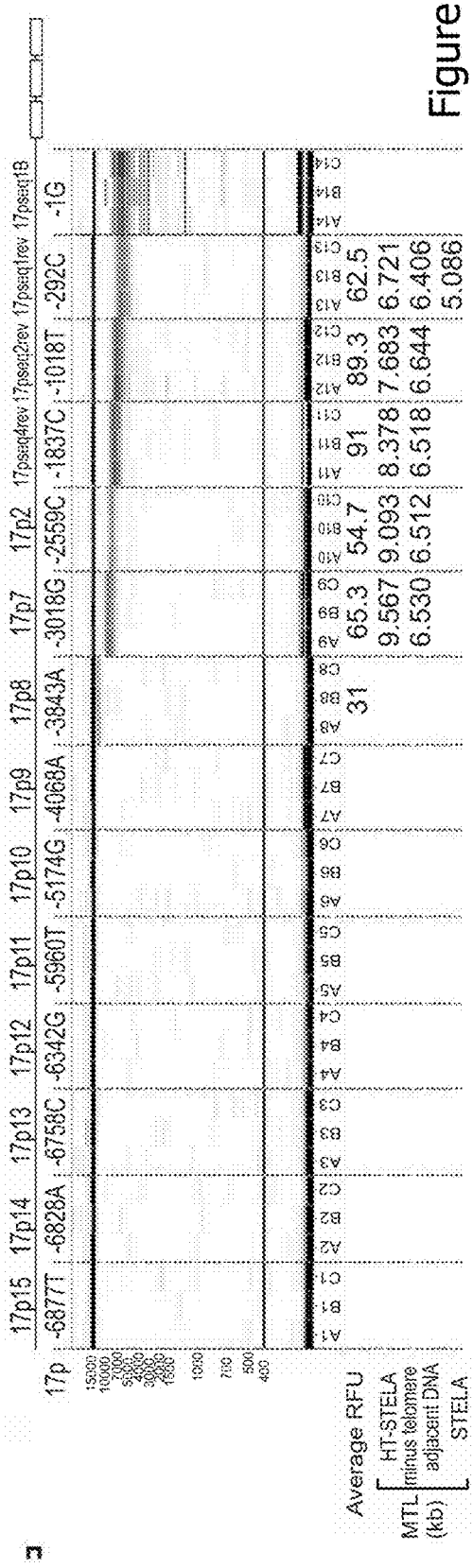
FIG. 14. Development of HT-STELA for 7q, 12q and 17p chromosome ends Numerous chromosome-specific primers were designed within the telomere-adjacent region of (a) 7q and (b) 12q. Primers have previously been designed within the telomere-adjacent region of (c) 17p and (d) XpYp. HT-STELA PCR was performed with these alternative telomere adjacent primers and generated PCR products were resolved and detected on the FRAGMENT ANALYZER™ capillary electrophoresis system. Average RFU (Relative Fluorescence Units) is the calculated mean of the RFU given by each PCR reaction for a given telomere adjacent primer. The identification and position (relative to the TTAGGG repeat start) of the telomere specific nucleotide which is incorporated at the 3' end of the primer is stated for each primer. Distance from the start of the TTAGGG repeats (including the length of the primer) for each primer is subtracted from the molecular weights produced by the FRAGMENT ANALYZER™ capillary electrophoresis system giving the actual telomere length corrected for telomere adjacent DNA. STELA was also performed for each chromosome end. Again, actual telomere length was calculated by subtracting telomere adjacent DNA.

The HT-STELA development for the 12q chromosome end was also successful for some of the primers designed. Primers 350G and 550T (350 & 550 nucleotides from the TTAGGG repeats respectively) generated telomere length distribution smears with comparable RFU values. Like at 7q, the 12q mean telomere length calculated by HT-STELA was very similar to that calculated using the original STELA method (FIG. 14b). The primer designed around the 1388G 12q specific nucleotide produced a very weak telomere distribution. The RFU values for this are too low for a mean telomere length measurement to be given with confidence and will therefore not be used in future experiments Primers had previously been designed specific to the telomere-adjacent region at the 17p chromosome end and a further 8 primers were designed extending up to 6877 bp from the telomere repeat array. All of the primers up to 3843 bp from the telomere repeat tested in HT-STELA yielded smears consistent with telomeric amplification (FIG. 14c). With the exception of 3843 bp (17p8) the HT-STELA smears could be quantified. The smear generated with 17p8 could not be quantified as it was too close to the 15 kb upper marker. Again there was a clear increase in the molecular weight of the amplified products as a function of the distance of the primer from the start of telomere repeat array, which following the subtraction of the telomere-adjacent sequences resulted in a consistent estimation of 17p telomere length from five different 17p primers with a mean of 6.5 kb (FIG. 14c). Interestingly this estimate was greater than that derived with the original STELA method, however as five separate primers yield the same length, we considered that the HT-STELA represented a more robust estimation of telomere length compared to the original STELA method using primer 17pseq1rev. We speculate that this may be related to the use of Southern hybridisation to detect the telomere profiles with the original STELA method and the presence of telomere variant repeats that do not hybridise to the TTAGGG repeat sequence used or the hybridisation probe. These data also showed that robust HT-STELA profiles were generated using primers at least as far as 3.843 kb from the start of the telomere repeat array. All the 17p specific primers produced robust telomere length distributions with the exception of 17pseq1B located 1 nucleotide from the telomeric repeat tract. When this primer was used in HT-STELA a ladder-like distribution was observed that was not consistent with the robust amplification of a telomere (FIG. 14c). Interestingly the performance of a telomere adjacent primer seems to be diminished if it located less 30 nucleotides from the telomeric repeat tract. Both 7q29G and 17pseq1B performed poorly compared to other primers designed further from the telomeric repeat tract at their respective chromosome ends.

Figure 14D:
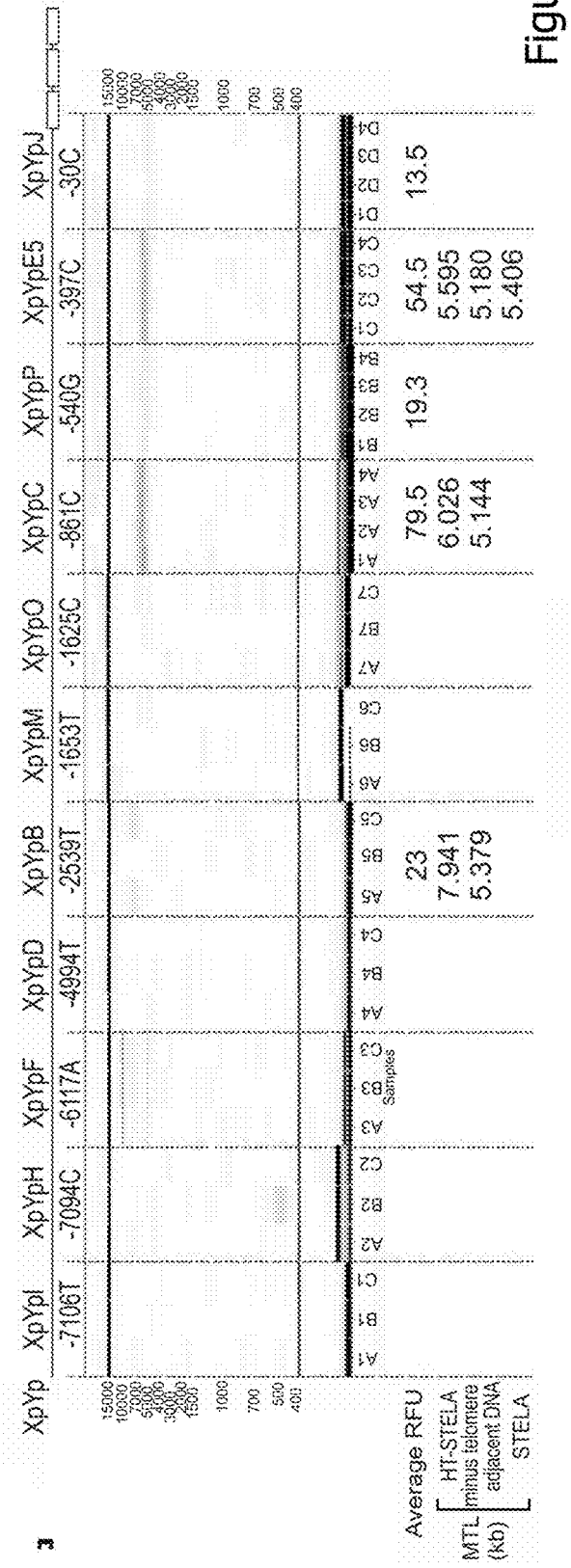

The success of the XpYp telomere adjacent primers was more varied compared to that observed at the 17p telomere. XpYpM and XpYpO (1653 and 1625 nt from TTAGGG respectively), or primers XpYpD, XpYpF, XpYpH and XpYpI all greater than 4.8 kb from the telomere, did not generate any PCR product whatsoever (FIG. 14d). As expected XpYpE5 produced a telomere length distribution smear with a mean telomere length similar to what was generated using the original STELA method. XpYpB (2539 bp from the telomere) produce a smear of the expected size. XpYpC also produced a similar telomere length distribution, but with a higher RFU value than XpYpE5 suggesting that XpYpC is more efficient at generating XpYp telomere products and therefore XpYpC and could be used instead of XpYpE5 for subsequent XpYp HT-STELA (FIG. 14d). XpYpJ also produced a telomere length distribution smear however it was very weak. Like 7q29G and 17pseq1B, XpYpJ is located less than 30 nt from the telomeric repeat tract and has failed to produce a robust telomere length distribution smear suggesting that there is a lower limit distance from the TTAGGG repeat tract below which primers cannot be designed which can sufficiently amplify telomeres.

These data demonstrate that HT-STELA can be applied to additional chromosome ends and that primers up to at least 3.843 kb from the start of the telomere repeat array yield robust telomere profiles. However it was also apparent that primers within 30 bp of the telomere did not produce efficient or specific amplification.

Simplifying Target Amplification

The telomere lengths observed in samples derived from peripheral blood of normal individuals as detailed above can display considerable heterogeneity, with a diverse range of lengths ranging from close to zero to 25 kb or more. This can occasionally present a particular problem for PCR based amplification of telomeres, whereby the shorter telomeres are likely to amplify more efficiently than the longer telomeres, resulting in an underestimate of mean telomere length.

In such circumstances, we tested the concept of pre-digesting DNA with a restriction enzyme prior to HT-STELA, the idea being that it will reduce the complexity of the input DNA by digesting the non-telomeric DNA and provide a simpler target for amplification.

DNA samples were extracted and digested with the restriction enzyme as detailed in the Material and Methods. The choice of enzyme will depend upon the nature of the telomere repeat array to be amplified and it will be necessary to ensure that it does not cut between the 5' end of the oligonucleotide primer and chromosome telomere end. As proof of principle EcoR1 was chosen because it does not cut DNA between the 5' end of the XpYpC primer used for HT-STELA and the telomere repeat array, such that non-telomeric loci and other telomeres maybe cut, but the XpYp telomere will remain intact. Other enzymes could also conform to this specific requirement.

Figures 17A, 17B:
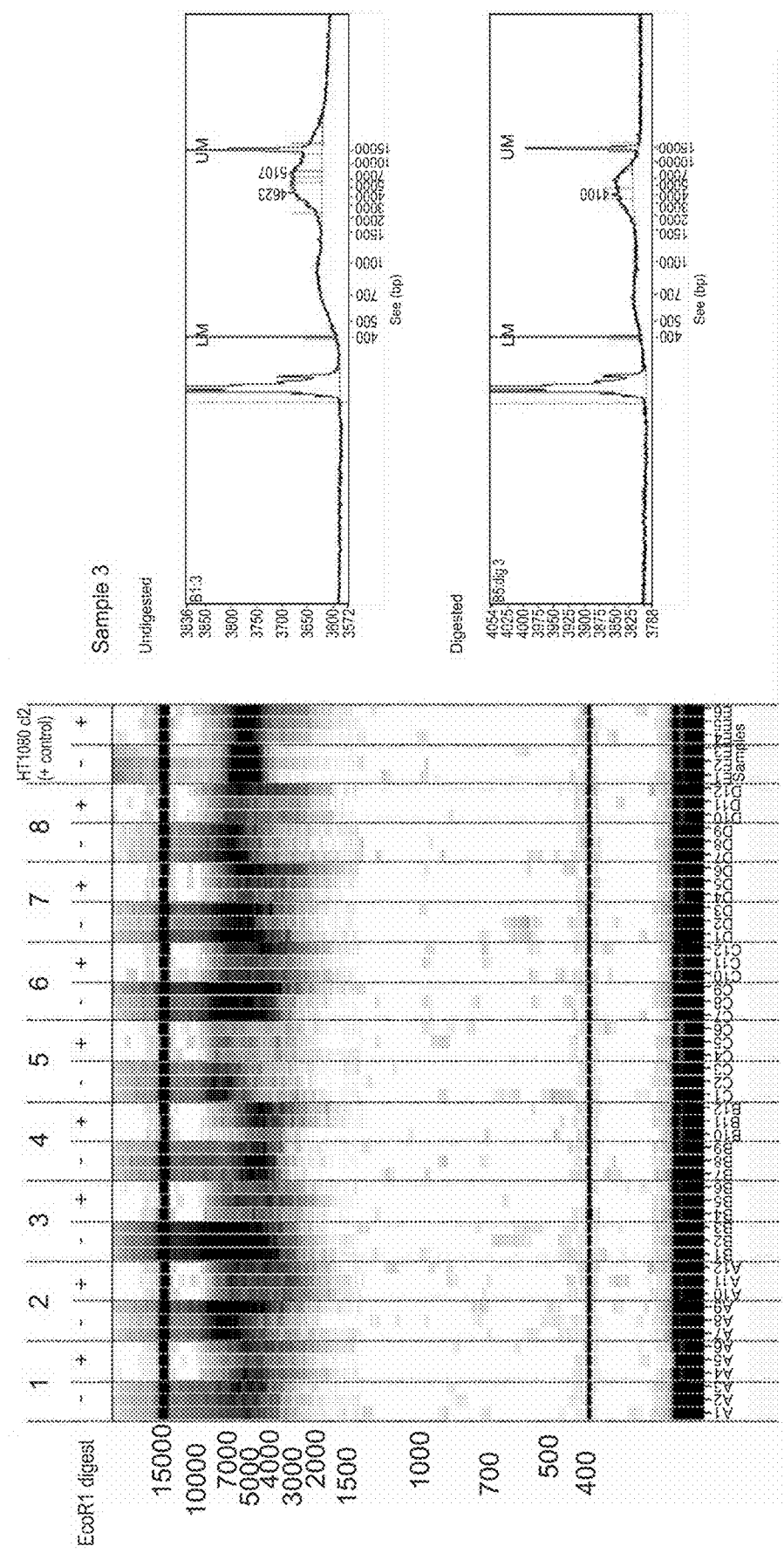
FIG. 17. Digestion of DNA with EcoR1 prior to HT-STELA PCR results in reduced background noise and a cleaner HT-STELA electropherogram (a) DNA extracted from eight peripheral blood samples was digested with EcoR1 for 2 hours. Digested DNA was then added to triplicate HT-STELA PCR reactions and cycled for 23 PCR cycles. Parallel reactions were also constructed which contained undigested DNA of the same samples. The resulting PCR products were then separated by capillary electrophoresis using the FRAGMENT ANALYZER™ capillary electrophoresis system. (b) Comparison of the electropherogram generated from one HT-STELA PCR reaction amplifying the (i) undigested or (ii) digested DNA of sample 3 from (a).

The DNA samples with, or without, EcoR1 digestion were subjected to HT-STELA and analysed with a FRAGMENT ANALYZER™ capillary electrophoresis system (FIG. 17). It was apparent that EcoR1 digestion prior to a HT-STELA successfully reduced the background signal, resulting the improved definition of the telomere smear.

Figure 18:
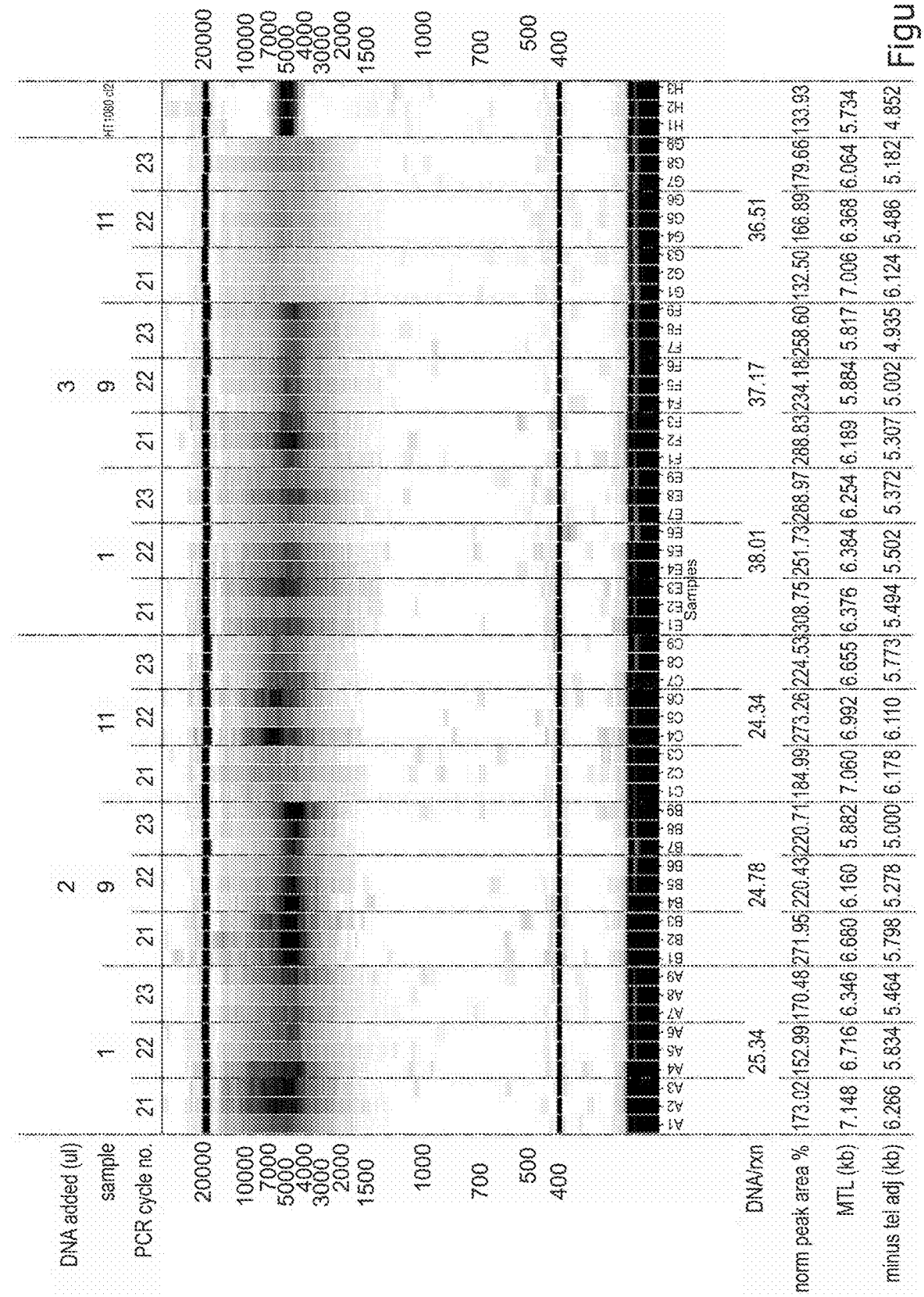
FIG. 18. Optimising PCR cycle number and DNA input amount. DNA extracted from three peripheral blood samples (1, 9 & 11) was digested with EcoR1 for 2 hours. Following digestion DNA was quantified and either 2 ul or 3 ul of digested DNA was added to three sets of triplicate HT-STELA reactions. Each set of triplicate reactions were cycled for 21, 22 or 23 PCR cycles. Resulting PCR products were then resolved by capillary electrophoresis using the FRAGMENT ANALYZER™ capillary electrophoresis system. Mean telomere length was calculated for each lane using the smear analysis tool within the PROSIZE™Data Analysis software. Telomere adjacent DNA (distance between the PCR assay start and the start of the telomere repeat array) was removed giving a final mean telomere length. Norm peak area % was calculated by using the formula (Tel peak area/LM peak area)*100 where Tel peak area=area under a telomere length distribution smear peak on an electropherogram in PROSIZE™Data Analysis software. LM peak area=peak area under lower marker peak on electropherogram.

Further experiments were undertaken to test the conditions for amplification, by titrating the numbers of PCR cycles and the amount of EcoR1 digested input DNA (FIG. 18). It was clear from these experiments that an input DNA amount of 25 ng and 21-23 PCR cycle were optimal.

Adaptation of HT-STELA for Pre-Purified DNA Samples

The above methodology was established for the analysis of telomere length in fresh/frozen cell and tissue samples obtained from either haematological or solid tumours. We next explored the ability to explore the technology using alternative DNA sample platforms, specifically previously extracted DNA samples. The ability to analyse previously extracted DNA samples expands the utility of HT-STELA, by for example, allowing the analysis of patient cohorts from clinical trials many of which will only have tumour DNA samples available, or indeed the analysis of any archived DNA sample.

The conditions under which the DNA IQ system is saturated by DNA was determined. To do this increasing amounts (200, 500, 1000 and 2000 ng) of HT1080 cl2 DNA was added to DNA IQ lysis buffer and DNA extracted using the standard protocols on the Maxwell instrument (Promega). This was performed twice: once using the DNA IQ casework pro kit (used when extracting DNA from CLL cell pellets) and also using the DNA IQ reference kit (FIG. 19). The two kits differ in that a low elution volume (LEV) protocol is used with the casework pro kit whereas a standard elution volume (SEV) protocol is used with the reference sample kit. DNA is eluted into 80 μl using the casework pro kit and into 300 μl using the reference sample kit.

Differing amounts of eluted DNA was then tested in HT-STELA reactions. For the casework pro kit samples either 3, 6 or 9 μl eluted DNA was added for each input DNA quantity added to the DNA IQ system. For the reference sample kit, due to the larger elution volume, 3, 10 and 20 μl of eluted DNA was added to HT-STELA reactions. Again this was performed for each DNA quantity added to the DNA IQ system. The HT-STELA reactions were then subject to PCR under the same conditions as previously described and the resulting PCR products were resolved by capillary electrophoresis using the FRAGMENT ANALYZER™ capillary electrophoresis system (FIG. 19).

The quantity of DNA added to the DNA IQ casework pro kit cartridges had little impact on the resulting telomere length distribution smears. Whether adding 200, 500, 1000 or 2000 ng to the system the resulting telomere length distribution smears appeared similar both in terms of MTL and normalised tel peak area % suggesting that the system is already at saturation point when 200 ng is added to it (FIG. 19a). A factor which made more of an impression on the final telomere length distribution smear was the amount of eluted DNA added to HT-STELA reactions. The increase in DNA quantity added to HT-STELA reactions is reflected by the increase in signal intensity of the telomere length distribution smears for each DNA quantity set and for both kit types. For the DNA IQ casework pro kit, regardless of input DNA quantity, adding 6 μl or less of the eluted DNA to the HT-STELA PCR reactions is not sufficient to generate a telomere length distribution smear with a normalised tel peak area % higher than the lower 25% threshold that we had previously defined as a quality threshold. Adding 9 μl of eluted DNA to HT-STELA reactions produced a more robust telomere length distribution smears which, with exception of the 500 ng samples, surpassed the lower normalised tel peak area % threshold. The MTL given by all of the 9 μl replicates ranged from 6.084-6.357 kb which is comparable to the HT1080 cl2 positive control MTL of 6.368 kb.

Unlike the DNA IQ casework pro kit, the input DNA amount added to the DNA IQ reference sample cartridges affected the telomere length distribution smears observed on the HT-STELA output gel (FIG. 19b). Adding DNA eluted from 200 ng of input DNA into the HT-STELA reactions resulted in barely detectable telomere length distribution smears regardless of how much of the DNA was added to the reactions. Only when input DNA amount was increased to 500 ng and above did the telomere length distribution smears become apparent. However this only occurred when 10 μl or more eluted DNA was included in the HT-STELA reactions. This suggests that the DNA IQ system using the reference sample kit is not saturated using these DNA quantities. The only HT-STELA reaction that generated sufficient signal to surpass the 25% normalised tel peak area lower threshold, was when 20 μl of the DNA eluted from the 2000 ng DNA input was added to the HT-STELA reactions. Although this generated an HT-STELA signal of sufficient intensity and with an accurate MTL (6.224 kb), however these conditions are not practical as too much DNA (2000 ngs) was required to generate a reliable signal. Thus DNA normalisation performed with the DNA IQ casework pro kit was preferred to the DNA IQ reference sample kit.

Figures 20A, 20B:
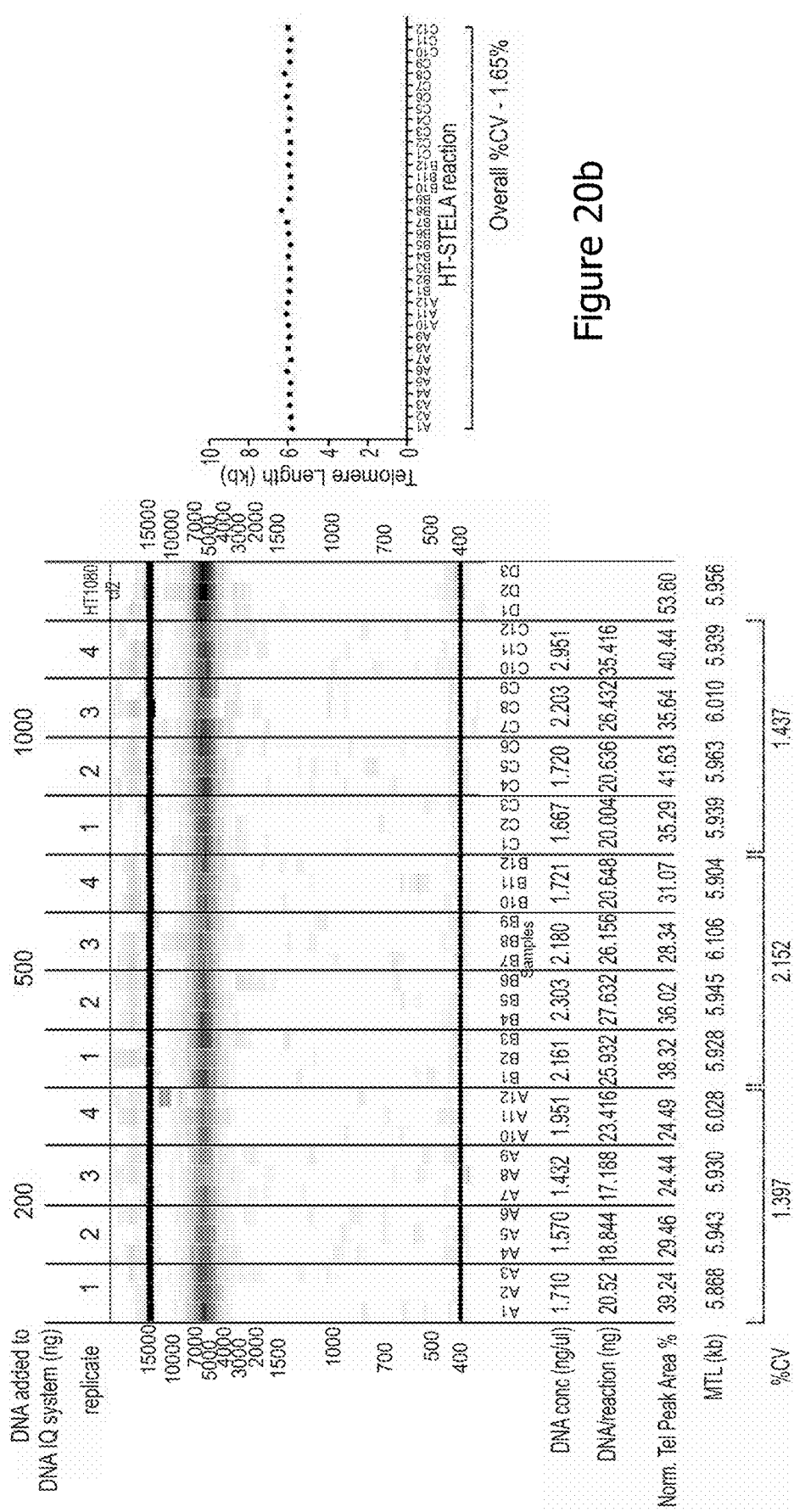
FIG. 20. Testing the reproducibility of the DNA clean up and normalization procedure using the DNA IQ Casework Pro kit (a) 200, 500 or 1000 ng DNA was added to DNA IQ casework pro kit cartridges. The purification of each DNA quantity was performed four times. DNA was eluted into 80 ul elution buffer. 12 ul of eluted DNA was added to triplicate HT-STELA reactions and subject to 23 PCR cycles. PCR products were resolved and detected on the FRAGMENT ANALYZER™ capillary electrophoresis system. DNA concentration was measured in triplicate with picogreen using the nanodrop 3300 fluorospectrometer. (Tel peak area/LM peak area) %=(area under a telomere length distribution smear peak on an electropherogram/peak area under lower marker peak on electropherogram)*100. Mean telomere length (MTL) was calculated for each HT-STELA reaction triplicate using the smear analysis tool within the PROSIZE-™Data Analysis software. Coefficient of variance (% CV) was calculated using the formula % CV=(SD/MTL)*100. (b) Comparison of mean telomere length calculated from the telomere length distribution smears generated from individual HT-STELA reactions. Coefficient of variation was calculated in the same manner as in (a)

Our data showed that adding 9 μl of eluted DNA from the DNA IQ casework pro kit with input DNA greater than 200 ngs resulted in telomere length distributions that yielded an accurate MTL and were above the 25% lower tel peak area % threshold. However the tel peak area % was only marginally above the lower 25% threshold (mean 26%). For this reason and to test the reproducibility of the system a follow up experiment was performed in which either 200 ng, 500 ng or 1000 ng DNA was added to the DNA IQ casework pro system (FIG. 20a). Each DNA quantity had four replicates. In an attempt to increase the signal intensity and thereby the robustness of the HT-STELA assay 12 μl of eluted DNA was added to HT-STELA reactions instead of the 9 μl used previously. The HT-STELA reactions were then subject to PCR and resulting PCR products were resolved by capillary electrophoresis. FIG. 20a shows that the increase in DNA made the assay more robust with an increased tel peak area %. Although for two of the replicates (200-3 & -4) this value is still slightly below the lower 25% threshold, for the rest of the replicates it exceeds the threshold. The tel peak area % range increased with a range of 24.44 to 41.63% with a mean of 34% whereas when 9 μl eluted DNA was added per reaction the range was 19.04-27.2% with a mean of 26%.

The XpYp mean telomere length measured from the PCR products generated from the normalised DNA samples was accurate ranging from 5.868 kb-6.106 kb which spans the 5.956 kb measured MTL of the positive control HT1080 cl2 DNA. This MTL range gave an overall coefficient of variance of 1.65% (FIG. 20b). The % CV between the input DNA quantity replicates was similarly very low—1.397% for 200 ng, 2.152% for 500 ng and and 1.473% for 1000 ng.

Together these experiments demonstrate that DNA samples containing 200 ng DNA or more can be normalised using the DNA IQ casework DNA extraction kit in conjunction with the Maxwell 16 DNA extraction system thereby negating the need for time consuming DNA quantification. Furthermore adding 12 μl of this eluted DNA to HT-STELA reactions can produce robust and reliable telomere length distribution smears from which highly accurate mean telomere length can be measured.

Adaptation of HT-STELA for DNA Sample Cards

We also explored the adaptation of HT-STELA to allow the analysis of blood samples stored on sample cards (such as Whatman® FTA/FTA Elute cards). FTA cards are a commonly used format for the convenient sampling and storage of blood samples for subsequent downstream DNA analysis. It provides a quick method for patients that may require a telomere test, to provide a sample at home, without the requirement of a clinician or phlebotomist. A small blood sample is spotted onto an FTA card then returned to the testing facility by standard mail services. This will also have utility in the analysis of trial cohorts that have samples stored on FTA card.

To test the system, 125 μl blood from three CLL patients was spotted onto FTA cards and allowed to air-dry overnight. The three patients had differing white blood cell (WBC) counts; patient 71 had a WBC count of $45 \times 10^6$ cells/ml whereas patient 74 had a count of $6 \times 10^6$ cells/ml and patient 75 had a WBC count of $101 \times 10^6$ cells/ml. The rationale behind attempting this procedure with patients with differing WBC counts was that it would give an indication as to the lower limit WBC count which would provide enough cells and hence enough DNA to be extracted for a reliable, robust telomere length distribution smear to be generated.

Figure 21A:
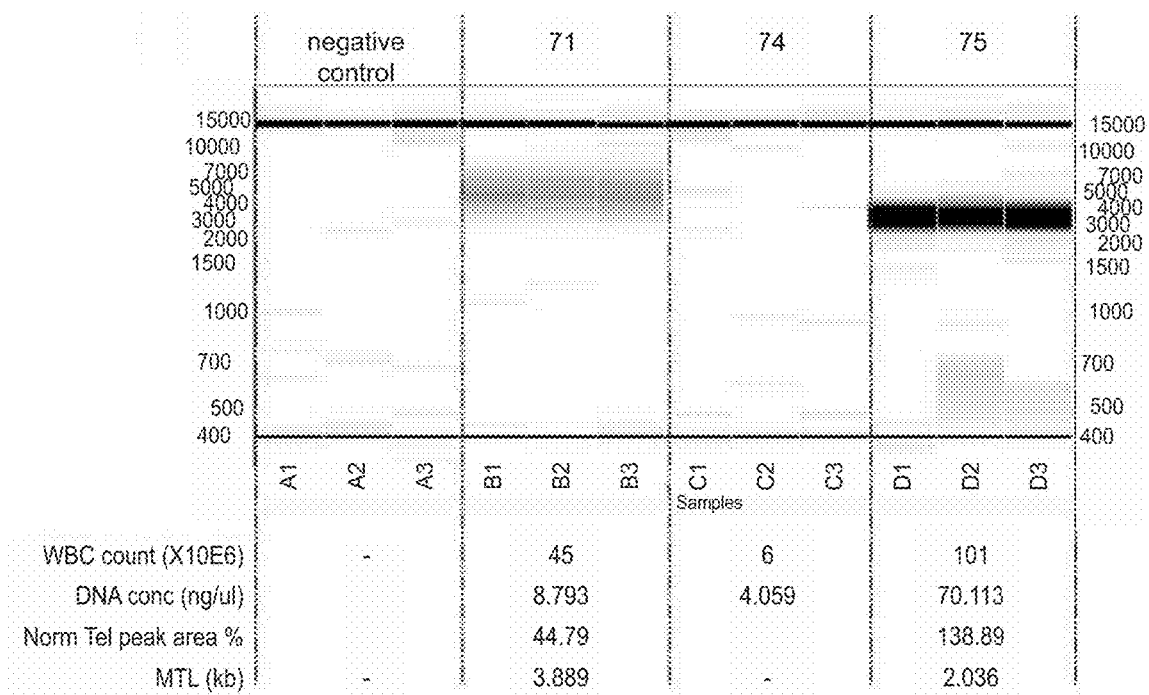
FIG. 21. FTA STELA analysis of DNA extracted from the dried blood of CLL patients (a) DNA was extracted from two 3 mm punches of an FTA card sampling area saturated with 125 ul blood for each patient or containing no blood (negative control). The punches were incubated in Casework Extraction buffer (Promega) for 1 hour at 65° C. with shaking (1400 rpm) after which DNA was extracted from the eluted cell lysate using the LEV blood cartridges. DNA concentration was measured using the NanoDrop 3300 fluorospectrometer. HT-STELA PCR was performed using 3 ul DNA per reaction. Generated PCR products were resolved by capillary electrophoresis using the FRAGMENT ANALYZER™ capillary electrophoresis system. Mean telomere length was calculated for each lane using the smear analysis tool within the PROSIZE™Data Analysis software. Normalised tel peak area % was calculated using the formula (tel peak area/lower marker peak area)×100. Peak areas are stated in the PROSIZE™Data Analysis software. (b) The process in (a) was repeated however the DNA from the eluted cell lysate was extracted using the DNA IQ casework pro cartridges. (c) The process in (b) was repeated for 26 CLL patient blood samples collected. STELA was also performed for these patients and the MTL calculated by the two methods of analysis was compared.

DNA was extracted from two 3 mm punches of a dried blood spot with casework extraction buffer (Promega) for 1 hour at 65° C. with shaking at 1400 rpm. The eluted blood cell lysates were then separated from the stripped punches and DNA was extracted with the Maxwell automated DNA extraction system using the LEV blood kit. Negative control punches were also included (FTA card with no blood). As stated in the protocol (Promega) LEV blood cartridges were used for the DNA extraction and DNA was eluted into 50 μl elution buffer. 3 μl of eluted DNA was added to each HT-STELA reaction in the same manner as previously mentioned. These reactions were then subject to 23 rounds of PCR amplification and the DNA fragments resolved with the FRAGMENT ANALYZER™ capillary electrophoresis system (FIG. 21a). As expected the negative control did not produce any PCR products. However telomere length distribution smears were generated from DNA extracted from the dried blood of patients 71 and 75. The calculated mean telomere length (MTL) of these patients using this FTA-STELA method was very similar to MTL measured by STELA: for patient 71 the MTL for FTA-STELA was 3.889 kb compared to 4.169 kb measured by STELA. Similarly, for patient 75 the FTA-STELA derived MTL 2.036 kb was very similar to the STELA MTL of 1.856 kb. No telomere length distribution profile could be generated for patient 74. This doesn't appear to be due to the low WBC count ($6 \times 10^6$ cells/ml) as the number of cells on two 3 mm punches of this dried blood spot was estimated to contain $7.5 \times 10^4$ cells which, although less than the than the $4 \times 10^5$ cells required to produce robust telomere length profile, there should still have been sufficient DNA to yield a detectable profile (FIG. 12b). Alternatively this negative result may be due to a technical issue that occurred within the experiment. The number of cells on two 3 mm punches of the dried blood spots of patients 71 and 75 was estimated to be $5.63 \times 10^5$ and $1.575 \times 106$. This difference in cell number is reflected not only in the difference in concentration of the eluted DNA (71-8.793 ng/μl, 75—70.113 ng/μl) but also in the tel peak area % of the telomere length distribution smears of the two patients (71—44.79%, 75—138.89%).

Large differences in both the concentration of the eluted DNA and the tel peak area % generated from the telomere length distribution smears was observed between the different samples analysed (FIG. 21a). We therefore tested DNA IQ Casework Pro kit in an attempt to normalise the DNA eluted from the FTA card extracts. We have previously shown that the number of cells known to saturate the DNA IQ system and therefore normalise DNA concentration is $4 \times 10^5$. We estimated that this cell number would be present on two 3 mm punches of a dried blood spot from a patient with a WBC count of $32 \times 10^6$ cells/mi. It was also likely however, that a telomere length distribution smear could still be generated from patients with a WBC count as low as $16 \times 10^6$ cells/ml a two 3 mm FTA card punches from such a patient was estimated to contain $2 \times 10^5$ cells, a cell number that we have previously shown to produce a HT-STELA profile (FIG. 12b). To test this an additional patient was included in the analysis: Patient 89, with a WBC count of $20 \times 10^6$ cells/ml. DNA was extracted from the dried blood spot of this patient as well as from the FTA sample of patient 91 (WBC count—69×10⁶ cells/ml), together with patients 71 and 75. Patient 74 was discounted as a telomere length profiles could not be achieved with either STELA, HT-STELA or FTA STELA.

Figure 21B:
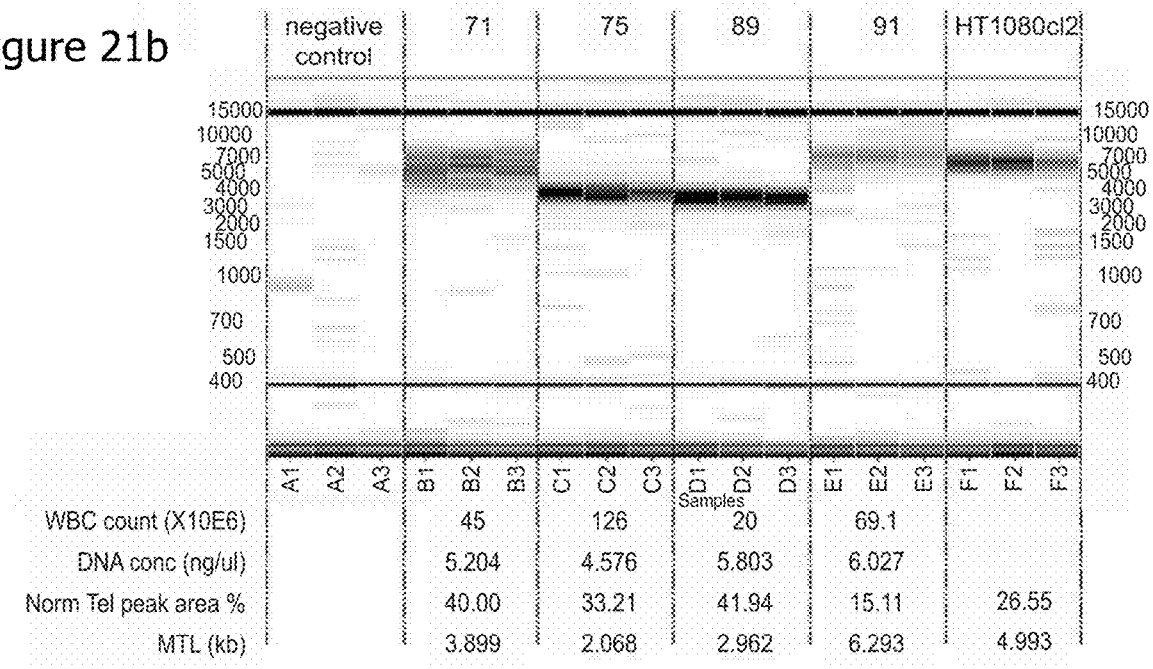

The concentrations of the eluted DNAs indicate that the DNA IQ system successfully normalised the DNA eluted from each of the samples (FIG. 21b). The DNA concentration ranged from 4.576 to 6.027 ng/µl, a lower range than observed when DNA was extracted using the LEV blood kit. Telomere length distribution smears were generated from all four eluted DNA samples (FIG. 21b). Three of these four telomere length distribution smears were robust and exceeded the 25% lower threshold for tel peak area %. One of these robust telomere length distributions was generated from DNA extracted from the dried blood of patient 89 (WBC count—20) indicating that patients with a WBC count less than 32×10⁶ can have XpYp MTL measured by FTA-STELA. The lower limit of WBC count for FTA-STELA is still unknown and will require elucidation in future assays. The MTL measured by FTA-STELA for patient 89 was 2.962 kb, very similar to the MTL measured by STELA (2.75 kb). The FTA-STELA MTL of patients 71 and 75 were similarly accurate: Patient 71 FTA-STELA MTL was 3.889 kb compared to 4.169 as measured by STELA. Likewise patient 75 FTA-STELA MTL of 2.068 kb was very similar to the STELA MTL of 1.856 kb.

A less intense telomere length distribution smear was generated from the DNA extracted from the dried blood spot of patient 91 as reflected by the reduced tel peak area % (FIG. 21b). A reduction in signal intensity has previously been shown to result in a decrease in accuracy in measuring mean XpYp telomere length and also increases variation between biological replicates (FIG. 11). Indeed reduced accuracy in MTL measurement was seen in this sample as the FTA-STELA MTL of 6.293 kb is a significant overestimation compared to the STELA measurement of 5.008 kb.

Figure 21C:
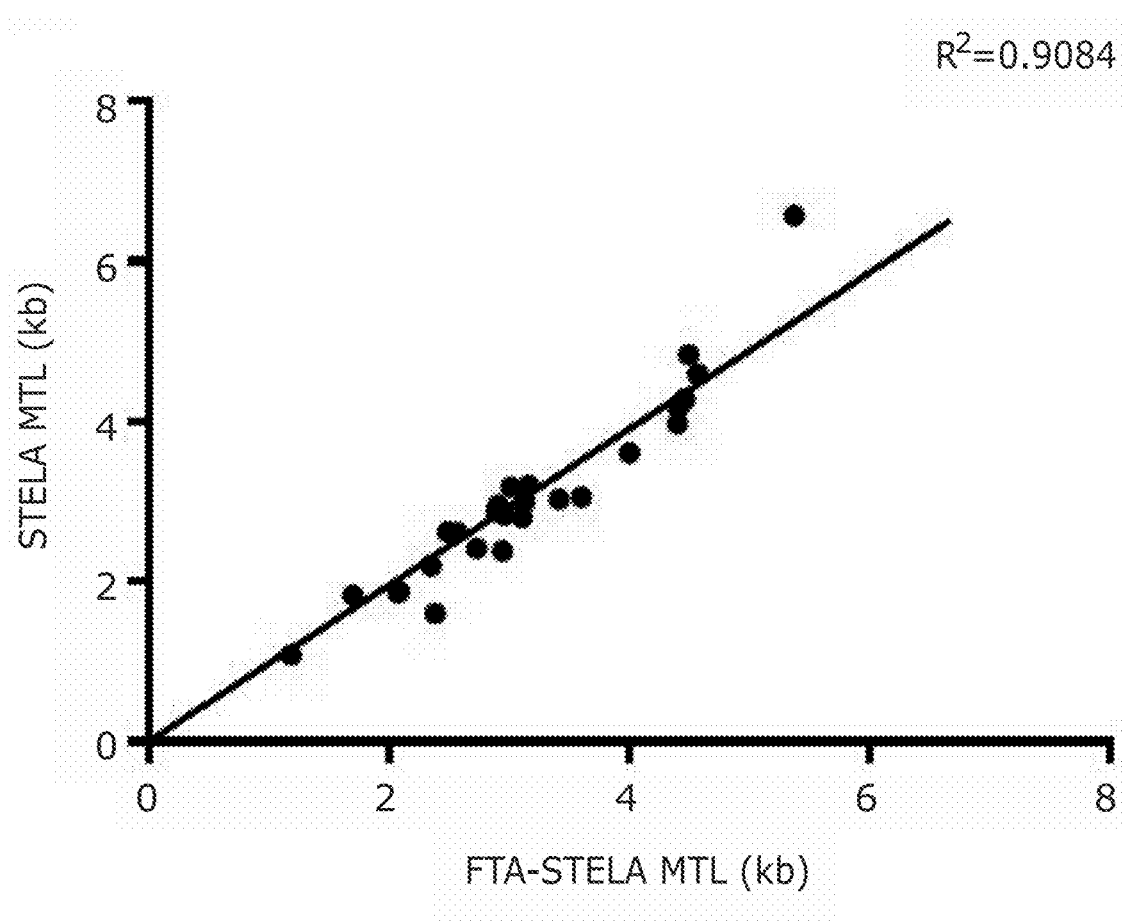

Given the success of generating robust telomere length profiles from CLL patients blood samples stored on FTA cards, we undertook a larger study to test the ability of FTA-STELA to accurately measure mean XpYp telomere length in CLL patients. FTA STELA was performed in parallel with STELA on a cohort of CLL patients and mean XpYp telomere length measured by both techniques was compared. In total DNA was extracted from the dried blood of 26 CLL patients. FTA-STELA was performed and the resulting MTL measured was compared to the MTL generated with HT-STELA (FIG. 21c). A clear correlation between the MTL determined with both techniques was observed (R2=0.9084) suggesting that FTA-STELA can be used to measure mean XpYp telomere length in CLL patients accurately.

We have shown that the HT-STELA method can be adapted for the analysis of blood samples stored on FTA cards, this method will likely be applicable to other card based sample storage systems. This adaptation will provide considerable additional utility to the HT-STELA method by allowing patients to use standard self-sampling kits and send these direct to the testing facility for analysis. This will provide considerable cost savings in terms of blood sample acquisition and upstream processing.

SUMMARY

Telomere length analysis, as representative of telomere dysfunction, provides a highly prognostic tool in human diseases, permitting considerable discrimination for clinical outcome following treatment. Moreover, prognostic power should enable clinicians to confidently predict the clinical course of these diseases and tailor treatments accordingly.

Therefore, a reliable method for measuring telomere length in a high throughput context represents a significant contribution to the ability of clinicians to determine, manage and treat telomere shortening illnesses.

REFERENCES

16. Capper R, Britt-Compton B, Tankimanova M, et al. The nature of telomere fusion and a definition of the critical telomere length in human cells. Genes Dev. 2007; 21:2495-508.
17. Letsolo B T, Rowson J, Baird D M. Fusion of short telomeres in human cells is characterised by extensive deletion and microhomology and can result in complex rearrangements. Nucleic Acids Res. 2010; 38:1841-52.
18. Cawthon, R. M. Telomere measurement by quantitative PCR. Nucleic Acids Res. 2002; 30; e47.
19. Shen, J., Terry, M. B., Gurvich, I., Liao, Y., Senie, R. T. and Santella, R. M. Short telomere length and breast cancer risk: a study in sister sets. Cancer Res. 2007; 67: 5538-5544. Reviewed in Aviv, A. The epidemiology of human telomeres: faults and promises. J Gerontol A Biol Sci Med Sci, 2008; 63: 979-983.
20. Baird D M, Rowson J, Wynford-Thomas D, Kipling D. Extensive allelic variation and ultrashort telomeres in senescent human cells. Nat Genet. 2003; 33:203-7.
21. Britt-Compton B, Rowson J, Locke M, Mackenzie I, Kipling D, Baird D M. Structural stability and chromosome-specific telomere length is governed by cis-acting determinants in humans. Hum Mol Genet. 2006; 15:725-33.
22. Capper R, Britt-Compton B, Tankimanova M, et al. The nature of telomere fusion and a definition of the critical telomere length in human cells. Genes Dev. 2007; 21:2495-508.
23. Letsolo B T, Rowson J, Baird D M. Fusion of short telomeres in human cells is characterised by extensive deletion and microhomology and can result in complex rearrangements. Nucleic Acids Res. 2010; 38:1841-52.
24. Lin T T, Norris K, Heppel N H, Pratt G, Allan J M, Allsup D J, Bailey J, Cawkwell L, Hills R, Grimstead J W, et al. Telomere dysfunction accurately predicts clinical outcome in chronic lymphocytic leukaemia, even in patients with early stage disease. Br J Haematol 2014. 10.1111/bjh.13023
25. WO2013/024264
26. (Wagner et al., Nature Biotechnology 14:840-844, 1996)
27. Roger L, Jones R E, Heppel N H, Williams G T, Sampson J R, Baird D M. Extensive telomere erosion in the initiation of colorectal adenomas and its association with chromosomal instability. J Natl Cancer Inst 2013; 105:1202-11.

TABLE 1

| Chromosome end | Primer name | Genomic Coordinates (HG38) | Sequence |
|---|---|---|---|
| 2p | 2p2 | chr2: 10755 | GAGCTGCGTTTTGCTGAGCAC (SEQ ID NO: 1) |
| 4q | 4qK1 | chr4: 190122098 | ACGGTGGCATGCCTCTCTC (SEQ ID NO: 2) |
| 4p | 4p4 | chr4: 10457 | TCTGCGCCTGCGATGGCGCTATG (SEQ ID NO: 3) |
| 5p | 5p3 | chr5: 12240 | GCATTCTCTTCACCACAGATGTTG (SEQ ID NO: 4) |
| 7q | 7q1533C | chr7: 159334337 | CCCACACAGTCATCTATTGTT (SEQ ID NO: 5) |
|  | 7q1115T | chr7: 159334755 | GAGGTGCAGTAGTGGGGATCTAACT (SEQ ID NO: 6) |
|  | 7q843T | chr7: 159335027 | GGGACAGCATATTCTGGTTT (SEQ ID NO: 7) |
|  | 7q551A | chr7: 159335319 | GCACAGCCTTTTGGGGTACCA (SEQ ID NO: 8) |
|  | 7q195G | chr7: 159335675 | AGTGGGAGATCCACACCGTAGCGTG (SEQ ID NO: 9) |
|  | 7q29G | chr7: 159335841 | CCaTGCAGTGCTAAGACAGCAATGAG (SEQ ID NO: 10) |
| 11q | 11q13B | chr11: 135076467 | CAGACCTTGGAGGCACGGCCTTCG (SEQ ID NO: 11) |
| 12q | 12q1511C | chr12: 133263363 | CCTCTGGTCATTATGAATAGGGCTTC (SEQ ID NO: 12) |
|  | 12q1387G | chr12: 133263487 | GGGGAAAAAATGCCCAAG (SEQ ID NO: 13) |
|  | 12q1036C | chr12: 133263838 | CCTTCTCTTCTTGATGTC (SEQ ID NO: 14) |
|  | 12q550T | chr12: 133264324 | ACAGCCTTTTGGGGTACCGT (SEQ ID NO: 15) |
|  | 12q350G | chr12: 133264524 | GGCTTCATTGATGGTGAATACAATCG (SEQ ID NO: 16) |
|  | 12q319G | chr12: 133264555 | GCAGCGCTGAATATTCAGGGTG (SEQ ID NO: 17) |
| 16p | 16prev1 | chr16: 10241 | CACTTATTAGTTCCAGTCTCTG (SEQ ID NO: 18) |
| 17p | 17p8 |  | AGAAGCAGCGAGGAGCTTCA (SEQ ID NO: 19) |
|  | 17p7 |  | CCTGGCATGGTATTGACATG (SEQ ID NO: 20) |
|  | 17p2 |  | GCTAGGAATGGAATCATTGACTC (SEQ ID NO: 21) |
|  | 17pseq4rev |  | GATACTGGGAGGATCATATCTGGC (SEQ ID NO: 22) |
|  | 17pseq2rev |  | CCATTAGCCTGTGGGGTCTGAT (SEQ ID NO: 23) |
|  | 17pseq1rev |  | GAATCCACGGATTGCTTTGTGTAC (SEQ ID NO: 24) |
|  | 17pseq1B |  | AAGCAGGTTGAGAGGCTGAGG (SEQ ID NO: 25) |
| 18q | 18qrev4M | chr18: 80262147 | CACAGGGATGGTTAGGTATCTC (SEQ ID NO: 26) |
| XpYp | XpYpB | chrX: 12573 hg38 | CGAGCAAGCATCGGAACGTGACT (SEQ ID NO: 27) |
|  | XpYpM | chrX: 11688 | ACCAGGTTTTCCAGTGTGTT (SEQ ID NO: 28) |
|  | XpYpO | chrX: 11660 | CCTGTAACGCTGTTAGGTAC (SEQ ID NO: 29) |
|  | XpYpC | chrX: 10896 | CAGGGACCGGGACAAATAGAC (SEQ ID NO: 30) |
|  | XpYpP | chrX: 10575 | ACCAGGGGCTGATGTAACG (SEQ ID NO: 31) |
|  | XpYpE2 | chrX: 10427 | TGTCTCAGGGTCCTAGTG (SEQ ID NO: 32) |
|  | XpYpE3 | chrX: 10425 | TCTCAGGGTCCTAGTGTG (SEQ ID NO: 33) |
|  | XpYpE4 | chrX: 10429 | GTTGTCTCAGGGTCCTAG (SEQ ID NO: 34) |
|  | XpYpE5 | chrX: 10432 | GGGGTTGTCTCAGGGTCC (SEQ ID NO: 35) |
|  | XpYpE6 | chrX: 10437 | TTCTAGGGGTTGTCTCAG (SEQ ID NO: 36) |
|  | XpYpE7 | chrX: 10439 | TCTTCTAGGGGTTGTCTC (SEQ ID NO: 37) |
|  | XpYpJ | chrX: 10064 | CTAATCTGCTCCCWCCCAC (SEQ ID NO: 38) |

TABLE 2

| Well | Sample ID | Lower allele Range | gel 1 Avg. Size | gel 2 Avg. Size | gel 3 Avg. Size | Average | SD | % CV |
|---|---|---|---|---|---|---|---|---|
| A1 | SampA1 | 2000 bp to 4500 bp | 2968 | 3040 | 3038 | 3015.333 | 41.00406 | 1.359852 |
| A2 | SampA2 | 2000 bp to 4500 bp | 3020 | 3071 | 3020 | 3037 | 29.44486 | 0 969538 |
| A3 | SampA3 | 2000 bp to 4500 bp | 2950 | 3035 | 2994 | 2993 | 42.50882 | 1.420275 |
| A4 | SampA4 | 2000 bp to 4500 bp | 2948 | 3017 | 3022 | 2995.667 | 41.35618 | 1.380533 |
| A5 | Samp A5 | 2000 bp to 4500 bp | 2938 | 3047 | 2969 | 2984.667 | 56.16345 | 1.881733 |
| A6 | SampA6 | 2000 bp to 4500 bp | 2964 | 2985 | 2982 | 2977 | 11.35782 | 0.381519 |
| A7 | SampA7 | 2000 bp to 4500 bp | 2967 | 3026 | 3039 | 3010.667 | 38.371 | 1.274502 |
| A8 | SampA8 | 2000 bp to 4500 bp | 3116 | 3039 | 3040 | 3065 | 44.17013 | 1.441113 |
| A9 | SaropA9 | 2000 bp to 4500 bp | 2962 | 3030 | 3007 | 2999.667 | 34.58805 | 1.153063 |
| A10 | SompA10 | 2000 bp to 4500 bp | 2970 | 3048 | 2968 | 2995.333 | 45.62163 | 1.52309 |
| A11 | SampA11 | 2000 bp to 4500 bp | 3132 | 3028 | 2952 | 3037.333 | 90.36223 | 2 975052 |
| A12 | SampA12 | 2000 bp to 4500 bp | 2994 | 3045 | 2992 | 3010.333 | 30.03886 | 0.997858 |
| B1 | SampB1 | 2000 bp to 4500 bp | 2950 | 3016 | 2979 | 2981.667 | 33.08071 | 1.10947 |
| B2 | SampB2 | 2000 bp to 4500 bp | 2974 | 3059 | 2980 | 3004.333 | 47.43758 | 1.578975 |
| B3 | SampB3 | 2000 bp to 4500 bp | 2982 | 3006 | 3036 | 3008 | 27.0555 | 0.899451 |
| B4 | SampB4 | 2000 bp to 4500 bp | 2981 | 3016 | 3065 | 3020.667 | 42.194 | 1.396844 |
| B5 | SampB5 | 2000 bp to 4500 bp | 3005 | 3074 | 3052 | 3043.667 | 35.24675 | 1.158036 |

TABLE 2-continued

| | | | | | | | | |
|---|---|---|---|---|---|---|---|---|
| B6 | SampB6 | 2000 bp to 4500 bp | 2966 | 2809 | 2966 | 2913.667 | 90.64399 | 3.110994 |
| B7 | SampB7 | 2000 bp to 4500 bp | 2962 | 3049 | 3002 | 3004.333 | 43.54691 | 1.44947 |
| B8 | SampB8 | 2000 bp to 4500 bp | 2969 | 3068 | 2942 | 2993 | 66.34003 | 2.216506 |
| B9 | SampB9 | 2000 bp to 4500 bp | 2978 | 3056 | 3014 | 3016 | 39.03844 | 1.294378 |
| B10 | SampB10 | 2000 bp to 4500 bp | 2970 | 3075 | 2993 | 3011.667 | 55.1936 | 1.832051 |
| B11 | SampB11 | 2000 bp to 4500 bp | 2942 | 3030 | 2971 | 2981 | 44.84417 | 1.504333 |
| B12 | SampB12 | 2000 bp to 4500 bp | 2975 | 3069 | 3007 | 3017 | 47.79121 | 1.584064 |
| C1 | SampC1 | 2000 bp to 4500 bp | 2985 | 3053 | 3022 | 3020 | 34.04409 | 1.127288 |
| C2 | SampC2 | 2000 bp to 4500 bp | 2950 | 3003 | 3039 | 2997.333 | 44.76978 | 1.493654 |
| C3 | SampC3 | 2000 bp to 4500 bp | 2923 | 3052 | 3007 | 2994 | 65.47519 | 2.18688 |
| C4 | SampC4 | 2000 bp to 4500 bp | 2881 | 3002 | 3009 | 2964 | 71.96527 | 2.427978 |
| C5 | SampC5 | 2000 bp to 4500 bp | 2994 | 3027 | 3006 | 3009 | 16.70329 | 0.555111 |
| C6 | SampC6 | 2000 bp to 4500 bp | 2990 | 3083 | 3031 | 3034.667 | 46.6083 | 1.535862 |
| C7 | SampC7 | 2000 bp to 4500 bp | 3000 | 3047 | 3014 | 3020.333 | 24.13158 | 0.798971 |
| C8 | SampC8 | 2000 bp to 4500 bp | 3135 | 3018 | 3030 | 3061 | 64.36614 | 2.102781 |
| C9 | SampC9 | 2000 bp to 4500 bp | 2970 | 3057 | 2963 | 2996.667 | 52.36729 | 1.747518 |
| C10 | SampC10 | 2000 bp to 4500bp | 3062 | 3007 | 2924 | 2997.667 | 69.47182 | 2.31753 |
| C11 | SampC11 | 2000 bp to 4500 bp | 2963 | 2687 | 3037 | 2895.667 | 184.4596 | 6.370194 |
| C12 | SampC12 | 2000 bp to 4500 bp | 2937 | 3038 | 3051 | 3008.667 | 62.40459 | 2.074161 |
| D1 | SampD1 | 2000 bp to 4500 bp | 2987 | 3027 | 3040 | 3018 | 27.62245 | 0.915257 |
| D2 | SampD2 | 2000 bp to 4500 bp | 2954 | 2936 | 2988 | 2959.333 | 26.40707 | 0.892332 |
| D3 | SampD3 | 2000 bp to 4500 bp | 3002 | 3066 | 3050 | 3039.333 | 33.30666 | 1.095854 |
| D4 | SampD4 | 2000 bp to 4500 bp | 2944 | 2979 | 3020 | 2981 | 38.03945 | 1.276064 |
| D5 | SampD5 | 2000 bp to 4500 bp | 3018 | 3044 | 3073 | 3045 | 27.51363 | 0.903568 |
| D6 | SampD6 | 2000 bp to 4500 bp | 2945 | 3038 | 3038 | 3007 | 53.69358 | 1.785619 |
| D7 | SannpD7 | 2000 bp to 4500 bp | 2923 | 2993 | 2992 | 2969.333 | 40.12896 | 1.351447 |
| D8 | SampD8 | 2000 bp to 4500 bp | 2951 | 3058 | 2981 | 2996.667 | 55.1936 | 1.841833 |
| D9 | SampD9 | 2000 bp to 4500 bp | 2981 | 3037 | 3032 | 3016.667 | 30.98925 | 1.027268 |
| D10 | SampD10 | 2000 bp to 4500 bp | 3000 | 3023 | 2934 | 2985.667 | 46.19885 | 1.547354 |
| D11 | SampD11 | 2000 bp to 4500 bp | 3027 | 2757 | 3037 | 2940.333 | 158.85 | 5.40245 |
| D12 | SampD12 | 2000 bp to 4500 bp | 2988 | 3046 | 3027 | 3020.333 | 29.56913 | 0.979002 |
| E1 | SampE1 | 2000 bp to 4500 bp | 2960 | 2998 | 3022 | 2993.333 | 31.26233 | 1.044399 |
| E2 | SampE2 | 2000 bp to 4500 bp | 2967 | 2999 | 3047 | 3004.333 | 40.26578 | 1.340257 |
| E3 | SampE3 | 2000 bp to 4500 bp | 2990 | 3007 | 3049 | 3015.333 | 30.36994 | 1.007184 |
| E4 | SampE4 | 2000 bp to 4500 bp | 2992 | 2994 | 3000 | 2995.333 | 4.163332 | 0.138994 |
| E5 | SampE5 | 2000 bp to 4500 bp | 2961 | 3017 | 3005 | 2994.333 | 29.48446 | 0.984675 |
| E6 | SampE6 | 2000 bp to 4500 bp | 2976 | 2991 | 2976 | 2981 | 8.660254 | 0.290515 |
| E7 | SampE7 | 2000 bp to 4500 bp | 3008 | 3061 | 3029 | 3032.667 | 26.68957 | 0.880069 |
| E8 | SampE8 | 2000 bp to 4500 bp | 2961 | 2971 | 2969 | 2967 | 5.291503 | 0.178345 |
| E9 | SampE9 | 2000 bp to 4500 bp | 3030 | 3036 | 3011 | 3025.667 | 13.05118 | 0.431349 |
| E10 | SampE10 | 2000 bp to 4500 bp | 2979 | 3062 | 2952 | 2997.667 | 57.32655 | 1.912372 |
| E11 | SampE11 | 2000 bp to 4500 bp | 2999 | 3038 | 3040 | 3025.667 | 23.11565 | 0.763985 |
| E12 | SampE12 | 2000 bp to 4500 bp | 2984 | 3065 | 2969 | 3006 | 51.64301 | 1.717998 |
| F1 | SampF1 | 2000 bp to 4500 bp | 2957 | 2993 | 2991 | 2980.333 | 20.23199 | 0.67885 |
| F2 | SampF2 | 2000 bp to 4500 bp | 2997 | 3027 | 3044 | 3022.667 | 23.79776 | 0.78731 |
| F3 | SampF3 | 2000 bp to 4500 bp | 3009 | 2985 | 3021 | 3005 | 18.3303 | 0.609993 |
| F4 | SampF4 | 2000 bp to 4500 bp | 2968 | 3000 | 3005 | 2991 | 20.07486 | 0.671176 |
| F5 | SampF5 | 2000 bp to 4500 bp | 3009 | 3011 | 2974 | 2998 | 20.80865 | 0 694084 |
| F6 | SampF6 | 2000 bp to 4500 bp | 2975 | 3022 | 3001 | 2999.333 | 23.54428 | 0.784984 |
| F7 | SampF7 | 2000 bp to 4500 bp | 3037 | 3050 | 2984 | 3023.667 | 34.96188 | 1.156274 |
| F8 | SampF8 | 2000 bp to 4500 bp | 3002 | 2992 | 2999 | 2997.667 | 5.131601 | 0.171187 |
| F9 | SampF9 | 2000 bp to 4500 bp | 2988 | 3005 | 2990 | 2994.333 | 9.291573 | 0.310305 |
| F10 | SampF10 | 2000 bp to 4500 bp | 3132 | 3026 | 3009 | 3055.667 | 66.65083 | 2.181221 |
| F11 | SampF11 | 2000 bp to 4500 bp | 2960 | 3030 | 2960 | 2983.333 | 40.41452 | 1.354677 |
| F12 | SampF12 | 2000 bp to 4500 bp | 3170 | 3034 | 2924 | 3042.667 | 123.2288 | 4.050026 |
| G1 | SampG1 | 2000 bp to 4500 bp | 3102 | 3135 | 2942 | 3059.667 | 103.2295 | 3.373881 |
| G2 | SampG2 | 2000 bp to 4500bp | 2971 | 2993 | 3006 | 2990 | 17.69181 | 0.591699 |
| G3 | SampG3 | 2000 bp to 4500 bp | 3003 | 2946 | 3038 | 2995.667 | 46.43634 | 1.550117 |
| G4 | SampG4 | 2000 bp to 4500bp | 2962 | 2981 | 3005 | 2982.667 | 21.5484 | 0.722454 |
| G5 | SampG5 | 2000 bp to 4500 bp | 2991 | 2995 | 2978 | 2988 | 8.888194 | 0.297463 |
| G6 | SampG6 | 2000 bp to 4500 bp | 2957 | 2982 | 3038 | 2992.333 | 41.4769 | 1.386106 |
| G7 | SampG7 | 2000 bp to 4500 bp | 2949 | 2992 | 3016 | 2985.667 | 33.94604 | 1.136967 |
| G8 | SampG8 | 2000 bp to 4500 bp | 2822 | 2913 | 2968 | 2901 | 73.73602 | 2.541745 |
| G9 | SampG9 | 2000 bp to 4500 bp | 2912 | 2992 | 2980 | 2961.333 | 43.14317 | 1.456883 |
| G10 | SampG10 | 2000 bp to 4500 bp | 2953 | 3024 | 2989 | 2988.667 | 35.50117 | 1.18786 |
| G11 | SampG11 | 2000 bp to 4500 bp | 2889 | 2988 | 2954 | 2943.667 | 50.30242 | 1.708835 |
| G12 | SampG12 | 2000 bp to 4500 bp | 2907 | 2981 | 2910 | 2932.667 | 41 88476 | 1.428214 |
| H1 | SampH1 | 2000 bp to 4500 bp | 3078 | 2969 | 2960 | 3002.333 | 65.68358 | 2.187751 |
| H2 | SampH2 | 2000 bp to 4500 bp | 2939 | 2987 | 3000 | 2975.333 | 32.12994 | 1.079877 |
| H3 | SampH3 | 2000 bp to 4500 bp | 2941 | 3005 | 3008 | 2984.667 | 37.84618 | 1.26802 |
| H4 | SampH4 | 2000 bp to 4500 bp | 2985 | 3032 | 3025 | 3014 | 25.35744 | 0.841322 |
| H5 | SampH5 | 2000 bp to 4500 bp | 2958 | 3019 | 2991 | 2989.333 | 30.53413 | 1.021436 |
| H6 | SampH6 | 2000 bp to 4500 bp | 2990 | 3038 | 3038 | 3022 | 27.71281 | 0.917036 |
| H7 | SampH7 | 2000 bp to 4500 bp | 2961 | 2979 | 3028 | 2989.333 | 34.67468 | 1.159947 |
| H8 | SampH8 | 2000 bp to 4500 bp | 2950 | 2968 | 2974 | 2964 | 12.49 | 0.42139 |
| H9 | SampH9 | 2000 bp to 4500 bp | 2972 | 3033 | 3011 | 3005.333 | 30.89229 | 1.027915 |

TABLE 2-continued

| Well | Sample ID | Range | | | | | | |
|---|---|---|---|---|---|---|---|---|
| H10 | SampH10 | 2000 bp to 4500 bp | 2940 | 3012 | 2978 | 2976.667 | 36.01851 | 1.210028 |
| H11 | SampH11 | 2000 bp to 4500 bp | 2949 | 3006 | 2925 | 2960 | 41.60529 | 1.405584 |
| | | | | | | Overall average | | 1.407489 |

| | Upper allele | | gel 1 | gel 2 | gel 3 | | | |
|---|---|---|---|---|---|---|---|---|
| Well | Sample ID | Range | Avg. Size | Avg. Size | Avg. Size | Average | SD | % CV |
| A1 | SampA1 | 6000 bp to 9000 bp | 7507 | 7499 | 7458 | 7488 | 26.28688 | 0.351053 |
| A2 | SampA2 | 6000 bp to 9000 bp | 7914 | 7747 | 7501 | 7720.667 | 207.7555 | 2.690901 |
| A3 | SampA3 | 6000 bp to 9000 bp | 7487 | 7534 | 7335 | 7452 | 104.0144 | 1.395792 |
| A4 | SampA4 | 6000 bp to 9000 bp | 7489 | 7512 | 7458 | 7486.333 | 27.09859 | 0.361974 |
| A5 | SampA5 | 6000 bp to 9000 bp | 7662 | 7498 | 7402 | 7520.667 | 131.4737 | 1.748165 |
| A6 | SampA6 | 6000 bp to 9000 bp | 7494 | 7465 | 7448 | 7469 | 23.25941 | 0.311413 |
| A7 | SampA7 | 6000 bp to 9000 bp | 7479 | 7439 | 7414 | 7444 | 32.78719 | 0.440451 |
| A8 | SampA8 | 6000 bp to 9000 bp | 7711 | 7527 | 7402 | 7546.667 | 155.4359 | 2.059664 |
| A9 | SampA9 | 6000 bp to 9000 bp | 7515 | 7503 | 7433 | 7483.667 | 44.28694 | 0.591781 |
| A10 | SampA10 | 6000 bp to 9000 bp | 7574 | 7578 | 7366 | 7506 | 121.2601 | 1.615508 |
| A11 | SampA11 | 6000 bp to 9000 bp | 7698 | 7500 | 7321 | 7506.333 | 188.5798 | 2.512276 |
| A12 | SampA12 | 6000 bp to 9000 bp | 7466 | 7410 | 7349 | 7408.333 | 58.5178 | 0.789892 |
| B1 | SampB1 | 6000 bp to 9000 bp | 7487 | 7497 | 7367 | 7450.333 | 72.34178 | 0.970987 |
| B2 | SampB2 | 6000 bp to 9000 bp | 7600 | 7544 | 7421 | 7521.667 | 91.56601 | 1.217363 |
| B3 | SampB3 | 6000 bp to 9000 bp | 7462 | 7464 | 7379 | 7435 | 4a 50773 | 0.652424 |
| B4 | SampB4 | 6000 bp to 9000 bp | 7511 | 7539 | 7461 | 7503.667 | 39.51371 | 0.526592 |
| B5 | SampB5 | 6000 bp to 9000 bp | 7524 | 7478 | 7294 | 7432 | 121.7046 | 1.637575 |
| B6 | SampB6 | 6000 bp to 9000 bp | 7451 | 7852 | 7298 | 7533.667 | 286.102 | 3.797646 |
| B7 | SampB7 | 6000 bp to 9000 bp | 7438 | 7466 | 7311 | 7405 | 82.60145 | 1.115482 |
| B8 | SampB8 | 6000 bp to 9000 bp | 7486 | 7543 | 7238 | 7422.333 | 162.1614 | 2.184777 |
| B9 | SampB9 | 6000 bp to 9000 bp | 7527 | 7478 | 7437 | 7480.667 | 45.05922 | 0.602342 |
| B10 | SampB10 | 6000 bp to 9000 bp | 7403 | 7486 | 7341 | 7410 | 72.75301 | 0.981822 |
| B11 | SampB11 | 6000 bp to 9000 bp | 7516 | 7484 | 7398 | 7466 | 61.02459 | 0.817367 |
| B12 | SampB12 | 6000 bp to 9000 bp | 7495 | 7490 | 7399 | 7461.333 | 54.04011 | 0.724269 |
| C1 | SampC1 | 6000 bp to 9000 bp | 7623 | 7581 | 7490 | 7564.667 | 67.98774 | 0.898754 |
| C2 | SampC2 | 6000 bp to 9000 bp | 7556 | 7524 | 7404 | 7494.667 | 80.13322 | 1.069203 |
| C3 | SampC3 | 6000 bp to 9000 bp | 7520 | 7415 | 7446 | 7460.333 | 53.94751 | 0.723125 |
| C4 | SampC4 | 6000 bp to 9000 bp | 7480 | 7542 | 7444 | 7488.667 | 49.5715 | 0.661954 |
| C5 | SampC5 | 6000 bp to 9000 bp | 7543 | 7508 | 7388 | 7479.667 | 81.29166 | 1.086835 |
| C6 | SampC6 | 6000 bp to 9000 bp | 7541 | 7421 | 7429 | 7463.667 | 67.09198 | 0.898914 |
| C7 | SampC7 | 6000 bp to 9000 bp | 7484 | 7475 | 7346 | 7435 | 77.20751 | 1.038433 |
| C8 | SampC8 | 6000 bp to 9000 bp | 7734 | 7455 | 7465 | 7551.333 | 158.273 | 2.095961 |
| C9 | SampC9 | 6000 bp to 9000 bp | 7538 | 7510 | 7317 | 7455 | 120.3287 | 1.614067 |
| C10 | SampC10 | 6000 bp to 9000 bp | 7664 | 7462 | 7279 | 7468.333 | 192.5781 | 2.578596 |
| C11 | SampC11 | 6000 bp to 9000 bp | 7429 | 7113 | 7317 | 7286.333 | 160.2165 | 2.198863 |
| C12 | SampC12 | 6000 bp to 9000 bp | 7434 | 7434 | 7378 | 7415.333 | 32.33162 | 0.43601 |
| D1 | SampD1 | 6000 bp to 9000 bp | 7537 | 7515 | 7399 | 7483.667 | 74.144 | 0.990744 |
| D2 | SampD2 | 6000 bp to 9000 bp | 7553 | 7432 | 7428 | 7471 | 71.04224 | 0.950907 |
| D3 | SampD3 | 6000 bp to 9000 bp | 7595 | 7457 | 7542 | 7531.333 | 69.61561 | 0.924346 |
| D4 | SampD4 | 6000 bp to 9000 bp | 7552 | 7547 | 7511 | 7536.667 | 22.26813 | 0.296791 |
| D5 | SampD5 | 6000 bp to 9000 bp | 7589 | 7479 | 7531 | 7533 | 55.02727 | 0.730483 |
| D6 | SampD6 | 6000 bp to 9000 bp | 7587 | 7551 | 7565 | 7567.667 | 18.14754 | 0.239804 |
| D7 | SampD7 | 6000 bp to 9000 bp | 7599 | 7569 | 7531 | 7566.333 | 34.07834 | 0.450394 |
| D8 | SampD8 | 6000 bp to 9000 bp | 7459 | 7541 | 7331 | 7443.667 | 105.8364 | 1.421831 |
| D9 | SampD9 | 6000 bp to 9000 bp | 7480 | 7439 | 7428 | 7449 | 27.40438 | 0.367893 |
| D10 | SampD10 | 6000 bp to 9000 bp | 7473 | 7388 | 7297 | 7386 | 88.01704 | 1.191674 |
| D11 | SampD11 | 6000 bp to 9000 bp | 7537 | 7624 | 7461 | 7540.667 | 81.56184 | 1.081626 |
| D12 | SampD12 | 6000 bp to 9000 bp | 7502 | 7470 | 7333 | 7435 | 89.77193 | 1.207423 |
| E1 | SampE1 | 6000 bp to 9000 bp | 7570 | 7503 | 7490 | 7521 | 42.93018 | 0.570804 |
| E2 | SampE2 | 6000 bp to 9000 bp | 7522 | 7507 | 7454 | 7494.333 | 35.72581 | 0.476704 |
| E3 | SampE3 | 6000 bp to 9000 bp | 7601 | 7440 | 7474 | 7505 | 84.85871 | 1.130696 |
| E4 | SampE4 | 6000 bp to 9000 bp | 7596 | 7437 | 7533 | 7522 | 80.06872 | 1.064461 |
| E5 | SampE5 | 6000 bp to 9000 bp | 7465 | 7469 | 7428 | 7454 | 22.60531 | 0.303264 |
| E6 | SampE6 | 6000 bp to 9000 bp | 7609 | 7522 | 7500 | 7543.667 | 57.63969 | 0.76408 |
| E7 | SampE7 | 6000 bp to 9000 bp | 7452 | 7451 | 7325 | 7409.333 | 73.03652 | 0.985737 |
| E8 | SampE8 | 6000 bp to 9000 bp | 7568 | 7454 | 7363 | 7461.667 | 102.7148 | 1.376567 |
| E9 | SampE9 | 6000 bp to 9000 bp | 7576 | 7457 | 7479 | 7504 | 63.31666 | 0.843772 |
| E10 | SampE10 | 6000 bp to 9000 bp | 7512 | 7482 | 7326 | 7440 | 99.8599 | 1.342203 |
| E11 | SampE11 | 6000 bp to 9000 bp | 7497 | 7442 | 7359 | 7432.667 | 69.47182 | 0.934682 |
| E12 | SampE12 | 6000 bp to 9000 bp | 7455 | 7476 | 7323 | 7418 | 82.93974 | 1.118088 |
| F1 | SampF1 | 6000 bp to 9000 bp | 7452 | 7388 | 7431 | 7423.667 | 32.62412 | 0.439461 |
| F2 | SampF2 | 6000 bp to 9000 bp | 7613 | 7488 | 7442 | 7514.333 | 88.48917 | 1 177605 |
| F3 | SampF3 | 6000 bp to 9000 bp | 7533 | 7339 | 7412 | 7428 | 97.98469 | 1.319126 |
| F4 | SampF4 | 6000 bp to 9000 bp | 7516 | 7471 | 7400 | 7462.333 | 58.48362 | 0.783718 |
| F5 | SampF5 | 6000 bp to 9000 bp | 7546 | 7481 | 7355 | 7460.667 | 97.1099 | 1.301625 |
| F6 | SampF6 | 6000 bp to 9000 bp | 7491 | 7440 | 7355 | 7428.667 | 68.70468 | 0.924859 |
| F7 | SampF7 | 6000 bp to 9000 bp | 7534 | 7542 | 7451 | 7509 | 50.38849 | 0.671041 |
| F8 | SampF8 | 6000 bp to 9000 bp | 7486 | 7440 | 7345 | 7423.667 | 71.90503 | 0.968592 |
| F9 | SampF9 | 6000 bp to 9000 bp | 7475 | 7440 | 7404 | 7439.667 | 35.50117 | 0.477188 |
| F10 | SampF10 | 6000 bp to 9000 bp | 7654 | 7385 | 7435 | 7491.333 | 143.0746 | 1.909868 |

TABLE 2-continued

| | | | | | | | | |
|---|---|---|---|---|---|---|---|---|
| F11 | SampF11 | 6000 bp to 9000 bp | 7457 | 7464 | 7325 | 7415.333 | 78.30922 | 1.056044 |
| F12 | SampF12 | 6000 bp to 9000 bp | 7705 | 7442 | 7311 | 7486 | 200.6514 | 2.680356 |
| G1 | SampG1 | 6000 bp to 9000 bp | 7657 | 7411 | 7416 | 7494.667 | 140.607 | 1.876094 |
| G2 | SampG2 | 6000 bp to 9000 bp | 7485 | 7540 | 7432 | 7485.667 | 54.00309 | 0.72142 |
| G3 | SampG3 | 6000 bp to 9000 bp | 7549 | 7363 | 7424 | 7445.333 | 94.81737 | 1.273514 |
| G4 | SampG4 | 6000 bp to 9000 bp | 7578 | 7505 | 7443 | 7508.667 | 67.57465 | 0.899955 |
| G5 | SampG5 | 6000 bp to 9000 bp | 7556 | 7381 | 7311 | 7416 | 126.1943 | 1.701649 |
| G6 | SampG6 | 6000 bp to 9000 bp | 7524 | 7467 | 7470 | 7487 | 32.07803 | 0.42845 |
| G7 | SampG7 | 6000 bp to 9000 bp | 7476 | 7445 | 7449 | 7456.667 | 16.86219 | 0.226136 |
| G8 | SampGS | 6000 bp to 9000 bp | 7239 | 7452 | 7379 | 7356.667 | 108.242 | 1.471346 |
| G9 | SampG9 | 6000 bp to 9000 bp | 7479 | 7455 | 7403 | 7445.667 | 38.85014 | 0.521782 |
| G10 | SampG10 | 6000 bp to 9000 bp | 7450 | 7444 | 7358 | 7417.333 | 51.47168 | 0.693938 |
| G11 | SampG11 | 6000 bp to 9000 bp | 7426 | 7505 | 7323 | 7418 | 91.26336 | 1.230296 |
| G12 | SampG12 | 6000 bp to 9000 bp | 7426 | 7474 | 7344 | 7414.667 | 65.73685 | 0.886579 |
| H1 | SampH1 | 6000 bp to 9000 bp | 7625 | 7416 | 7331 | 7457.333 | 151.2955 | 2.028815 |
| H2 | SampH2 | 6000 bp to 9000 bp | 7523 | 7425 | 7459 | 7469 | 49.75942 | 0.666213 |
| H3 | SampH3 | 6000 bp to 9000 bp | 7452 | 7449 | 7360 | 7420.333 | 52.27173 | 0.704439 |
| H4 | SampH4 | 6000 bp to 9000 bp | 7470 | 7482 | 7468 | 7473.333 | 7.571878 | 0.101319 |
| H5 | SampH5 | 6000 bp to 9000 bp | 7495 | 7409 | 7352 | 7418.667 | 71.98842 | 0.970369 |
| H6 | SampH6 | 6000 bp to 9000 bp | 7481 | 7458 | 7455 | 7464.667 | 14.22439 | 0.190556 |
| H7 | SampH7 | 6000 bp to 9000 bp | 7551 | 7449 | 7383 | 7461 | 84.64042 | 1.134438 |
| H8 | SampH8 | 6000 bp to 9000 bp | 7485 | 7405 | 7381 | 7423.667 | 54.45487 | 0.733531 |
| H9 | SampH9 | 6000 bp to 9000 bp | 7511 | 7454 | 7460 | 7475 | 31.32092 | 0.419009 |
| H10 | SampH10 | 6000 bp to 9000 bp | 7440 | 7462 | 7350 | 7417.333 | 59.34082 | 0.800029 |
| H11 | SampH11 | 6000 bp to 9000 bp | 7404 | 7375 | 7284 | 7354.333 | 62.61257 | 0.85137 |
| | | | | | | Overall average | | 1.056884 |

The invention claimed is:

1. A high throughput single telomere length analysis method (HT-STELA) for determining telomere length of mammalian chromosomal DNA comprising:
   i) annealing a primer to a region that is between 3843 bp-300 bp from a telomere repeat array of chromosomal DNA;
   ii) PCR amplifying 20 ng-35 ng of said chromosomal DNA using 21-23 cycles to generate an amplification product; and
   iii) detecting the length of the amplification product where the length of the amplification product is indicative of the length of said telomere.

2. The method according to claim 1 wherein part ii) involves PCR amplifying 25 ng-30 ng of said chromosomal DNA using 21-23 cycles to generate an amplification product.

3. The method according to claim 1 wherein part iii) involves attaching a fluorescent label to the PCR amplification product where said fluorescent label provides a signal of at least 25 relative fluorescence units (RFU); or a signal that is at least 25% Telomere Peak area under a curve representative of generated product/Marker peak area under a curve representative of generated marker product when 0.5 ng/µl of marker is used at an injection rate of 1 Kv-value per 10 seconds.

4. The method according to claim 1 wherein said chromosomal DNA was subjected to 23 PCR cycles or 30 ng of chromosomal DNA was subjected to 23 PCR cycles.

5. The method according to claim 1 wherein said primer concentration is selected from the group consisting of: 0.1, 0.2, 0.3, 0.4, 0.5, 0.6, 0.7 or 0.8 µM.

6. The method according to claim 1 wherein said chromosomal DNA is extracted from at least one cell using an automated extraction method.

7. The method according to claim 6 wherein said cell is extracted from any biological sample, or processed derivative thereof.

8. The method according to claim 7 wherein said biological sample is a complex cell sample or a purified cell sample.

9. The method according to claim 7 wherein said biological sample comprises whole blood.

10. The method according to claim 6 wherein about or less than $6 \times 10^5$ cells are used for the extraction method.

11. The method according to claim 10 wherein between $2 \times 10^5$ and $6 \times 10^5$ cells are used for the extraction method.

12. The method according to claim 10 wherein $4 \times 10^5$ cells are used for the extraction method.

13. The method according to claim 1, further including digesting said chromosomal DNA with a restriction endonuclease that cleaves non-telomeric DNA prior to said step of annealing.

14. The method according to claim 13 wherein said restriction endonuclease does not cleave between the 5' end of said primer and the telomere repeat array or the 5' end of said primer and the chromosome telomere end.

15. The method according to claim 1 wherein part iii) involves the use of a lower marker that is larger than 200 bp but smaller than the smallest fragment size of a telomere identified using the HT-STELA method.

16. The method according to claim 15 wherein said lower marker is selected from the group consisting of: 882 bp, 881 bp, 880 bp, 879 bp, 878 bp, 877 bp, 876 bp, 875 bp, 874 bp, 873 bp, 872 bp, 871 bp, 870 bp, 410 bp, 409 bp, 408 bp, 407 bp, 406 bp, 405 bp, 404 bp, 403 bp, 402 bp, 401 bp, 400 bp, 399 bp, 398 bp, 397 bp, 396 bp, 395 bp, 394 bp, 393 bp, 392 bp, 391 bp, and 390 bp including all 0.1 kb integers there between.

17. The method according to claim 1 further including the use of an upper marker selected from the group consisting of: 10 kb, 11 kb, 12 kb, 13 kb, 14 kb, 15 kb, 16 kb, 17 kb, 18 kb, 19 kb and 20 kb, including all 0.1 kb integers there between.

18. The method according to claim 1 wherein said primer binds to telomere specific nucleotides at the 3' end.

19. The method according to claim 1, wherein said primer is designed to bind to 7q chromosome and is selected from the group consisting SEQ ID NOS: 5-10.

20. The method according to claim 1, wherein said primer is designed to bind to bind to 12q chromosome and is selected from the group consisting of SEQ ID NO: 12-17.

21. The method according to claim 1, wherein said primer is designed to bind to XpYp chromosome and is selected from the group consisting SEQ ID NOS: 27-38.

22. The method according to claim 1, wherein said primer is designed to bind to 17p chromosome and is selected from the group consisting of SEQ ID NOS: 19-25.

23. The method according to claim 1, wherein said primer is designed to bind to 2p chromosome and comprise of SEQ ID NO: 1.

24. The method according to claim 1 wherein said mammalian chromosomal DNA is taken from an individual having or at risk of developing a condition selected from the group consisting of: cancer, ageing, neurological disorders including Alzheimer's disease, Parkinson's disease and other dementias, brain infarction, heart disease, chronic HIV infection, chronic hepatitis, skin diseases, chronic inflammatory bowel disease including ulcerative colitis, anaemia, atherosclerosis, Barrett's oesophagus and cancers including pre-cancerous conditions, infertility, telomere syndromes including dyskeratosis congenita, aplastic anaemia, idiopathic pulmonary fibrosis, familial myelodysplastic syndrome-acute myeloid leukaemia, Hoyeraal-Hreiderasson syndrome, Revesz syndrome, Coats plus syndrome, bone marrow failure, and cryptogenic liver cirrhosis.

25. The method according to claim 1 wherein said mammalian chromosomal DNA is taken to assess an individual's suitability to be a transplantation donor.

26. The method of claim 1, wherein said primer is designed to bind to 4q chromosome or 4q chromosome and comprise of SEQ ID NO: 2 or SEQ ID NO: 3, respectively.

27. The method of claim 1 wherein said primer is designed to bind to 5p chromosome or 11q chromosome and comprise of SEQ ID NO: 4 or SEQ ID: 11, respectively.

28. The method of claim 1, wherein said primer is designed to bind to 16p chromosome or 18q chromosome and comprise of SEQ ID NO: 18 or SEQ ID NO: 26, respectively.

* * * * *